United States Patent
Gall et al.

(10) Patent No.: US 9,723,705 B2
(45) Date of Patent: Aug. 1, 2017

(54) CONTROLLING INTENSITY OF A PARTICLE BEAM

(71) Applicant: Mevion Medical Systems, Inc., Littleton, MA (US)

(72) Inventors: Kenneth P. Gall, Harvard, MA (US); Gerrit Townsend Zwart, Durham, NH (US); Jan Van der Laan, Danvers, MA (US); Adam C. Molzahn, Leominster, MA (US); Charles D. O'Neal, III, Bolton, MA (US); Thomas C. Sobczynski, Arlington, MA (US); James Cooley, Andover, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 151 days.

(21) Appl. No.: 14/039,307

(22) Filed: Sep. 27, 2013

(65) Prior Publication Data
US 2014/0094638 A1    Apr. 3, 2014

Related U.S. Application Data

(60) Provisional application No. 61/707,466, filed on Sep. 28, 2012.

(51) Int. Cl.
*H05H 7/12* (2006.01)
*H05H 7/02* (2006.01)
(Continued)

(52) U.S. Cl.
CPC ............. *H05H 7/02* (2013.01); *A61N 5/1077* (2013.01); *H05H 7/12* (2013.01); *H05H 13/02* (2013.01);
(Continued)

(58) Field of Classification Search
None
See application file for complete search history.

(56) References Cited

U.S. PATENT DOCUMENTS

| 2,280,606 A | 4/1942 | Roberts |
| 2,492,324 A | 12/1949 | Salisbury |

(Continued)

FOREIGN PATENT DOCUMENTS

| AU | 2005267078 A1 | 2/2006 |
| CA | 2629333 A1 | 5/2007 |

(Continued)

OTHER PUBLICATIONS

US 8,581,524, 11/2013, O'Neal et al. (withdrawn)
(Continued)

*Primary Examiner* — Douglas W Owens
*Assistant Examiner* — Srinivas Sathiraju
(74) *Attorney, Agent, or Firm* — Choate, Hall & Stewart LLP; Paul Pysher

(57) ABSTRACT

In an example, a synchrocyclotron includes a particle source to provide pulses of ionized plasma to a cavity; a voltage source to provide a radio frequency (RF) voltage to the cavity to accelerate particles from the plasma column outwardly; and an extraction channel to receive a beam of particles from the cavity for output from the particle accelerator. The particle source is configured to control pulse widths of the ionized plasma in order to control an intensity of the beam of particles. This example synchrocyclotron may include one or more of the following features, either alone or in combination.

44 Claims, 21 Drawing Sheets

(51) Int. Cl.
*H05H 13/02* (2006.01)
*A61N 5/10* (2006.01)
*H05H 7/08* (2006.01)

(52) U.S. Cl.
CPC ............... *A61N 2005/1087* (2013.01); *H05H 2007/082* (2013.01); *H05H 2007/122* (2013.01)

(56) References Cited

U.S. PATENT DOCUMENTS

| | | |
|---|---|---|
| 2,615,129 A | 10/1952 | Mcmillan |
| 2,616,042 A | 10/1952 | Ray |
| 2,659,000 A | 11/1953 | Salisbury |
| 2,701,304 A | 2/1955 | Dickinson |
| 2,789,222 A | 4/1957 | Martin et al. |
| 2,958,327 A | 11/1960 | Geissmann |
| 3,175,131 A | 3/1965 | Burleigh et al. |
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,886,367 A | 5/1975 | Castle, Jr. |
| 3,925,676 A | 12/1975 | Bigham et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Taumann et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,736,173 A | 4/1988 | Basil, Jr. et al. |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevet |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hernandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,297,037 A | 3/1994 | Ifuku |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,451,794 A | 9/1995 | McKeown et al. |
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,633,747 A | 5/1997 | Nikoonahad |
| 5,635,721 A | 6/1997 | Bardi et al. |
| 5,668,371 A | 9/1997 | Deasy et al. |
| 5,672,878 A | 9/1997 | Yao |
| 5,691,679 A | 11/1997 | Ackermann et al. |
| 5,726,448 A | 3/1998 | Smith et al. |
| 5,727,554 A | 3/1998 | Kalend et al. |
| 5,730,745 A | 3/1998 | Schulte et al. |
| 5,751,781 A | 5/1998 | Brown et al. |
| 5,778,047 A | 7/1998 | Mansfield et al. |
| 5,783,914 A | 7/1998 | Hiramoto et al. |
| 5,784,431 A | 7/1998 | Kalend et al. |
| 5,797,924 A | 8/1998 | Schulte et al. |
| 5,811,944 A | 9/1998 | Sampayan et al. |
| 5,818,058 A | 10/1998 | Nakanishi et al. |
| 5,821,705 A | 10/1998 | Caporaso et al. |
| 5,825,845 A | 10/1998 | Blair et al. |

(56) References Cited

U.S. PATENT DOCUMENTS

| | | |
|---|---|---|
| 5,841,237 A | 11/1998 | Alton |
| 5,846,043 A | 12/1998 | Spath |
| 5,851,182 A | 12/1998 | Sahadevan |
| 5,866,912 A | 2/1999 | Slater et al. |
| 5,874,811 A | 2/1999 | Finlan et al. |
| 5,895,926 A | 4/1999 | Britton et al. |
| 5,917,293 A | 6/1999 | Saito et al. |
| 5,920,601 A | 7/1999 | Nigg et al. |
| 5,929,458 A | 7/1999 | Nemezawa et al. |
| 5,963,615 A | 10/1999 | Egley et al. |
| 5,993,373 A | 11/1999 | Nonaka et al. |
| 6,008,499 A | 12/1999 | Hiramoto et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Schweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,366,021 B1 | 4/2002 | Meddaugh et al. |
| 6,369,585 B2 | 4/2002 | Yao |
| 6,380,545 B1 | 4/2002 | Yan |
| 6,407,505 B1 | 6/2002 | Bertsche |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,981 B1 | 12/2002 | Schweikard et al. |
| 6,519,316 B1 | 2/2003 | Collins |
| 6,576,916 B2 | 6/2003 | Smith et al. |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,717,162 B1 | 4/2004 | Jongen |
| 6,736,831 B1 | 5/2004 | Hartmann et al. |
| 6,745,072 B1 | 6/2004 | Badura et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B1 | 8/2004 | Schulte |
| 6,799,068 B1 | 9/2004 | Hartmann et al. |
| 6,800,866 B2 | 10/2004 | Amemiya et al. |
| 6,803,591 B2 | 10/2004 | Yamashita et al. |
| 6,814,694 B1 | 11/2004 | Pedroni |
| 6,822,244 B2 | 11/2004 | Beloussov et al. |
| 6,853,142 B2 | 2/2005 | Chistyakov |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,102,144 B2 | 9/2006 | Matsuda et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,424 B2 | 8/2007 | Moriyama et al. |
| 7,262,565 B2 | 8/2007 | Fujisawa |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |
| 7,307,264 B2 | 12/2007 | Brusasco et al. |
| 7,317,192 B2 * | 1/2008 | Ma .................. G21K 1/08 250/298 |
| 7,318,805 B2 | 1/2008 | Schweikard et al. |
| 7,319,231 B2 | 1/2008 | Moriyama et al. |
| 7,319,336 B2 | 1/2008 | Baur et al. |

(56) References Cited

U.S. PATENT DOCUMENTS

| | | | |
|---|---|---|---|
| 7,331,713 B2 | 2/2008 | Moyers | |
| 7,332,880 B2 | 2/2008 | Ina et al. | |
| 7,345,291 B2 | 3/2008 | Kats | |
| 7,345,292 B2 | 3/2008 | Moriyama et al. | |
| 7,348,557 B2 | 3/2008 | Armit | |
| 7,348,579 B2 | 3/2008 | Pedroni | |
| 7,351,988 B2 | 4/2008 | Naumann et al. | |
| 7,355,189 B2 | 4/2008 | Yanagisawa et al. | |
| 7,368,740 B2 | 5/2008 | Beloussov et al. | |
| 7,372,053 B2 | 5/2008 | Yamashita et al. | |
| 7,378,672 B2 | 5/2008 | Harada | |
| 7,381,979 B2 | 6/2008 | Yamashita et al. | |
| 7,397,054 B2 | 7/2008 | Natori et al. | |
| 7,397,901 B1 | 7/2008 | Johnsen | |
| 7,398,309 B2 | 7/2008 | Baumann et al. | |
| 7,402,822 B2 | 7/2008 | Guertin et al. | |
| 7,402,823 B2 | 7/2008 | Guertin et al. | |
| 7,402,824 B2 | 7/2008 | Guertin et al. | |
| 7,402,963 B2 | 7/2008 | Sliski et al. | |
| 7,405,407 B2 | 7/2008 | Hiramoto et al. | |
| 7,425,717 B2 | 9/2008 | Matsuda et al. | |
| 7,432,516 B2 | 10/2008 | Peggs et al. | |
| 7,439,528 B2 | 10/2008 | Nishiuchi et al. | |
| 7,446,328 B2 | 11/2008 | Rigney et al. | |
| 7,446,490 B2 | 11/2008 | Jongen et al. | |
| 7,449,701 B2 | 11/2008 | Fujimaki et al. | |
| 7,453,076 B2 | 11/2008 | Welch et al. | |
| 7,456,415 B2 | 11/2008 | Yanagisawa et al. | |
| 7,465,944 B2 | 12/2008 | Ueno et al. | |
| 7,466,085 B2 | 12/2008 | Nutt | |
| 7,468,506 B2 | 12/2008 | Rogers et al. | |
| 7,473,913 B2 | 1/2009 | Hermann et al. | |
| 7,476,867 B2 | 1/2009 | Fritsch et al. | |
| 7,476,883 B2 | 1/2009 | Nutt | |
| 7,482,606 B2 | 1/2009 | Groezinger et al. | |
| 7,491,161 B2 * | 2/2009 | Taguchi | G03G 15/751 399/116 |
| 7,492,556 B2 | 2/2009 | Atkins et al. | |
| 7,507,975 B2 | 3/2009 | Mohr | |
| 7,518,108 B2 * | 4/2009 | Frey | H01J 49/0045 250/281 |
| 7,525,104 B2 | 4/2009 | Harada | |
| 7,541,905 B2 | 6/2009 | Antaya | |
| 7,547,901 B2 | 6/2009 | Guertin et al. | |
| 7,554,096 B2 | 6/2009 | Ward et al. | |
| 7,554,097 B2 | 6/2009 | Ward et al. | |
| 7,555,103 B2 | 6/2009 | Johnsen | |
| 7,557,358 B2 | 7/2009 | Ward et al. | |
| 7,557,359 B2 | 7/2009 | Ward et al. | |
| 7,557,360 B2 | 7/2009 | Ward et al. | |
| 7,557,361 B2 | 7/2009 | Ward et al. | |
| 7,560,715 B2 | 7/2009 | Pedroni | |
| 7,560,717 B2 | 7/2009 | Matsuda et al. | |
| 7,567,694 B2 | 7/2009 | Lu et al. | |
| 7,574,251 B2 | 8/2009 | Lu et al. | |
| 7,576,499 B2 | 8/2009 | Caporaso et al. | |
| 7,579,603 B2 | 8/2009 | Birgy et al. | |
| 7,579,610 B2 | 8/2009 | Grozinger et al. | |
| 7,582,866 B2 | 9/2009 | Furuhashi et al. | |
| 7,582,885 B2 | 9/2009 | Katagiri et al. | |
| 7,582,886 B2 | 9/2009 | Trbojevic | |
| 7,586,112 B2 | 9/2009 | Chiba et al. | |
| 7,598,497 B2 | 10/2009 | Yamamoto et al. | |
| 7,609,009 B2 | 10/2009 | Tanaka et al. | |
| 7,609,809 B2 | 10/2009 | Kapatoes et al. | |
| 7,609,811 B1 | 10/2009 | Siljamaki et al. | |
| 7,615,942 B2 | 11/2009 | Sanders et al. | |
| 7,626,347 B2 | 12/2009 | Sliski et al. | |
| 7,627,267 B2 * | 12/2009 | Saiki | G03G 21/181 399/113 |
| 7,629,598 B2 | 12/2009 | Harada | |
| 7,639,853 B2 | 12/2009 | Olivera et al. | |
| 7,639,854 B2 | 12/2009 | Schnarr et al. | |
| 7,643,661 B2 | 1/2010 | Ruchala et al. | |
| 7,656,258 B1 | 2/2010 | Antaya et al. | |
| 7,659,521 B2 | 2/2010 | Pedroni | |
| 7,659,528 B2 | 2/2010 | Uematsu | |
| 7,668,291 B2 | 2/2010 | Nord et al. | |
| 7,672,429 B2 | 3/2010 | Urano et al. | |
| 7,679,073 B2 | 3/2010 | Urano et al. | |
| 7,682,078 B2 | 3/2010 | Rietzel | |
| 7,692,166 B2 | 4/2010 | Muraki et al. | |
| 7,692,168 B2 | 4/2010 | Moriyama et al. | |
| 7,696,499 B2 | 4/2010 | Miller et al. | |
| 7,696,847 B2 | 4/2010 | Antaya | |
| 7,701,677 B2 | 4/2010 | Schultz et al. | |
| 7,709,818 B2 | 5/2010 | Matsuda et al. | |
| 7,710,051 B2 | 5/2010 | Caporaso et al. | |
| 7,718,982 B2 | 5/2010 | Sliski et al. | |
| 7,728,311 B2 | 6/2010 | Gall | |
| 7,746,978 B2 | 6/2010 | Cheng et al. | |
| 7,755,305 B2 | 7/2010 | Umezawa et al. | |
| 7,759,642 B2 | 7/2010 | Nir | |
| 7,763,867 B2 | 7/2010 | Birgy et al. | |
| 7,767,988 B2 | 8/2010 | Kaiser et al. | |
| 7,770,231 B2 | 8/2010 | Prater et al. | |
| 7,772,577 B2 | 8/2010 | Saito et al. | |
| 7,773,723 B2 | 8/2010 | Nord et al. | |
| 7,773,788 B2 | 8/2010 | Lu et al. | |
| 7,778,488 B2 | 8/2010 | Nord et al. | |
| 7,783,010 B2 | 8/2010 | Clayton | |
| 7,784,127 B2 | 8/2010 | Kuro et al. | |
| 7,786,451 B2 | 8/2010 | Ward et al. | |
| 7,786,452 B2 | 8/2010 | Ward et al. | |
| 7,789,560 B2 | 9/2010 | Moyers | |
| 7,791,051 B2 | 9/2010 | Beloussov et al. | |
| 7,796,731 B2 | 9/2010 | Nord et al. | |
| 7,801,269 B2 | 9/2010 | Cravens et al. | |
| 7,801,270 B2 | 9/2010 | Nord et al. | |
| 7,801,988 B2 | 9/2010 | Baumann et al. | |
| 7,807,982 B2 | 10/2010 | Nishiuchi et al. | |
| 7,809,107 B2 | 10/2010 | Nord et al. | |
| 7,812,319 B2 | 10/2010 | Diehl et al. | |
| 7,812,326 B2 | 10/2010 | Grozinger et al. | |
| 7,816,657 B2 | 10/2010 | Hansmann et al. | |
| 7,817,778 B2 | 10/2010 | Nord et al. | |
| 7,817,836 B2 | 10/2010 | Chao et al. | |
| 7,834,334 B2 | 11/2010 | Grozinger et al. | |
| 7,834,336 B2 | 11/2010 | Boeh et al. | |
| 7,835,494 B2 | 11/2010 | Nord et al. | |
| 7,835,502 B2 | 11/2010 | Spence et al. | |
| 7,839,972 B2 | 11/2010 | Ruchala et al. | |
| 7,839,973 B2 | 11/2010 | Nord et al. | |
| 7,848,488 B2 | 12/2010 | Mansfield | |
| 7,857,756 B2 | 12/2010 | Warren et al. | |
| 7,860,216 B2 | 12/2010 | Jongen et al. | |
| 7,860,550 B2 | 12/2010 | Saracen et al. | |
| 7,868,301 B2 | 1/2011 | Diehl | |
| 7,875,861 B2 | 1/2011 | Huttenberger et al. | |
| 7,875,868 B2 | 1/2011 | Moriyama et al. | |
| 7,881,431 B2 | 2/2011 | Aoi et al. | |
| 7,894,574 B1 | 2/2011 | Nord et al. | |
| 7,906,769 B2 | 3/2011 | Blasche et al. | |
| 7,914,734 B2 | 3/2011 | Livingston | |
| 7,919,765 B2 * | 4/2011 | Timmer | A61N 5/10 250/492.3 |
| 7,920,040 B2 | 4/2011 | Antaya et al. | |
| 7,920,675 B2 | 4/2011 | Lomax et al. | |
| 7,928,415 B2 | 4/2011 | Bert et al. | |
| 7,934,869 B2 | 5/2011 | Ivanov et al. | |
| 7,940,881 B2 | 5/2011 | Jongen et al. | |
| 7,943,913 B2 | 5/2011 | Balakin | |
| 7,947,969 B2 | 5/2011 | Pu | |
| 7,949,096 B2 | 5/2011 | Cheng et al. | |
| 7,950,587 B2 | 5/2011 | Henson et al. | |
| 7,960,710 B2 | 6/2011 | Kruip et al. | |
| 7,961,844 B2 | 6/2011 | Takeda et al. | |
| 7,977,648 B2 | 7/2011 | Westerly et al. | |
| 7,977,656 B2 | 7/2011 | Fujimaki et al. | |
| 7,977,657 B2 | 7/2011 | Flynn et al. | |
| 7,982,198 B2 | 7/2011 | Nishiuchi et al. | |
| 7,982,416 B2 | 7/2011 | Tanaka et al. | |
| 7,984,715 B2 | 7/2011 | Moyers | |
| 7,986,768 B2 | 7/2011 | Nord et al. | |

(56) References Cited

U.S. PATENT DOCUMENTS

| | | | |
|---|---|---|---|
| 7,987,053 B2 | 7/2011 | Schaffner | |
| 7,989,785 B2 | 8/2011 | Emhofer et al. | |
| 7,990,524 B2 | 8/2011 | Jureller et al. | |
| 7,997,553 B2 | 8/2011 | Sloan et al. | |
| 8,002,466 B2 | 8/2011 | Von Neubeck et al. | |
| 8,003,964 B2 | 8/2011 | Stark et al. | |
| 8,009,803 B2 | 8/2011 | Nord et al. | |
| 8,009,804 B2 | 8/2011 | Siljamaki et al. | |
| 8,039,822 B2 | 10/2011 | Rietzel | |
| 8,041,006 B2 | 10/2011 | Boyden et al. | |
| 8,044,364 B2 | 10/2011 | Yamamoto | |
| 8,049,187 B2 | 11/2011 | Tachikawa | |
| 8,053,508 B2 | 11/2011 | Korkut et al. | |
| 8,053,739 B2 | 11/2011 | Rietzel | |
| 8,053,745 B2 | 11/2011 | Moore | |
| 8,053,746 B2 | 11/2011 | Timmer et al. | |
| 8,063,381 B2 | 11/2011 | Tsoupas et al. | |
| 8,067,748 B2 | 11/2011 | Balakin | |
| 8,069,675 B2 | 12/2011 | Radovinsky et al. | |
| 8,071,966 B2 | 12/2011 | Kaiser et al. | |
| 8,080,801 B2 | 12/2011 | Safai | |
| 8,085,899 B2 | 12/2011 | Nord et al. | |
| 8,089,054 B2 | 1/2012 | Balakin | |
| 8,093,564 B2 | 1/2012 | Balakin | |
| 8,093,568 B2 | 1/2012 | Mackie et al. | |
| 8,111,125 B2 | 2/2012 | Antaya et al. | |
| 8,129,699 B2 | 3/2012 | Balakin | |
| 8,144,832 B2 | 3/2012 | Balakin | |
| 8,153,989 B2 | 4/2012 | Tachikawa et al. | |
| 8,173,981 B2 | 5/2012 | Trbojevic | |
| 8,188,688 B2 | 5/2012 | Balakin | |
| 8,198,607 B2 | 6/2012 | Balakin | |
| 8,222,613 B2 | 7/2012 | Tajiri et al. | |
| 8,227,768 B2 | 7/2012 | Smick et al. | |
| 8,232,536 B2 | 7/2012 | Harada | |
| 8,288,742 B2 | 10/2012 | Balakin | |
| 8,291,717 B2 | 10/2012 | Radovinsky et al. | |
| 8,294,127 B2 | 10/2012 | Tachibana | |
| 8,304,725 B2 | 11/2012 | Komuro et al. | |
| 8,304,750 B2 | 11/2012 | Preikszas et al. | |
| 8,309,941 B2 | 11/2012 | Balakin | |
| 8,330,132 B2 | 12/2012 | Guertin et al. | |
| 8,334,520 B2 | 12/2012 | Otaka et al. | |
| 8,335,397 B2 | 12/2012 | Takane et al. | |
| 8,344,340 B2 | 1/2013 | Gall et al. | |
| 8,350,214 B2 | 1/2013 | Otaki et al. | |
| 8,368,038 B2 | 2/2013 | Balakin | |
| 8,368,043 B2 | 2/2013 | Havelange et al. | |
| 8,373,143 B2 | 2/2013 | Balakin | |
| 8,373,145 B2 | 2/2013 | Balakin | |
| 8,373,146 B2 | 2/2013 | Balakin | |
| 8,378,299 B2 | 2/2013 | Frosien | |
| 8,378,321 B2 | 2/2013 | Balakin | |
| 8,382,943 B2 | 2/2013 | Clark | |
| 8,389,949 B2 | 3/2013 | Harada et al. | |
| 8,399,866 B2 | 3/2013 | Balakin | |
| 8,405,042 B2 | 3/2013 | Honda et al. | |
| 8,405,056 B2* | 3/2013 | Amaldi | A61N 5/10 250/396 R |
| 8,415,643 B2 | 4/2013 | Balakin | |
| 8,416,918 B2 | 4/2013 | Nord et al. | |
| 8,421,041 B2 | 4/2013 | Balakin | |
| 8,426,833 B2 | 4/2013 | Trbojevic | |
| 8,436,323 B2 | 5/2013 | Iseki et al. | |
| 8,440,987 B2 | 5/2013 | Stephani et al. | |
| 8,445,872 B2 | 5/2013 | Behrens et al. | |
| 8,466,441 B2 | 6/2013 | Iwata et al. | |
| 8,472,583 B2 | 6/2013 | Star-Lack et al. | |
| 8,483,357 B2 | 7/2013 | Siljamaki et al. | |
| 8,487,278 B2 | 7/2013 | Balakin | |
| 8,552,406 B2 | 10/2013 | Phaneuf et al. | |
| 8,552,408 B2 | 10/2013 | Hanawa et al. | |
| 8,569,717 B2 | 10/2013 | Balakin | |
| 8,575,563 B2 | 11/2013 | Cameron et al. | |
| 8,581,215 B2 | 11/2013 | Balakin | |
| 8,581,523 B2* | 11/2013 | Gall | H05H 13/02 315/501 |
| 8,581,525 B2 | 11/2013 | Antaya et al. | |
| 8,637,833 B2 | 1/2014 | Balakin | |
| 8,653,314 B2 | 2/2014 | Pelati et al. | |
| 8,653,473 B2 | 2/2014 | Yajima | |
| 8,766,218 B2 | 7/2014 | Jongen | |
| 8,791,435 B2 | 7/2014 | Balakin | |
| 8,901,509 B2 | 12/2014 | Balakin | |
| 8,905,908 B2* | 12/2014 | Matsuguma | F16C 17/02 184/100 |
| 8,907,311 B2 | 12/2014 | Gall et al. | |
| 8,952,634 B2* | 2/2015 | Sliski | H05H 13/02 315/502 |
| 8,963,112 B1 | 2/2015 | Balakin | |
| 8,970,137 B2* | 3/2015 | Gall | H05H 13/02 315/501 |
| 8,975,816 B2 | 3/2015 | Scheitrum et al. | |
| 9,012,866 B2 | 4/2015 | Benna et al. | |
| 9,028,384 B2* | 5/2015 | Iikura | F16C 33/128 264/271.1 |
| 9,044,600 B2 | 6/2015 | Balakin | |
| 9,056,199 B2 | 6/2015 | Balakin | |
| 9,176,468 B2* | 11/2015 | Ueno | G03G 15/757 |
| 9,451,688 B2 | 9/2016 | Jongen | |
| 9,452,301 B2 | 9/2016 | Gall et al. | |
| 2002/0172317 A1 | 11/2002 | Maksimchuk et al. | |
| 2003/0048080 A1 | 3/2003 | Amemiya et al. | |
| 2003/0125622 A1 | 7/2003 | Schweikard et al. | |
| 2003/0136924 A1 | 7/2003 | Kraft et al. | |
| 2003/0146759 A1* | 8/2003 | Bashkirov | H01J 49/40 324/464 |
| 2003/0152197 A1 | 8/2003 | Moyers | |
| 2003/0163015 A1 | 8/2003 | Yanagisawa et al. | |
| 2003/0183779 A1 | 10/2003 | Norimine et al. | |
| 2003/0234369 A1 | 12/2003 | Glukhoy | |
| 2004/0000650 A1 | 1/2004 | Yanagisawa et al. | |
| 2004/0017888 A1 | 1/2004 | Seppi et al. | |
| 2004/0056212 A1 | 3/2004 | Yanagisawa et al. | |
| 2004/0061077 A1 | 4/2004 | Muramatsu et al. | |
| 2004/0061078 A1 | 4/2004 | Muramatsu et al. | |
| 2004/0085023 A1 | 5/2004 | Chistyakov | |
| 2004/0098445 A1 | 5/2004 | Baumann et al. | |
| 2004/0111134 A1 | 6/2004 | Muramatsu et al. | |
| 2004/0118081 A1 | 6/2004 | Reimoser et al. | |
| 2004/0149934 A1 | 8/2004 | Yanagisawa et al. | |
| 2004/0159795 A1 | 8/2004 | Kaercher et al. | |
| 2004/0173763 A1 | 9/2004 | Moriyama et al. | |
| 2004/0174958 A1 | 9/2004 | Moriyama et al. | |
| 2004/0183033 A1 | 9/2004 | Moriyama et al. | |
| 2004/0183035 A1 | 9/2004 | Yanagisawa et al. | |
| 2004/0200982 A1 | 10/2004 | Moriyama et al. | |
| 2004/0200983 A1 | 10/2004 | Fujimaki et al. | |
| 2004/0213381 A1 | 10/2004 | Harada | |
| 2004/0227104 A1 | 11/2004 | Matsuda et al. | |
| 2004/0232356 A1 | 11/2004 | Norimine et al. | |
| 2004/0240626 A1 | 12/2004 | Moyers | |
| 2005/0058245 A1 | 3/2005 | Ein-Gal | |
| 2005/0089141 A1 | 4/2005 | Brown | |
| 2005/0161618 A1 | 7/2005 | Pedroni | |
| 2005/0184686 A1 | 8/2005 | Caporaso et al. | |
| 2005/0228255 A1 | 10/2005 | Saracen et al. | |
| 2005/0234327 A1 | 10/2005 | Saracen et al. | |
| 2005/0238134 A1 | 10/2005 | Brusasco et al. | |
| 2005/0247890 A1 | 11/2005 | Norimine et al. | |
| 2006/0017015 A1 | 1/2006 | Sliski et al. | |
| 2006/0067468 A1 | 3/2006 | Rietzel | |
| 2006/0126792 A1 | 6/2006 | Li | |
| 2006/0145088 A1 | 7/2006 | Ma | |
| 2006/0170381 A1 | 8/2006 | Amaldi et al. | |
| 2006/0173294 A1 | 8/2006 | Ein-Gal | |
| 2006/0175991 A1 | 8/2006 | Fujisawa | |
| 2006/0273264 A1 | 12/2006 | Nakayama et al. | |
| 2006/0284562 A1 | 12/2006 | Hruby et al. | |
| 2007/0001128 A1 | 1/2007 | Sliski et al. | |
| 2007/0013273 A1 | 1/2007 | Albert et al. | |
| 2007/0014654 A1 | 1/2007 | Haverfield et al. | |
| 2007/0023699 A1 | 2/2007 | Yamashita et al. | |
| 2007/0029510 A1 | 2/2007 | Hermann et al. | |

(56) References Cited

U.S. PATENT DOCUMENTS

| | | |
|---|---|---|
| 2007/0051904 A1 | 3/2007 | Kaiser et al. |
| 2007/0061937 A1 | 3/2007 | Curle |
| 2007/0092812 A1 | 4/2007 | Caporaso et al. |
| 2007/0114945 A1 | 5/2007 | Mattaboni et al. |
| 2007/0133752 A1 | 6/2007 | Ein-Gal |
| 2007/0145916 A1 | 6/2007 | Caporaso et al. |
| 2007/0170994 A1 | 7/2007 | Peggs et al. |
| 2007/0171015 A1* | 7/2007 | Antaya .................... H05H 7/04 335/216 |
| 2007/0181519 A1 | 8/2007 | Khoshnevis |
| 2007/0252093 A1 | 11/2007 | Fujimaki et al. |
| 2007/0284548 A1 | 12/2007 | Kaiser et al. |
| 2008/0067452 A1 | 3/2008 | Moriyama et al. |
| 2008/0078937 A1 | 4/2008 | Tsuchiya et al. |
| 2008/0093567 A1 | 4/2008 | Gall |
| 2008/0218102 A1 | 9/2008 | Sliski et al. |
| 2008/0234531 A1* | 9/2008 | Welch ...................... A61N 5/10 600/2 |
| 2008/0270517 A1 | 10/2008 | Baumann et al. |
| 2009/0096179 A1 | 4/2009 | Stark et al. |
| 2009/0101832 A1 | 4/2009 | Diehl |
| 2009/0140671 A1* | 6/2009 | O'Neal, III ............ H05H 13/02 315/502 |
| 2009/0140672 A1* | 6/2009 | Gall ....................... H05H 13/02 315/502 |
| 2009/0200483 A1 | 8/2009 | Gall et al. |
| 2009/0230299 A1 | 9/2009 | Shichi et al. |
| 2009/0236545 A1 | 9/2009 | Timmer |
| 2009/0296885 A1 | 12/2009 | Boeh et al. |
| 2009/0309046 A1 | 12/2009 | Balakin |
| 2009/0314960 A1* | 12/2009 | Balakin ................ A61N 5/1049 250/492.3 |
| 2009/0321665 A1* | 12/2009 | Timmer ................. A61N 5/10 250/492.3 |
| 2010/0006770 A1* | 1/2010 | Balakin ................ A61N 5/1049 250/396 R |
| 2010/0027745 A1* | 2/2010 | Balakin ................ A61B 6/4028 378/65 |
| 2010/0038552 A1 | 2/2010 | Trbojevic |
| 2010/0045213 A1 | 2/2010 | Sliski et al. |
| 2010/0046697 A1* | 2/2010 | Balakin ................ A61N 5/1049 378/21 |
| 2010/0051833 A1 | 3/2010 | Guertin et al. |
| 2010/0192303 A1 | 8/2010 | Miller et al. |
| 2010/0209335 A1* | 8/2010 | Mills ..................... B01J 7/00 423/648.1 |
| 2010/0230617 A1 | 9/2010 | Gall |
| 2010/0308235 A1 | 12/2010 | Sliski et al. |
| 2011/0006212 A1* | 1/2011 | Shchory ............... A61N 5/1049 250/363.01 |
| 2011/0220809 A1 | 9/2011 | Yajima et al. |
| 2011/0233423 A1* | 9/2011 | Balakin ................. G21K 1/087 250/454.11 |
| 2011/0240874 A1 | 10/2011 | Iwata |
| 2011/0284760 A1 | 11/2011 | Balakin |
| 2011/0299919 A1 | 12/2011 | Stark et al. |
| 2012/0014501 A1 | 1/2012 | Pelc et al. |
| 2012/0081041 A1 | 4/2012 | Cheung et al. |
| 2012/0126140 A1 | 5/2012 | Gall et al. |
| 2012/0217903 A1* | 8/2012 | Tanaka ................... H05H 7/12 315/502 |
| 2012/0313003 A1 | 12/2012 | Trbojevic |
| 2013/0053616 A1 | 2/2013 | Gall et al. |
| 2013/0127375 A1 | 5/2013 | Sliski et al. |
| 2013/0131424 A1 | 5/2013 | Sliski et al. |
| 2013/0237425 A1 | 9/2013 | Leigh et al. |
| 2013/0249443 A1* | 9/2013 | Antaya ................ H05H 13/005 315/502 |
| 2014/0028220 A1 | 1/2014 | Bromberg et al. |
| 2014/0042934 A1 | 2/2014 | Tsutsui |
| 2014/0062344 A1* | 3/2014 | Gall ....................... H05H 13/02 315/502 |
| 2014/0094643 A1 | 4/2014 | Gall et al. |
| 2014/0097920 A1 | 4/2014 | Goldie et al. |
| 2015/0009917 A1 | 1/2015 | Cho et al. |
| 2015/0009918 A1 | 1/2015 | Yeoum et al. |
| 2015/0161793 A1 | 6/2015 | Takahashi |
| 2017/0028224 A1 | 2/2017 | Gall et al. |

FOREIGN PATENT DOCUMENTS

| | | |
|---|---|---|
| CN | 1377521 A | 10/2002 |
| CN | 1537657 A | 10/2004 |
| CN | 1631061 A | 6/2005 |
| CN | 101061759 A | 10/2007 |
| CN | 101361156 A | 2/2009 |
| CN | 101932361 A | 12/2010 |
| CN | 101933405 A | 12/2010 |
| CN | 101933406 A | 12/2010 |
| CN | 102036461 A | 4/2011 |
| CN | 102172106 A | 8/2011 |
| CN | 104244562 A | 12/2014 |
| CN | 104812443 A | 7/2015 |
| CN | 104812444 A | 7/2015 |
| CN | 104822417 A | 8/2015 |
| DE | 2753397 A1 | 6/1978 |
| DE | 3148100 A1 | 6/1983 |
| DE | 3530446 A1 | 3/1986 |
| DE | 4101094 C1 | 5/1992 |
| DE | 4411171 A1 | 10/1995 |
| EP | 0044153 A1 | 1/1982 |
| EP | 0194728 A1 | 9/1986 |
| EP | 0208163 A1 | 1/1987 |
| EP | 0221987 A1 | 5/1987 |
| EP | 0222786 A1 | 5/1987 |
| EP | 0276123 A2 | 7/1988 |
| EP | 0277521 A2 | 8/1988 |
| EP | 0306966 A2 | 3/1989 |
| EP | 0388123 A2 | 9/1990 |
| EP | 0465597 A1 | 1/1992 |
| EP | 0499253 A2 | 8/1992 |
| EP | 0776595 A1 | 6/1997 |
| EP | 0864337 A2 | 9/1998 |
| EP | 0911064 A2 | 4/1999 |
| EP | 1069809 A1 | 1/2001 |
| EP | 1153398 A1 | 11/2001 |
| EP | 1265462 A1 | 12/2002 |
| EP | 1294445 A2 | 3/2003 |
| EP | 1348465 A1 | 10/2003 |
| EP | 1358908 A1 | 11/2003 |
| EP | 1371390 A1 | 12/2003 |
| EP | 1402923 A1 | 3/2004 |
| EP | 1430932 A1 | 6/2004 |
| EP | 1454653 A1 | 9/2004 |
| EP | 1454654 A2 | 9/2004 |
| EP | 1454655 A2 | 9/2004 |
| EP | 1454656 A2 | 9/2004 |
| EP | 1454657 A2 | 9/2004 |
| EP | 1477206 A1 | 11/2004 |
| EP | 1605742 A1 | 12/2005 |
| EP | 1738798 A2 | 1/2007 |
| EP | 1790203 A2 | 5/2007 |
| EP | 1826778 A2 | 8/2007 |
| EP | 1949404 A2 | 7/2008 |
| EP | 2026640 A2 | 2/2009 |
| EP | 2183753 A1 | 5/2010 |
| EP | 2227295 A1 | 9/2010 |
| EP | 2232961 A1 | 9/2010 |
| EP | 2232962 A2 | 9/2010 |
| EP | 2259664 A2 | 12/2010 |
| EP | 2363170 A1 | 9/2011 |
| EP | 2363171 A1 | 9/2011 |
| EP | 2394498 A2 | 12/2011 |
| EP | 2814304 A1 | 12/2014 |
| EP | 2900324 A1 | 8/2015 |
| EP | 2900325 A2 | 8/2015 |
| EP | 2900326 A1 | 8/2015 |
| FR | 2560421 A1 | 8/1985 |
| FR | 2911843 A1 | 8/2008 |
| GB | 0957342 A | 5/1964 |
| GB | 1360085 A | 7/1974 |
| GB | 1485329 A | 9/1977 |
| GB | 2015821 A | 9/1979 |

(56) References Cited

FOREIGN PATENT DOCUMENTS

| | | |
|---|---|---|
| GB | 1583400 A | 1/1981 |
| GB | 2361523 A | 10/2001 |
| JP | 61-225798 | 10/1986 |
| JP | 10247600 | 9/1989 |
| JP | 4-94198 | 3/1992 |
| JP | 04-128717 B2 | 4/1992 |
| JP | 04-129768 B2 | 4/1992 |
| JP | 04-273409 B2 | 9/1992 |
| JP | 04-337300 B2 | 11/1992 |
| JP | 05-341352 B2 | 12/1993 |
| JP | 10270200 | 10/1998 |
| JP | 11-47287 | 2/1999 |
| JP | 11-243295 | 9/1999 |
| JP | 2000-243309 A | 9/2000 |
| JP | 2000-294399 A | 10/2000 |
| JP | 2001-6900 | 1/2001 |
| JP | 2001-006900 A | 1/2001 |
| JP | 2001-009050 A | 1/2001 |
| JP | 2001-129103 A | 5/2001 |
| JP | 2001-346893 A | 12/2001 |
| JP | 2002-164686 A | 6/2002 |
| JP | 2003-504628 A | 2/2003 |
| JP | 2003-517755 A | 5/2003 |
| JP | 2004-139944 A | 5/2004 |
| JP | 2005-526578 A | 9/2005 |
| JP | 2006-032282 A | 2/2006 |
| JP | 2006233831 A | 9/2006 |
| JP | 2007260939 A | 10/2007 |
| JP | 2007-319439 A | 12/2007 |
| JP | 2008-012121 A | 1/2008 |
| JP | 2008-507826 A | 3/2008 |
| JP | 2008-089341 A | 4/2008 |
| JP | 2008-270039 A | 11/2008 |
| JP | 2009-515671 A | 4/2009 |
| JP | 2009-516905 A | 4/2009 |
| JP | 43-23267 B2 | 9/2009 |
| JP | 2010-204020 A | 9/2010 |
| JP | 2010-536130 A | 11/2010 |
| JP | 2011-505191 A | 2/2011 |
| JP | 2011-505670 A | 2/2011 |
| JP | 2011-507151 A | 3/2011 |
| JP | 2011-521425 A | 7/2011 |
| JP | 2011-210494 A | 10/2011 |
| JP | 2011-224342 A | 11/2011 |
| JP | 05-046928 B2 | 10/2012 |
| SU | 300137 | 11/1969 |
| SU | 569635 | 8/1977 |
| SU | 569635 A1 | 8/1977 |
| TW | 200930160 A | 7/2009 |
| TW | 200934682 A | 8/2009 |
| TW | 200939908 A | 9/2009 |
| TW | 200940120 A | 10/2009 |
| TW | 201422278 A | 6/2014 |
| TW | 201422279 A | 6/2014 |
| TW | 201424466 A | 6/2014 |
| TW | 201429514 A | 8/2014 |
| TW | 201433331 A | 9/2014 |
| TW | 201434508 A | 9/2014 |
| TW | 201438787 A | 10/2014 |
| WO | WO-86/07229 A1 | 12/1986 |
| WO | WO-90/12413 A1 | 10/1990 |
| WO | WO-92/03028 A1 | 2/1992 |
| WO | WO-93/02536 A1 | 2/1993 |
| WO | WO-98/17342 A2 | 4/1998 |
| WO | WO-99/39385 A1 | 8/1999 |
| WO | WO-00/40064 A2 | 7/2000 |
| WO | WO-00/49624 A1 | 8/2000 |
| WO | WO-01/26230 A1 | 4/2001 |
| WO | WO-01/26569 | 4/2001 |
| WO | WO-02/07817 A2 | 1/2002 |
| WO | WO-03/039212 A1 | 5/2003 |
| WO | WO-03/092340 A1 | 11/2003 |
| WO | WO-03092812 A1 | 11/2003 |
| WO | WO-2004026401 A1 | 4/2004 |
| WO | WO-2004101070 A1 | 11/2004 |
| WO | WO-2005/102453 A1 | 11/2005 |
| WO | WO-2006/012452 A1 | 2/2006 |
| WO | WO-2006/012467 A2 | 2/2006 |
| WO | WO2007/061937 | 5/2007 |
| WO | WO-2007/061937 A2 | 5/2007 |
| WO | WO-2007/084701 A1 | 7/2007 |
| WO | WO-2007/130164 A2 | 11/2007 |
| WO | WO-2007145906 A2 | 12/2007 |
| WO | WO-2008/030911 A2 | 3/2008 |
| WO | WO-2008081480 A1 | 7/2008 |
| WO | WO-2009/048745 A2 | 4/2009 |
| WO | WO-2009/056165 A1 | 5/2009 |
| WO | WO-2009/070173 A1 | 6/2009 |
| WO | WO-2009/070588 A1 | 6/2009 |
| WO | WO-2009073480 A2 | 6/2009 |
| WO | WO-2009080080 A1 | 7/2009 |
| WO | WO-2010089574 A2 | 8/2010 |
| WO | WO2010/149740 | 12/2010 |
| WO | WO-2010/149740 A1 | 12/2010 |
| WO | WO-2012/044957 A1 | 4/2012 |
| WO | WO-2012/071142 A2 | 5/2012 |
| WO | WO-2013/079311 A1 | 6/2013 |
| WO | WO-2013098089 A1 | 7/2013 |
| WO | WO-2013/142409 A1 | 9/2013 |
| WO | WO-2014/018876 A1 | 1/2014 |
| WO | WO-2014/052708 A2 | 4/2014 |
| WO | WO2014/052709 | 4/2014 |
| WO | WO 2014/052716 A2 | 4/2014 |
| WO | WO-2014/052718 A2 | 4/2014 |
| WO | WO-2014/052719 A2 | 4/2014 |
| WO | WO-2014/052721 A1 | 4/2014 |
| WO | WO-2014/052722 A2 | 4/2014 |

OTHER PUBLICATIONS

Tilly, et al., "Development and verification of the pulsed scanned proton beam at The Svedberg Laboratory in Uppsala", Physics in Medicine and Biology, Phys. Med. Biol. 52, pp. 2741-2454, 2007.
U.S. Appl. No. 14/039,342, Corresponding PCT Appln. No. PCT/US2013/062117, Corresponding Provisional U.S. Appl. No. 61/707,515.
U.S. Appl. No. 14/039,073, Corresponding PCT Appln. No. PCT/US2013/062102, Corresponding Provisional U.S. Appl. No. 61/707,548.
U.S. Appl. No. 14/039,084, Corresponding PCT Appln. No. PCT/US2013/062120, Corresponding Provisional U.S. Appl. No. 61/707,572.
U.S. Appl. No. 14/039,652, Corresponding PCT Appln. No. PCT/US2013/062112, Corresponding Provisional U.S. Appl. No. 61/707,590.
U.S. Appl. No. 14/039,752, Corresponding PCT Appln. No. PCT/US2013/062116, Corresponding Provisional U.S. Appl. No. 61/707,704.
U.S. Appl. No. 14/038,888, Corresponding PCT Appln. No. PCT/US2013/062137, Corresponding Provisional U.S. Appl. No. 61/707,624.
U.S. Appl. No. 14/038,967, Corresponding PCT Appln. No. PCT/US2013/062119, Corresponding Provisional U.S. Appl. No. 61/707,645.
U.S. Appl. No. 13/916,401.
U.S. Appl. No. 13/907,601.
U.S. Appl. No. 13/780,118, Corresponding Provisional U.S. Appl. No. 61/605,690.
Corresponding Provisional U.S. Appl. No. 61/883,631.
International Search Report and Written Opinion from corresponding PCT application No. PCT/US2013/062103 mailed Apr. 14, 2014 (14 pages).
Office Action for JP2015-534721, 14 pages (Feb. 3, 2016) (in both Japanese and English).
First Office Action for 201380062111.9, 46 pages (dated Jun. 1, 2016).
Second Office Action (English) for JP2015-534721, 5 pages (dated Dec. 26, 2016).
Second Office Action (Japanese) for JP2015-534721, 5 pages (dated Dec. 26, 2016).

(56) References Cited

OTHER PUBLICATIONS

File History of Reissue U.S. Appl. No. 15/429,078 (downloaded Mar. 13, 2017).
"The Cutting Edge of Cancer Therapy Using Proton Beams," The Journal of Practical Pharmacy, vol. 46, No. 1, 10 pages (1995). [Japanese] (English Abstract).
18th Japan Conference on Radiation and Radioisotopes [Japanese], Nov. 25-27, 1987, 9 pages.
510(k) Summary: Ion Beam Applications S.A., FDA, Jul. 12, 2001, 5 pages.
510(k) Summary: Optivus Proton Beam Therapy System, Jul. 21, 2000, 5 pages.
Abrosimov et al., 1000MeV Proton Beam Therapy facility at Petersburg Nuclear Physics Institute Synchrocyclotron, Medical Radiology (Moscow) 32, 10 (1987) revised in Journal of Physics, Conference Series 41, 2006, pp. 424-432, Institute of Physics Publishing Limited.
Abrosimov et al., Neutron Time-of-flight Spectrometer Gneis at the Gatchina 1 GeV Protron Syncrhocyclotron, Mar. 9, 1985 and revised form Jul. 31, 1985, Lemingrad Nuclear Physics Institute, Gatchina, 188350, USSR (15 pages).
Adachi et al., A 150MeV FFAG Synchrotron with Return-Yoke Free Magent, Proceedings of the 2001 Particle Accelerator Conference, Chicago, 2001, 3 pages.
Ageyev et al., The IHEP Accelerating and Storage Complex (UNK) Status Report, 11th International Conference on High-Energy Accelerators, 1980, pp. 60-70.
Agosteo et al., Maze Design of a gantry room for proton therapy, Nuclear Instruments & Methods In Physics Research, 1996, Section A, 382, pp. 573-582.
Alexeev et al., R4 Design of Superconducting Magents for Proton Synchrotrons, Proceedings of the Fifth International Cryogenic Engineering Conference, 197 4, pp. 531-533.
Allardyce et al., Performance and Prospects of the Reconstructed CERN 600 MeV Synchrocyclotron, IEEE Transactions on Nuclear Science USA, Jun. 1977, ns-24:(3) 1631-1633.
Alonso, Magnetically Scanned Ion Beams for Radiation Therapy, Accelerator & Fusion Research Division, Lawrence Berkeley Laboratory, Berkeley, CA, Oct. 1988, 13 pages.
Amaldi et al., The Italian project for a hadrontherapy centre Nuclear Instruments and Methods in Physics Research A, 1995, 360, pp. 297-301.
Amaldi, Cyclinacs, Novel Fast-Cycling Accelerators for Hadrontherapy, 2007, Cyclotrons and Their Applications, 18th International Conference, pp. 166-168.
Amaldi, Overview of the world landscape of Hadrontherapy and the projects of the TERA foundation, Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
An Accelerated Collaboration Meets with Beaming Success, Lawrence Livermore National Laboratory, Apr. 12, 2006, S&TR, Livermore, California, pp. 1-3, http://www.llnl.gov/str/April06/Caporaso.html.
Anferov et al., Status of the Midwest Proton Radiotherapy Institute, Proceedings of the 2003 Particle Accelerator Conference, 2003, pp. 699-701.
Anferov et al., The Indiana University Midwest Proton Radiation Institute, Proceedings of the 2001 Particle Accelerator Conference, 2001, Chicago, pp. 645-647.
Appun, Various problems of magnet fabrication for high-energy accelerators, Journal for All Engineers Interested in the Nuclear Field, 1967, 11 pages 10-16 (1967) [Lang.: German], English bibliographic information (httn://www.osti.1mv/enernvcitations/nroduct.biblio.isn?ostiid=4442292).
Arduini et al. Physical specifications of clinical proton beams from a synchrotron, Med. Phys, Jun. 1996, 23 ( 6): 939-951.
Badano et al., Proton-Ion Medical Machine Study (PIMMS) Part I, PIMMS, Jan. 1999, 238 pages.
Beam Delivery and Properties, Journal of the ICRU, 2007, 7(2):20 pages.
Beeckman et al., Preliminary design of a reduced cost proton therapy facility using a compact, high field isochronous cyclotron, Nuclear Instruments and Methods in Physics Research B56/57, 1991, pp. 1201-1204.
Bellomo et al., The Superconducting Cyclotron Program at Michigan State University, Bulletin of the American Physical Society, Sep. 1980, 25(7):767.
Benedikt and Carli, Matching to Gantries for Medical Synchrotrons IEEE Proceedings of the 1997 Particle Accelerator Conference, 1997, pp. 13 79-13 81.
Bieth et al., A Very Compact Protontherapy Facility Based on an Extensive Use of High Temperature Superconductors (HTS) Cyclotrons and their Applications 1998, Proceedings of the Fifteenth International Conference on Cyclotrons and their Applications, Caen, Jun. 14-19, 1998, pp. 669-672.
Bigham, Magnetic Trim Rods for Superconducting Cyclotrons, Nuclear Instruments and Methods (North-Holland Publishing Co.), 1975, 141:223-228.
Bimbot, First Studies of the External Beam from the Orsay S.C. 200 MeV, Institut de Physique Nucleaire, BP 1, Orsay, France, IEEE, 1979, pp. 1923-1926.
Blackmore et al., Operation of the Triumf Proton Therapy Facility, IEEE Proceedings of the 1997 Particle Accelerator Conference, May 12-16, 1997, 3:3831-3833.
Bloch, The Midwest Proton Therapy Center, Application of Accelerators in Research and Industry, Proceedings of the Fourteenth Int'l. Conf, Part Two, Nov. 1996, pp. 1253-1255.
Blom, Mikael, Development of a Scanning System for Proton Therapy in Uppsala, Department of Radiation Sciences, Uppsala University, 2450-2451.
Blosser et al., A Compact Superconducting Cyclotron for the Production of High Intensity Protons, Proceedings of the 1997 Particle Accelerator Conference, May 12-16, 1997, 1:1054-1056.
Blosser et al., Advances in Superconducting Cyclotrons at Michigan State University, Proceedings of the 11th International Conference on Cyclotrons and their Applications, Oct. 1986, pp. 157-167, Tokyo.
Blosser et al., Characteristics of a 400 (Q2/A) MeV Super-Conducting Heavy-Ion Cyclotron, Bulletin of the American Physical Society, Oct. 1974, p. 1026.
Blosser et al., Medical Accelerator Projects at Michigan State Univ. IEEE Proceedings of the 1989 Particle Accelerator Conference, Mar. 20-23, 1989, 2:742-746.
Blosser et al., Problems and Accomplishments of Superconducting Cyclotrons, Proceedings of the 14th International Conference, Cyclotrons and Their Applications, Oct. 1995, pp. 674-684.
Blosser et al., Progress toward an experiment to study the effect of RF grounding in an internal ion source on axial oscillations of the beam in a cyclotron, National Superconducting Cyclotron Laboratory, Michigan State University, Report MSUCL-760, CP600, Cyclotrons and their Applications 2011, Sixteenth International Conference, 2001, pp. 274-276.
Blosser et al., Superconducting Cyclotron for Medical Application, IEEE Transactions on Magnetics, Mar. 1989, 25(2): 1746-1754.
Blosser et al., Superconducting Cyclotrons, Seventh International Conference on Cyclotrons and their Applications, Aug. 19-22, 1975, pp. 584-594.
Blosser, Application of Superconductivity in Cyclotron Construction, Ninth International Conference on Cyclotrons and their Applications, Sep. 1981, pp. 147-157.
Blosser, Applications of Superconducting Cyclotrons, Twelfth International Conference on Cyclotrons and Their Applications, May 8-12, 1989, pp. 137-144.
Blosser, Future Cyclotrons, AIP, The Sixth International Cyclotron Conference, 1972, pp. 16-32.
Blosser, H. G. "Compact Superconducting Synchrocyclotron Systems for Proton Therapy," Nuclear Instruments & Methods in Physics Research, Section B40-41, Part II, pp. 1326-1330 (1989).
Blosser, H., Present and Future Superconducting Cyclotrons, Bulletin of the American Physical Society, Feb. 1987, 32(2):171 Particle Accelerator Conference, Washington, D.C.

(56) References Cited

OTHER PUBLICATIONS

Blosser, H.G., "Progress on the Coupled Superconducting Cyclotron Project," Bulletin of the American Physical Society, vol. 26, No. 4, p. 558 (Apr. 1981).
Blosser, H.G., Superconducting Cyclotrons at Michigan State University, Nuclear Instruments & Methods in Physics Research, 1987,vol. B 24/25, part II, pp. 752-756.
Blosser, Medical Cyclotrons, Physics Today, Special Issue Physical Review Centenary, Oct. 1993, pp. 70-73.
Blosser, Preliminary Design Study Exploring Building Features Required for a Proton Therapy Facility for the Ontario Cancer Institute, Mar. 1991, MSUCL-760a, 53 pages.
Blosser, Synchrocyclotron Improvement Programs, IEEE Transactions on Nuclear Science USA, Jun. 1969, 16(3):Part I, pp. 405-414.
Blosser, The Michigan State University Superconducting Cyclotron Program, Nuclear Science, Apr. 1979, NS-26(2):2040-2047.
Botha et al., A New Multidisciplinary Separated-Sector Cyclotron Facility, IEEE Transactions on Nuclear Science, 1977, NS-24(3): 1118-1120.
Canadian Office action from Canadian application No. 2,629,333 dated Aug. 30, 2010 (5 pages).
Canadian Office action from Canadian application No. 2,629,333 dated May 11, 2011 (2 pages).
Canadian office action from Canadian application No. 2574122 dated Aug. 14, 2014 (6 pages).
Chichili et al., Fabrication ofNb3Sn Shell-Type Coils with Pre-Preg Ceramic Insulation, American Institute of Physics Conference Proceedings, AIP USA, No. 711, (XP-002436709, ISSN: 0094-243X), 2004, pp. 450-457.
Chinese Office action from Chinese application No. 200680051421.0 dated Aug. 22, 2011 (4 pages).
Chinese Office action from Chinese application No. 200680051421.0 dated Dec. 25, 2009 (8 pages).
Chinese Office action from Chinese application No. 200680051421.0 dated Mar. 21, 2011 (6 pages).
Chinese Office Action from Chinese Application No. 200780102281.X dated Dec. 7, 2011 with English translation (23 pages).
Chinese Office action from Chinese application No. 200880125832.9, dated Jun. 5, 2012 (5 pages).
Chinese Office action from Chinese application No. 200880125832.9, dated Sep. 22, 2011 (11 pages).
Chinese Office action from Chinese application No. 200880125918.1, dated Sep. 15, 2011 (17 pages).
Chinese Office action with English translation from Chinese Application No. 200880125832.9, dated Mar. 4, 2013 (8 pages).
Chong et al., Radiology Clinic North American 7, 3319, 1969, 27 pages.
Chu et al., Instrumentation for Treatment of Cancer Using Proton and Light-ion Beams, Review of Scientific Instruments, Aug. 1993, 64 (8):2055-2122.
Chu et al., Performance Specifications for Proton Medical Facility, Lawrence Berkeley Laboratory, University of California, Mar. 1993, 128 pages.
Chu, Instrumentation in Medical Systems, Accelerator and Fusion Research Division, Lawrence Berkeley Laboratory, University of California, Berkeley, CA, May 1995, 9 pages.
Cohen, R. et al., Nevis Synchrocyclotron Conversion Project, IEEE Transactions on Nuclear Science, IEEE Service Center, New York, NY, US, vol. 16, No. 3, Jun. 1, 1969, pp. 421-425, XP011351570, ISSN: 0018-9499, DOI: 10.1109/TNS.1969.4325264 abstract; figures I-4a Chap. 1, p. 421-2; chap. 11 from p. 423, col. 2 to p. 425, col. 1. (5 pages).
Cole et al., Design and Application of a Proton Therapy Accelerator, Fermi National Accelerator Laboratory, IEEE, 1985, 5 pages.
Collins, et al., The Indiana University Proton Therapy System, Proceedings of EPAC 2006, Edinburgh, Scotland, 2006, 3 pages.
Conradi et al., Proposed New Facilities for Proton Therapy at iThemba Labs, Proceedings of EPAC, 2002, pp. 560-562.

C/E Source of Ions for Use in Sychro-Cyclotrons Search, Jan. 31, 2005, 9 pages.
Source Search Cites of U.S. And Foreign Patents/Published applications in the name of Mitsubishi Denki Kabushiki Kaisha and Containing the Keywords (Proton and Synchrocyclotron), Jan. 2005, 8 pages.
Cosgrove et al., Microdosimetric Studies on the Orsay Proton Synchrocyclotron at 73 and 200 MeV, Radiation Protection Dosimetry, 1997, 70(1-4):493-496.
Coupland, High-field (5 T) pulsed superconducting dipole magnet, Proceedings of the Institution of Electrical Engineers, Jul. 1974, 121(7):771-778.
Coutrakon et al. Proton Synchrotrons for Cancer Therapy, Application of Accelerators in Research and Industry—Sixteenth International Conf., American Institute of Physics, Nov. 1-5, 2000, vol. 576, pp. 861-864.
Coutrakon et al., A prototype beam delivery system for the proton medical accelerator at Loma Linda, Medical Physics, Nov./Dec. 1991, 18(6):1093-1099.
CPAC Highlights Its Proton Therapy Program at ESTRO Annual Meeting, TomoTherapy Incorporated, Sep. 18, 2008, Madison, Wisconsin, pp. 1-2.
Cuttone, Applications of a Particle Accelerators in Medical Physics, Istituto Nazionale di Fisica Nucleare-Laboratori Nazionali del Sud, V.S. Sofia, 44 Cantania, Italy, Jan. 2010, 17 pages.
Dahl P, Superconducting Magnet System, American Institute of Physics, AIP Conference Proceedings, 1987-1988, 2: 1329-1376.
Dey, M.K., et al., Coil Centering for the Kolkata Superconducting Cyclotron Magnet, Cyclotrons and their applications, Proceedings, 18th International Conference, Cyclotrons 2007, Giardini Naxo, Italy, Oct. 1-5, 2007 (3 pages).
Dialog Search, Jan. 31, 2005, 17 pages.
Dugan et al., Tevatron Status IEEE, Particle Accelerator Conference, Accelerator Science & Technology, 1989, pp. 426-430.
Eickhoff et al., The Proposed Accelerator Facility for Light Ion Cancer Therapy in Heidelberg, Proceedings of the 1999 Particle Accelerator Conference, New York, 1999, pp. 2513-2515.
Elo, Don, et al., Mechanical Design of Regenerative Deflector for the Berkeley 88-Inch Cyclotron, Proceedings of the International Conference on Isochronous Cyclotrons, Gatlinburg, Tennessee, Aug. 1966 (7 pages).
Enchevich et al., Minimizing Phase Losses in the 680 MeV Synchrocyclotron by Correcting the Accelerating Voltage Amplitude, Atomnava Energiva, 1969, 26:(3):315-316.
Endo et al., Compact Proton and Carbon Ion Synchrotrons for Radiation Therapy, Proceedings of EPAC 2002, Paris France, 2002, pp. 2733-2735.
English translation of Chinese Office action from Chinese application No. 200880125832.9, dated Jun. 5, 2012 (5 pages).
European Communication from European application No. 06838033.6 dated Apr. 20, 2010 (7 pages).
European Communication from European application No. 07868958.5, dated Nov. 26, 2010 (50 pages).
European Communication from European application No. 11165423.2 dated Sep. 2, 2011 (5 pages).
European Communication from European application No. 13774886.9 dated Jun. 12, 2015 (2 pages).
European Communication issued in European Application No. 05776532.3 dated Jun. 10, 2011 (10 pages).
European Communication issued in European application No. 13774886.9 dated Jun. 12, 2015, with amended claims filed on Jun. 12, 2015 (20 pages).
European Communication issued in European application No. 13783422.2 dated Jun. 12, 2015 (2 pages).
European Patent Office communication for application No. 06838033.6, patent No. 1949404, dated Aug. 5, 2009 (1 page).
European Patent Office communication from European application No. 07868958.5, dated Jul. 16, 2010 (2 pages).
European Patent Office communication from European application No. 08855024.9, dated Jul. 30, 2010 (2 pages).
European Search Report from application No. EP 06838033.6 (PCT/US2006/044853) dated May 11, 2009 (69 pages).

(56) References Cited

OTHER PUBLICATIONS

European Search Report from application No. EP 06838033.6 (PCT/US2006/044853) dated May 11, 2009 (7 pages).
European Search Report from corresponding European application No. 11165422.4 dated Aug. 8, 2011 (118 pages).
European Search Report from corresponding European application No. 11165423.2 dated Aug. 8, 2011 (118 pages).
European Search Report from European Application No. 10175751.6 dated Nov. 18, 2010 (8 pages).
European Search Report from European application No. 11165422.4 dated Aug. 8, 2011 (118 pages).
European Search Report from European application No. 11165423.2 dated Aug. 8, 2011 (118 pages).
European Search Report issued in European Application No. 08856764.9 dated Jun. 4, 2014 (3 pages).
Extended Search Report for EP10175727, 7 pages (dated Dec. 19, 2015).
Favale, A. et al., Pre-conceptual Design of a Rapid Cycling Medical Synchrotron, The AES/BNL collaboration, 45 pages (Oct. 27, 1999).
File History for U.S. Appl. No. 14/039,307 as of Jan. 13, 2017, 343 pages.
File history of U.S. Appl. No. 10/949,734 (now U.S. Pat. No. 7,208,748) (downloaded Mar. 14, 2017).
File History of U.S. Appl. No. 11/187,633.
File history of U.S. Appl. No. 11/187,633 (downloaded Mar. 14, 2017).
File history of U.S. Appl. No. 11/371,622 (now U.S. Pat. No. 7,402,963) (downloaded Mar. 14, 2017).
File history of U.S. Appl. No. 11/463,403 (now U.S. Pat. No. 7,656,258) (downloaded Mar. 14, 2017).
File history of U.S. Appl. No. 11/517,490 (now U.S. Pat. No. 7,701,677) (downloaded Mar. 14, 2017).
File history of U.S. Appl. No. 11/601,056 (now U.S. Pat. No. 7,728,311) (downloaded Mar. 14, 2017).
File history of U.S. Appl. No. 11/624,769 (now U.S. Pat. No. 7,541,905) (downloaded Mar. 14, 2017).
File history of U.S. Appl. No. 11/724,055 (now U.S. Pat. No. 7,718,982) (downloaded Mar. 14, 2017).
File history of U.S. Appl. No. 11/870,961 (now U.S. Pat. No. 8,003,964) (downloaded Mar. 14, 2017).
File history of U.S. Appl. No. 11/948,662 (now U.S. Pat. No. 8,581,523) (downloaded Mar. 14, 2017).
File history of U.S. Appl. No. 12/275,103 (now U.S. Pat. No. 8,344,340) (downloaded Mar. 14, 2017).
File History of U.S. Appl. No. 13/618,939.
File history of U.S. Appl. No. 14/039,307 (downloaded Mar. 13, 2017).
File history of U.S. Appl. No. 60/590,088 (downloaded Mar. 14, 2017).
File history of U.S. Appl. No. 60/850,565 (downloaded Mar. 14, 2017).
File history of U.S. Appl. No. 60/991,454 (downloaded Mar. 14, 2017).
File History of U.S. Pat. No. 7,402,963.
File History of U.S. Pat. No. 7,626,347.
File History of U.S. Pat. No. 8,952,634.
File History of U.S. Appl. No. 11/187,633, (Mar. 23, 2017).
First Office Action (Chinese translation) for CN201380062115.7, 7 pages (dated Dec. 12, 2016).
First Office Action (English translation) for CN201380062115.7, 9 pages (dated Dec. 12, 2016).
Fish & Richardson P.C., Response to Non Final Office action mailed Aug. 20, 2010 in U.S Appl. No. 11/948,359, filed Feb. 22, 2011 (17 pages).
Flanz et al., Large Medical Gantries, Particle Accelerator Conference, Massachusetts General Hospital, 1995, pp. 1-5.
Flanz et al., Operation of a Cyclotron Based Proton Therapy Facility, Massachusetts General Hospital, Boston, MA 02114, pp. 1-4, retrieved from Internet in 2009.
Flanz et al., The Northeast Proton Therapy Center at Massachusetts General Hospital, Fifth.Workshop on Heavy Charge Particles in Biology and Medicine, GSI, Darmstadt, Aug. 1995, 11 pages.
Flanz et al., Treating Patients with the NPTC Accelerator Based Proton Treatment Facility, Proceedings of the 2003 Particle Accelerator Conference, 2003, pp. 690-693.
Flanz, et al., "Scanning Beam Technologies", PTCOG 2008, 28 pages.
Flood and Frazier, The Wide-Band Driven RF System for the Berkeley 88-Inch Cyclotron, American Institute of Physics, Conference Proceedings., No. 9, 1972, 459-466.
Foster and Kashikhin, Superconducting Superferric Dipole Magent with Cold Iron Core for the VLHC, IEEE Transactions on Applied Superconductivity, Mar. 2002, 12(1):111-115.
Friesel et al., Design and Construction Progress on the IUCF Midwest Proton Radiation Institute, Proceedings of EPAC 2002, 2002, pp. 2736-2738.
Fukumoto et al., A Proton Therapy Facility Plan Cyclotrons and their Applications, Proceedings of the 13th International Conference, Vancouver, Canada, Jul. 6-10, 1992, pp. 258-261.
Fukumoto, Cyclotron Versus Synchrotron for Proton Beam Therapy, KEK Prepr., No. 95-122, Oct. 1995, pp. 533-536.
Gordon, M.M. et. al., "Design Study for a Compact 200 MeV Cyclotron," AIP Conference Proceedings Sixth International Cyclotron Conference, No. 9, pp. 78-86 (1972).
Gordon, M.M., "Extraction Studies for a 250 MeV Superconducting Synchrocyclotron," Proceedings of the 1987 IEEE Particle Accelerator Conference: Accelerator Engineering and Technology, pp. 1255-1257 (1987).
Goto et al., Progress on the Sector Magnets for the Riken SRC, American Institute of Physics, 714 CP600, Cyclotrons and Their Applications 2001, Sixteenth International Conference, 2001, pp. 319-323.
Graffman et al., Acta Radial. Therapy Phys. Biol. 1970, 9, 1 (1970).
Graffman et al., Design Studies for a 200 MeV Proton Clinic for Radiotherapy, AIP Conference Proceedings: Cyclotrons—1972, 1972, No. 9, pp. 603-615.
Graffman, et. al. Proton radiotherapy with the Uppsala cyclotron. Experience and plans Strahlentherapie, 1985, 161(12):764-770.
Grözinger, Sven Oliver, Volume Conformal Irradiation of Moving Target vols. with Scanned Ion Beams, Vom Fachbereich Physik der Technischen Universität Darmstadt, 110 pages (2004).
Hede, Research Groups Promoting Proton Therapy Lite, Journal of the National Cancer Institute, Dec. 6, 2006, 98(23):1682-1684.
Heinz, Superconducting Pulsed Magnetic Systems for High-Energy Synchrotrons, Proceedings of the Fourth International Cryogenic Engineering Conference, May 24-26, 1972, pp. 55-63.
Hentschel et al., Plans for the German National Neutron Therapy Centre with a Hospital-Based 70 MeV Proton Cyclotron at University Hospital Essen/Germany, Cyclotrons and their Applications, Proceedings of the Fifteenth International Conference on Cyclotrons and their Applications, Caen, Franco, Jun. 14-19, 1998, pp. 21-23.
Hepburn et al., Superconducting Cyclotron Neutron Source for Therapy, International Journal of Radiation Oncology Biology Physics, vol. 3 complete, 1977, pp. 387-391.
Hirabayashi, Development of Superconducting Magnets for Beam Lines and Accelerator at KEK, IEEE Transaction on Magnetics, Jan. 1981, Mag-17(1 ):728-731.
Indiana's mega-million proton therapy cancer center welcomes its first patients [online] Press release, Health & Medicine Week, 2004, retrieved from NewsRx.com, Mar. 1, 2004, pp. 119-120.
International Preliminary Report on Patentability for PCT application No. PCT/US2007/001506 dated Jul. 5, 2007 (15 pages).
International Preliminary Report on Patentability from PCT application No. PCT/US2007/086109, dated Jun. 10, 2010 (6 pages).
International Preliminary Report on Patentability from PCT application No. PCT/US2008/084695, dated Jun. 10, 2010 (9 pages).
International Preliminary Report on Patentability from PCT application No. PCT/US2008/084699, dated Jun. 10, 2010 (6 pages).
International Preliminary Report on Patentability from PCT application No. PCT/US2013/062119 dated Mar. 31, 2015 (7 pages).

(56) References Cited

OTHER PUBLICATIONS

International Preliminary Report on Patentability from PCT application No. PCT/US2013/062137 dated Mar. 31, 2015 (9 pages).
International Search Report and Written Opinion for PCT application No. PCT/US2008/084695 dated Jan. 26, 2009 (9 pages).
International Search Report and Written Opinion from PCT application No. PCT/US2013/062119 dated Nov. 26, 2013 (9 pages).
International Search Report and Written Opinion in International Application No. PCT/US2008/084699, dated Feb. 4, 2009, 6 pages.
International Search Report dated Aug. 26, 2008 in PCT application No. PCT/US2007/086109 (3 pages).
International Search Report for PCT/US2007/001628 dated Feb. 18, 2008 (4 pages).
Ishibashi and Mcinturff, Stress Analysis of Superconducting 1 OT Magnets for Synchrotron, Proceedings of the Ninth International Cryogenic Engineering Conference, May 11-14, 1982, pp. 513-516.
Ishibashi and Mcinturff, Winding Design Study of Superconducting 10 T Dipoles for a Synchrotron, IEEE Transactions on Magnetics, May 1983, MAG-19(3):1364-1367.
Jahnke et al., First Superconducting Prototype Magnets for a Compact Synchrotron Radiation Source in Operation, IEEE Transactions on Magnetics, Mar. 1988, 24(2):1230-1232.
Japanese office action issued in Japanese application 2015-534728 dated Mar. 28, 2016 (6 pages). NOTE: English translation has not been received from Associate.
Jones and Dershem, Synchrotron Radiation from Proton in a 20 TEV, 10 TESLA Superconducting Super Collider Proceedings of the 12th International Conference on High-Energy Accelerator, Aug. 11-16, 1983, pp. 138-140.
Jones and Mills, The South African National Accelerator Centre: Particle Therapy and Isotope Production Programmes, Radiation Physics and Chemistry, Apr.-Jun. 1998, 51 ( 4-6):571-578.
Jones et al., Status Report of the NAC Particle Therapy Programme, Stralentherapie and Onkologie, vol. 175, Suppl. II, Jun. 1999, pp. 30-32.
Jones, Present Status and Future Trends of Heavy Particle Radiotherapy, Cyclotrons and their Applications 1998, Proceedings of the Fifteenth International Conference on Cyclotrons and their Applications, Jun. 14-19, 1998, pp. 13-20.
Jones, Progress with the 200 MeV Cyclotron Facility at the National Accelerator Centre, Commission of the European Communities Radiation Protection Proceedings, Fifth Symposium on Neutron Dosimetry, Sep. 17-21, 1984, vol. II, pp. 989-998.
Jongen et al., Development of a Low-cost Compact Cyclotron System for Proton Therapy, National Institute of Radio!. Sci, 1991, No. 81, DD. 189-200.
Jongen et al., Progress report on the IBA-SHI small cyclotron for cancer therapy Nuclear Instruments and Methods in Physics Research, Section B, vol. 79, issue 1-4, 1993, pp. 885-889.
Jongen et al., The proton therapy system for MGH's NPTC: equipment description and progress report, Bulletin du Cancer/Radiotherapie, Proceedings of the meeting of the European Heavy Particle Therapy Group, 1996, 83(Suppl. 1):219-222.
Jongen et al., The proton therapy system for the NPTC: Equipment Description and progress report, Nuclear Instruments and methods in physics research, 1996, Section B, 113(1 ): 522-525.
Kanai et al., Three-dimensional Beam Scanning for Proton Therapy, Nuclear Instruments and Methods in Physic Research, Sep. 1, 1983, The Netherlands, 214(23):491-496.
Kanazawa, M. et al., Beam Control in the Spot Scanning Irradiation, Proceedings of the Second Asian Particle Accelerator Conference, China; 846-848 (2001).
Karlin et al., Medical Radiology (Moscow), 1983, 28, 13.
Karlin et al., The State and Prospects in the Development of the Medical Proton Tract on the Synchrocyclotron in Gatchina, Med. Radial., Moscow, 28(3):28-32 (Mar. 1983)(German with English Abstract on end of p. 32).
Kats and Druzhinin, Comparison of Methods for Irradiation Prone Patients, Atomic Energy, Feb. 2003, 94(2): 120-123.
Kats and Onosovskii, A Planar Magnetooptical System for the Irradiation of a Lying Patient with a Proton Beam from Various Directions, Instruments and Experimental Techniques, 1996, 39(1):127-131.
Kats and Onosovskii, A Simple, Compact, Flat System for the Irradiation of a Lying Patient with a Proton Beam from Different Directions, Instruments and Experimental Techniques, 1996, 39(1):132-134.
Kawachi, K. et al., Three Dimensional Spot Beam Scanning Method for Proton Conformation Radiation Therapy, Acta Radiologica, Supplementum 364, 10 pages (1982).
Khoroshkov et al., Moscow Hospital-Based Proton Therapy Facility Design, Am. Journal Clinical Oncology: CCT, Apr. 1994, 17(2)1 09-114.
Kim and Blosser, Optimized Magnet for a 250 MeV Proton Radiotherapy Cyclotron, Cyclotrons and Their Applications 2001, May 2001, Sixteenth International Conference, pp. 345-347.
Kim and Yun, A Light-Ion Superconducting Cyclotron System for Multi-Disciplinary Users, Journal of the Korean Physical Society, Sep. 2003, 43(3):325-331.
Kim et al., Construction of 8T Magnet Test Stand for Cyclotron Studies, IEEE Transactions on Applied Superconductivity, Mar. 1993, 3(1):266-268.
Kim et al., Design Study of a Superconducting Cyclotron for Heavy Ion Therapy, Cyclotrons and Their Applications 2001, Sixteenth International Conference, May 13-17 2001, pp. 324-326.
Kim et al., Trim Coil System for the Riken Cyclotron Ring Cyclotron, Proceedings of the 1997 Particle Accelerator Conference, IEEE, Dec. 1981, vol. 3, pp. 214-235 OR 3422-3424, 1998.
Kim, An Eight Tesla Superconducting Magnet for Cyclotron Studies, Ph.D. Dissertation, Michigan State University, Department of Physics and Astronomy, 1994, 13 8 pages.
Kimstrand, Beam Modelling for Treatment Planning of Scanned Proton Beams, Digital Comprehensive Summaries of Uppsala dissertations from the Faculty of Medicine 330, Uppsala Universitet, 2008, 58 pages.
Kishida and Yano, Beam Transport System for the RIKEN SSC (II), Scientific Papers of the Institute of Physical and Chemical Research, Dec. 1981, 75(4):214-235.
Koehler et al., Range Modulators for Protons and Heavy Ions, Nuclear Instruments and Methods, 1975, vol. 131, pp. 437-440.
Koto and Tsujii, Future of Particle Thera12y, Ja12anese Journal of Cancer Clinics, 2001, 47(1):95-98 [Lang.: Japanese], English abstract (htt12://sciencelinks.j12/jeast/article/200206/000020020601A05 I I 453 .nhn).
Kraft et al., Hadrontherapy in Oncology, U. Amaldi and Larrsson, editors Elsevier Science, 1994, 161 pages.
Krevet et al., Design of a Strongly Curved Superconducting Bending Magnet for a Compact Synchrotron Light Source, Advances in Cryogenic Engineering, 1988, vol. 33, pp. 25-32.
Laisne et al., the Orsay 200 MeV Synchrocyclotron, IEEE Transactions on Nuclear Science, Apr. 1979, NS-26(2):1919-1922.
Larsson et al., Nature, 1958, 182:1222.
Larsson, Biomedical Program for the Converted 200-MeV Synchrocyclotron at the Gustaf Werner Institute, Radiation Research, 1985, 104:S310-S318.
Lawrence et al., Heavy particles in acromegaly and Cushing's Disease, in Endocrine and Norendocrine Hormone Producing Tumors (Year Book Medical Chicago, 1973, pp. 29-61.
Lawrence et al., Successful Treatment of Acromegaly: Metabolic and Clinical Studies in 145 Patients, The Journal of Clinical Endocrinology and Metabolism, Aug. 1970, 31(2), 21 pages.
Lawrence et al., Treatment of Pituitary Tumors, (Excerpta medica, Amsterdam/American Elsevier, New York, 1973, pp. 253-262.
Lawrence, Cancer, 1957, 10:795.
Lecroy et al., Viewing Probe for High Voltage Pulses, Review of Scientific Instruments USA, Dec. 1960, 31(12):1354.
Lin et al., Principles and 10 Year Experience of the Beam Monitor System at the PSI Scanned Proton Therapy Facility, Center for Proton Radiation Therapy, Paul Scherrer Institute, CH-5232, Villigen PSI, Switzerland, 2007, 21 pages.
Linfoot et al., Acromegaly, in Hormonal Proteins and Peptides, edited by C.H. Li, 1975, pp. 191-246.

(56) References Cited

OTHER PUBLICATIONS

Literature Author and Keyword Search, Feb. 14, 2005, 44 pages.
Literature Keyword Search, Jan. 24, 2005, 98 pages.
Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston et al., A capillary ion source for the cyclotron, Review Science Instruments, Feb. 1939, 10:63.
LLNL, UC Davis Team Up to Fight Cancer, Lawrence Livermore National Laboratory, Apr. 28, 2006, SF-06-04-02, Livermore, California, pp. 1-4.
Lorin, S. et al., Development of a compact proton scanning system in Uppsala with a moveable second magnet, Phys. Med. Biol, 45:1151-1163 (2000).
Mandrillon, High Energy Medical Accelerators, EPAC 90, 2nd European Particle Accelerator Conference, Jun. 12-16, 1990, 2:54-58.
Marchand et al., IBA Proton Pencil Beam Scanning: an Innovative Solution for Cancer Treatment, Proceedings of EPAC 2000, Vienna, Austria, 3 pages.
Marti et al., High Intensity Operation of a Superconducting Cyclotron, Proceedings of the I 4the International Conference, Cyclotrons and Their Applications, Oct. 1995, pp. 45-48 (Oct. 1995).
Martin, Operational Experience with Superconducting Synchrotron Magnets Proceedings of the 1987 IEEE Particle Accelerator Conference, Mar. 16-19, 1987, vol. 3 of 3: 1379-1382.
Meote et al., ETOILE Hadrontherapy Project, Review of Design Studies Proceedings of EPAC 2002, 2002, pp. 2745-2747.
Miyamoto et al., Development of the Proton Therapy System, The Hitachi Hyoron, 79(10):775-775 779 (1997) [Lang: Japanese], English abstract (http://www.hitachi.com/rev/1998/revfeb98/rev4706.htm).
Montelius et al., The Narrow Proton Beam Therapy Unit at the Svedberg Laboratory in Uppsala, ACTA Oncologica, 1991, 30:739-745.
Moser et al., Nonlinear Beam Optics with Real Fields in Compact Storage Rings, Nuclear Instruments & Methods in Physics Research/Section B, B30, Feb. 1988, No. 1, pp. 105-109.
Moyers et al., A Continuously Variable Thickness Scatterer for Proton Beams Using Self-compensating Dual Linear Wedges Loma Linda University Medical Center, Dept. of Radiation Medicine, Loma Linda, CA, Nov. 2, 1992, 21 pages.
Murphy, M. and Lin, P., Intra-fraction dose delivery timing during stereotactic radiotherapy can influence the radiobiological effect, Med. Phys., 34(2):481-484 (2007).
National Cancer Institute Funding (Senate-Se12tember 21, I 992} (w>lvw.tbomas.loc.gov/cgibin/querv/z?r102:321SE2-712 12 na2es).
Nicholson, Applications of Proton Beam Therapy, Journal of the American Society of Radiologic Technologists, May/Jun. 1996, 67(5): 439-441.
Nolen et al., The Integrated Cryogenic—Superconducting Beam Transport System Planned for MSU, Proceedings of the J21h International Conference on High-Energy Accelerators, Aug. 1983, pp. 549-551.
Non Final Office Action from U.S. Appl. No. 12/275,103 dated Feb. 1, 2011 (6 pages).
Non Final Office Action from U.S. Appl. No. 12/618,297 dated May 13, 2011 (44 pages).
Non Final Office Action from U.S. Appl. No. 12/618,297 dated May 13, 2011 (57 pages).
Norimine et al., A Design of a Rotating Gantry with Easy Steering for Proton Therapy, Proceedings of EPAC 2002, 2002, pp. 2751-2753.
Office Action and response history of U.S. Appl. No. 11/601,056 dated Aug. 24, 2009.
Office Action and response history of U.S. Appl. No. 11/601,056 dated Mar. 24, 2009.
Office Action and response history of U.S. Appl. No. 11/601,056 dated Jan. 14, 2010.
Office Action for JP2015-534721, 14 pages (dated Feb. 3, 2016) (in both Japanese and English).
Office action from Canadian Application No. 2,574,122 dated Nov. 14, 2012 (6 pages).
Office action from U.S. Appl. No. 11/948,662, dated Oct. 14, 2011 (5 pages).
Office Action with English translation from Japanese Application No. 2007-522777 dated Oct. 4, 2011 (15 pages).
Office action with English translation from Taiwanese application No. 097144546 dated Oct. 25, 2013 (27 pages).
Office action with English Translation issued in Chinese Application No. 201010581384.2 dated Nov. 10, 2011 (19 pages).
Ogino, Takashi, Heavy Charged Particle Radiotherapy-Proton Beam, Division of Radiation Oncology, National Cancer Hospital East, Kashiwa, Japan, Dec. 2003, 7 pages.
Okumura et al., Overview and Future Prospect of Proton Radiotherapy, Japanese Journal of Cancer Clinics, 1997, 43(2):209-214 [Lang.: Japanese].
Okumura et al., Proton Radiotherapy Japanese Journal of Cancer and Chemotherapy, 1993, 10. 20(14):2149-2155[Lang.: Japanese].
Ormrod, J.H., et al., The Chalk-River Superconducting Cyclotron, Proceedings of the International Conference on Cyclotrons and their applications '79, 1979 (6 pages).
Outstanding from Search Reports, Accelerator of Polarized Portons at Fermilab, 2005, 20 pages.
Paganetti et al., Proton Beam Radiotherapy—The State of the Art, Springer Verlag, Heidelberg, ISBN 3-540-00321-5, Oct. 2005, 36 pages.
Palmer and Tollestrup, Superconducting Magnet Technology for Accelerators, Annual Review of Nuclear and Particle Science, 1984, vol. 34, pp. 247-284.
Pardo, J. et al., Simulation of the performance of the CNAO facility's Beam Delivery System, PTCOG 46, Zibo, China, 17 pages (2007).
Patent Assignee and Keyword Searches for Synchrocyclotron, Jan. 25, 2005, 78 pages.
Patent Assignee Search 'Paul Scherrer Institute, Library Services at Fish & Richardson P.C., Mar. 20, 2007, 40 pages.
Patent Prior Art Search for 'Proton Therapy System', Library Services at Fish & Richardson P.C., Mar. 20, 2007, 46 pages.
Pavlovic, Beam-optics study of the gantry beam delivery system for light-ion cancer therapy, Nuclear Instruments and Methods in Physics Research, Section A, Nov. 1997, 399(2):439-454(16).
PCT International Preliminary Report on Patentability of corresponding PCT application No. PCT/US2006/044853, dated May 20, 2008 (7 pages).
PCT International Search report and Written Opinion of PCT application No. PCT/US2006/044853, dated Oct. 5, 2007 (7 pages).
Pedroni and Enge, Beam optics design of compact gantry for proton therapy Medical & Biological Engineering & Computing, May 1995, 33(3):271-277.
Pedroni and Jermann, SGSMP: Bulletin Mar. 2002 Proscan Project, Progress Report on the PROSCAN.
Pedroni et al., A Novel Gantry for Proton Therapy at the Paul Scherrer Institute, Cycloctrons and Their Applications 2001: Sixteenth International Conference. AIP Conference Proceedings, 2001, 600:13-17.
Pedroni et al., The 200-MeV proton therapy project at the Paul Scherrer Institute: Conceptual design and practical realization, Medical Physics, Jan. 1995, 22(1 ):37-53.
Pedroni, Accelerators for Charged Particle Therapy: Performance Criteria from the User Point of View, Cyclotrons and their Applications, Proceedings of the 13th International Conference, Jul. 6-10, 1992, pp. 226-233.
Pedroni, E. et al., Cancer Therapy with 200 MEV Protons at PSI. Development of a Fast Beam Scanning Method and Future Plans for a Hospital Based Facility, pp. 277-279 (1990).
Pedroni, Latest Developments in Proton Therapy Proceedings of EPAC 2000, pp. 240-244, 2000.
Pedroni, Status of Proton Therapy: results and future trends, Paul Scherrer Institute, Division of Radiation Medicine, 1994, 5 pages.

(56) References Cited

OTHER PUBLICATIONS

Peggs et al., A Survey of Hadron Therapy Accelerator Technologies, Particle Accelerator Conference, Jun. 25-29 2008, 7 pages.
Potts et al., MPWP6-Therapy III: Treatment Aids and Techniques Medical Physics, Sep./Oct. 1988, 15(5):798.
Pourrahimi et al., Powder Metallurgy Processed Nb3Sn(Ta) Wire for High Field NMR magnets, IEEE Transactions on Applied Superconductivity, Jun. 1995, 5(2):1603-1606.
Prieels et al., The IBA State-of-the-Art Proton Therapy System, Performances and Recent Results, Application of Accelerators in Research and industry—Sixteenth Int'l Conj, American Institute of Physics, Nov. 1-5, 2000, 576:857-860.
Program Chart (Oct. 7, 2006-Oct. 11, 2016), 8 pages.
Rabin et al., Compact Designs for Comprehensive Proton Beam Clinical Facilities, Nuclear Instruments & Methods in Physics Research, Apr. 1989, Section B, vol. 40-41, Part II, pp. 1335-1339.
Rainwater, James, Status of the Nevis Synchrocyclotron Modification, AIP Conference Proceedings No. 9, 1972 (14 pages).
Renner et al., "Preliminary Results of a Raster Scanning Beam Delivery System", IEEE, 1989, 3 pages.
Research & Development Magazine, Proton Therapy Center Nearing Completion, Aug. 1999, 41(9):2 pages (www.rdmag.com).
Resmini Design Characteristics of the K=800 Superconducting Cyclotron at M.S.U., Cyclotron Laboratory, Michigan State University, East Lansing, Michigan 48824, IEEE Transaction on Nuclear Science, vol. NS-26, No. 2, Apr. 1979, 8 pages.
Response to Chinese Office action dated Jan. 25, 2010 in Chinese application No. 200680051421.0, filed Jun. 24, 2010 (34 pages).
Response to European Communication issued in European application No. 13774886.9 dated Jun. 12, 2015, filed on Dec. 9, 2015 (26 pages).
Response to European Communication issued in European application No. 13783422.2 dated Jun. 12, 2015, filed on Dec. 8, 2015 (19 pages).
Response to European Communication dated Jun. 12, 2015 in European application No. 13774886.9 filed on Dec. 6, 2015 (26 pages).
Response to European Communication dated Apr. 20, 2010, from European application No. 06838033.6, filed Nov. 2, 2010 (13 pages).
Response to examination search report filed in European Application No. 05776532.3 dated Dec. 20, 2011 (14 pages).
Response to Non Final Office Action dated Feb. 1, 2011 in U.S. Appl. No. 12/275,103, filed May 2, 2011 (13 pages).
Response with English translation to Chinese Office action filed in Chinese Application No. 200880125832.9 dated Dec. 16, 2013 (12 pages).
Response with English translation to Chinese Office Action from Chinese application No. 200880125832.9 dated Sep. 22, 2011, filed on Apr. 9, 2012 (23 pages).
Response with English translation to Japanese Office action filed Mar. 1, 2012 in Japanese Application No. 2007-522777 (14 pages).
Response with English translation to office action dated Oct. 25, 2013 in Taiwanese Application No. 097144546, filed on Mar. 28, 2014 (34 pages).
RetroSearch Berkeley 88-Inch Cyclotron 'RF' or 'Frequency Control', Jan. 21, 2005, 36 pages.
RetroSearch Berkeley 88-Inch Cyclotron, Jan. 24, 2005, 170 pages.
RetroSearch Bernard Gottschalk, Cyclotron, Beams, Compensated Upstream Modulator, Compensated Scatter, Jan. 21, 2005, 20 pages.
RetroSearch Cyclotron with 'RF' or 'Frequency Control', Jan. 21, 2005, 49 pages.
RetroSearch Gottschalk, Bernard, Harvard Cyclotron Wheel, Jan. 21, 2005, 20 pages.
RetroSearch Loma Linda University Beam Compensation, Jan. 21, 2005, 60 pages.
RetroSearch Loma Linda University, Beam Compensation Foil Wedge, Jan. 21, 2005, 15 pages.
Revised Patent Keyword Search, Jan. 25, 2005, 86 pages.
Rifuggiato et, al., Status Report of the LNS Superconducting Cyclotron Nukleonika, 2003, 48:SI31-SI34, Supplement 2.
Rode, Tevatron Cryogenic System, Proceedings of the 12th International Conference on Highenergy Accelerators, Fermilab, Aug. 11-16, 1983, pp. 529-535.
Salzburger et al., Superconducting Synchrotron Magnets Supraleitende Synchrotronmagnete, NTiS, 155 pages (Oct. 1975).
Schillo et al,. Compact Superconducting 250 MeV Proton Cyclotron for the PSI Proscan Proton Therapy Project, Cyclotrons and Their Applications 2001, Sixteenth International Conference, 2001, pp. 37-39.
Schneider et al., Nevis Synchrocyclotron Conversion Program—RF System, IEEE Transactions on Nuclear Science USA, Jun. 1969, ns 16(3): 430-433.
Schneider et al., Superconducting Cyclotrons, IEEE Transactions on Magnetics, vol. MAG-11, No. 2, Mar. 1975, New York, pp. 443-446.
Schreuder et al., The Non-orthogonal Fixed Beam Arrangement for the Second Proton Therapy Facility at the National Accelerator Centre, Application of Accelerators in Research and Industry, American Institute of Physics, Proceedings of the Fifteenth International Conference, Nov. 1998, Part Two, pp. 963-966.
Schreuder, Recent Developments in Superconducting Cyclotrons, Proceedings of the 1995 Particle Accelerator Conference, May 1-5, 1995, vol. 1, pp. 317-321.
Schubert and Blosser, Conceptual Design of a High Field Ultra-Compact Cyclotron for Nuclear Physics Research, Proceedings of the 1997 Particle Accelerator Conference, May 12-16, 1997, vol. 1, 3 pp. 1060-1062.
Schubert, Extending the Feasibility Boundary of the Isochronous Cyclotron, Dissertation submitted to Michigan State University, 1997, Abstract http://adsabs.harvard.edu/abs/1998PhDt . . . 147S.
Shelaev et al., Design Features of a Model Superconducting Synchrotron of JINR, Proceedings of the 12th International Conference on High-energy Accelerators, Aug. 11-16, 1983, pp. 416-418.
Shinji Sato et al., "Dynamic Intensity Control System with RF-knockout Slow-Extraction in the HIMAC Synchrotron-" Nuclear Instruments and Methods in Physics Research A 574, 2007, pp. 226-231.
Shintomi et. Al, Technology and Materials for the Superconducting Super Collider (SSC) Project, [Lang.: Japanese], The Iron and Steel Institute of Japan 00211575, 78(8): 1305-1313, 1992, http://ci.nii.ac.ip/naid/I I 0001493249/en/.
Single Room Proton Therapy Facility, ACCEL, Oct. 2006, 1 page.
Sisterson, Clinical use of proton and ion beams from a world-wide perspective, Nuclear Instruments and Methods in Physics Research, Section B, 1989, 40-41:1350-1353.
Sisterson, World Wide Proton Therapy Experience in 1997, The American Insitute of Physics, Applications of Accelerators in Research and Industry, Proceedings of the Fifteenth International Conference, Part Two, Nov. 1998, pp. 959-962.
Slater et al., Developing a Clinical Proton Accelerator Facility: Consortium-Assisted Technology Transfer, Conference Record of the 1991 IEEE Particle Accelerator Conference: Accelerator Science and Technology, vol. I, May 6-9, 1991, pp. 532-536.
Slater et al., Development of a Hospital-Based Proton Beam Treatment Center, International Journal of Radiation Oncology J Biology J Physics, Apr. 1988, 14(4):761-775.
Smith et al., The Northeast Proton Therapy Center at Massachusetts General Hospital Journal of Brachytherapy International, Jan. 1997, pp. 137-139.
Snyder and Marti, Central region design studies for a proposed 250 MeV proton cyclotron, Nuclear Instruments and Methods in Physics Research, Section A, 1995, vol. 355, pp. 618-623.
Soga, Progress of Particle Therapy in Japan, Application of Accelerators in Research and Industry, American Institute of Physics, Sixteenth International Conference, Nov. 2000, pp. 869-872.
Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.

(56) References Cited

OTHER PUBLICATIONS

Spiller et al., The GSI Synchrotron Facility Proposal for Acceleration of High Intensity Ion and Proton Beams Proceedings of the 2003 Particle Accelerator Conference, May 12-16, 2003, vol. 1, pp. 589-591.

Stanford et al., Method of Temperature Control in Microwave Ferroelectric Measurements, Sperry Microwave Electronics Company, Clearwater, Florida, Sep. 19, 1960, 1 page.

Superconducting Cyclotron Contract awarded by Paul Scherrer Institute (PSI), Villigen, Switzerland, http://www.accel.de/News/superconducting_cyclotron_contract.htm, Jan. 2009, 1 page.

Tadashi et al., Large superconducting super collider (SSC) in the planning and materials technology, 78(8):1305-1313, The Iron and Steel Institute of Japan 00211575, Aug. 1992.

Takada, Conceptual Design of a Proton Rotating Gantry for Cancer Therapy, Japanese Journal of Medical Physics, 1995, 15(4):270-284.

Takada, Y. "A Review of Rotating Gantries for Heavy Charged Particle Therapy," Symposium of Research Center for Charged Particle Therapy on Fundamental Development of the Charged Particle Therapy, Chiba (Japan), Nov. 13-14, 2001.

Takayama et al., Compact Cyclotron for Proton Therapy, Proceedings of the 81h Symposium on Accelerator Science and Technology, Japan, Nov. 25-27, 1991, pp. 380-382.

Teng, The Fermilab Tevatron, Coral Gables 1981, Proceedings, Gauge Theories, Massive Neutrinos, and Proton Decay, 1981, pp. 43-62.

The Davis 76-Inch Isochronous Cyclotron, Beam On: Crocker Nuclear Laboratory, University of California, 2009, 1 page.

The Journal of Practical Pharmacy, 1995, 46(1):97-103 [Japanese].

The K100 Neutron-therapy Cyclotron, National Superconducting Cyclotron Laboratory at Michigan State University (NSCL ), retrieved from: http://www.nscl.msu.edu/tech/accelerators/kl 00, Feb. 2005, 1 page.

The K250 Proton therapy Cyclotron, National Superconducting Cyclotron Laboratory at Michigan State University (NSCL), retrieved from: http://www.nscl.msu.edu/tech/accelerators/k.250.html, Feb. 2005, 2 pages.

The K250 Proton-therapy Cyclotron Photo Illustration, National Superconducting Cyclotron Laboratory at Michigan State University (NSCL), retrieved from: http://www.nscl.msu.edu/media/image/ experimental-equipment-technology /25 0 .html, Feb. 2005, 1 page.

Timmer, "The ACCEL Single Room Proton Therapy Facility" ACCEL Instruments GmbH, PTCOG 45, Oct. 2006, Houston, Texas, 18 pages.

Tobias et al., Cancer Research, 1958, 18, 121 (1958).

Tom, The Use of Compact Cyclotrons for Producing Fast Neutrons for Therapy in a Rotatable Isocentric Gantry, IEEE Transaction on Nuclear Science, Apr. 1979, 26(2):2294-2298.

Toyoda, Proton Therapy System, Sumitomo Heavy Industries, Ltd., 2000, 5 pages.

Trinks et. al., The Tritron: A Superconducting Separated-Orbit Cyclotron, Nuclear Instruments and Methods in Physics Research, Section A, 1986, vol. 244, pp. 273-282.

Tsuji, H., "Cancer Therapy Using Proton Beams: the Newest State of Affairs and Future Prospects," Isotope News, No. 9, pp. 2-7 (1992). (English Abstract).

Tsuji, The Future and Progress of Proton Beam Radiotherapy, Journal of Japanese Society for Therapeutic Radiology and Oncology, 1994, 6(2):63-76.

U.S. Appl. No. 11/870,961, filed Oct. 11, 2007, including application as filed (including pending claims).

U.S. Examiner Ephrem Alemu, U.S. Non Final Office Action in U.S. Appl. No. 11/948,359, dated Aug. 20, 2010 (12 pages).

U.S. Appl. No. 13/830,792, filed Mar. 14, 2013, including the USPTO electronic file for U.S. Appl. No. 13/830,792.

U.S. Appl. No. 13/949,459. filed Jul. 24, 2013, including the USPTO electronic file for U.S. Appl. No. 13/949,459.

U.S. Appl. No. 60/590,088, filed Jul. 21, 2004, including application as filed.

U.S. Appl. No. 60/738,404, filed Nov. 18, 2005, including application as filed.

U.S. Appl. No. 60/991,454, filed Nov. 30, 2007, including application as filed.

U.S. Appl. No. 61/676,377, filed Jul. 27, 2012, including the USPTO electronic file for U.S. Appl. No. 61/676,377.

UC Davis "Crocker Nuclear Laboratory Houses a Medium-Energy Particle Accelerator," Crocker Nuclear Laboratory, University of California (2009).

UC Davis School of Medicine, Unlikely Partners Turn Military Defense into Cancer Offense, Current Issue Summer 2008, Sacramento, California, pp. 1-2.

Uli Weber et al., "Depth Scanning For A Conformal Ion Beam Treatment Of Deep Seated Tumours-" Physics in Medicine and Biology IOP Publishing UK, vol. 45, No. 12, Dec. 2000, pp. 3627-3641.

Umegaki et al., Development of an Advanced Proton Beam Therapy System for Cancer Treatment Hitachi Hyoron, 2003, 85(9):605-608 [Lang.: Japanese], English abstract, http://www.hitachi.com/ICSFiles/afieldfile/2004/06/0 1/r2003_04_1 04.pdf or http://www.hitachi.com/rev/archive/2003/2005649_12606.html (full text) [Hitachi, 52( 4), Dec. 2003].

Umezawa et al., Beam Commissioning of the new Proton Therapy System for University of Tsukuba, Proceedings of the 2001 Particle Accelerator Conference, vol. 1, Jun. 18-22, 2001, pp. 648-650.

van Steenbergen, Superconducting Synchroton Development at BNL, Proceedings of the 8th International Conference on Hifh-Ener5'Y Accelerators CERN 1971, 1971, pp. 196-198.

van Steenbergen, The CMS, a Cold Magnet Synchrotron to Upgrade the Proton Energy Range of the BNL Facility, IEEE Transactions on Nuclear Science, Jun. 1971, 18(3):694-698.

Vandeplassche et al., 235 MeV Cyclotron for MGH's Northeast Proton Therapy Center (NPTC): Present Status, EPAC 96, Fifth European Partical Accelerator Conference, vol. 3, Jun. 10-14, 1996, pp. 2650-2652.

Verster, N.F.,: Regenerative Beam Extraction from the 150-MeV Synchrocyclotron at the Laboratoire Curie, Proceedings of Sector-Focused Cyclotrons 1959, 1959, pp. 224-229 (6 pages).

Voluntary amendment filed Apr. 18, 2011 in corresponding Chinese application No. CN200780102281.X, including English translation of claim amendments (10 pages).

Voluntary amendment filed in Canadian Application No. 2,574,122 dated Jul. 26, 2010 (16 pages).

Voluntary amendment filed in Canadian Application No. 2,574,122 dated Nov. 5, 2010 (15 pages).

Voluntary amendment filed in Canadian Application No. 2707075 dated Oct. 13, 2013 (8 pages).

Voluntary Amendment filed in Canadian Application No. 2707075 dated Oct. 18, 2013 (8 pages).

Vorobiev et al., Concepts of a Compact Achromatic Proton Gantry with a Wide Scanning Field, Nuclear Instruments and Methods in Physics Research, Section A., 1998, 406(2):307-310.

Vrenken et al., A Design of a Compact Gantry for Proton Therapy with 2D-Scanning, Nuclear Instruments and Methods in Physics Research, Section A, 1999, 426(2):618-624.

Wikipedia, Synchrotron http://en.wiki11edia.org/wiki/Synchrotron (originally visited Oct. 6, 2005, revisited Jan. 28, 2009), 7 pages.

Worldwide Patent Assignee Search, Jan. 24, 2005, 224 pages.

Worldwide Patent Keyword Search, Jan. 24, 2005, 94 pages.

Written Opinion dated Aug. 26, 2008 in PCT application No. PCT/US2007/086109 (5 pages).

Written Opinion for PCT/US2007/001628, dated Feb. 18, 2008 (11 pages).

Wu, Conceptual Design and Orbit Dynamics in a 250 MeV Superconducting Synchrocyclotron, Ph.D. Dissertation, Michigan State University, Department of Physics and Astronomy, 1990, 172 pages.

York et al., Present Status and Future Possibilities at NSCL-MSU, EP AC 94, Fourth European Particle Accelerator Conference, pp. 554-556, Jun. 1994.

(56) References Cited

OTHER PUBLICATIONS

York et al., The NSCL Coupled Cyclotron Project—Overview and Status, Proceedings of the Fifteenth International Conference on Cyclotrons and their Applications, Jun. 1998, pp. 687-691.

Yudelev et al., Hospital Based Superconducting Cyclotron for Neutron Therapy: Medical Physics Perspective, Cyclotrons and their applications 2001, 16th International Conference. American Institute of Physics Conference Proceedings, vol. 600, May 13-17, 2001, pp. 40-43.

Zherbin et al., Proton Beam Therapy at the Leningrad Synchrocyclotron (Clinicomethodological Aspects and Therapeutic Results), Aug. 1987, 32(8):17-22, (German with English abstract on pp. 21-22).

Angert, N (GSI, Darmstadt), CAS—CERN Accelerator School : 5th General Accelerator Physics Course, Jyväskylä, Finland, Sep. 7-18, 1992, pp. 619-642 (CERN-1994-001).

Second Office Action (Chinese translation) for CN201380062111.9, 10 pages (dated Apr. 5, 2017).

Second Office Action (English translation) for CN201380062111.9, 16 pages (dated Apr. 5, 2017).

\* cited by examiner

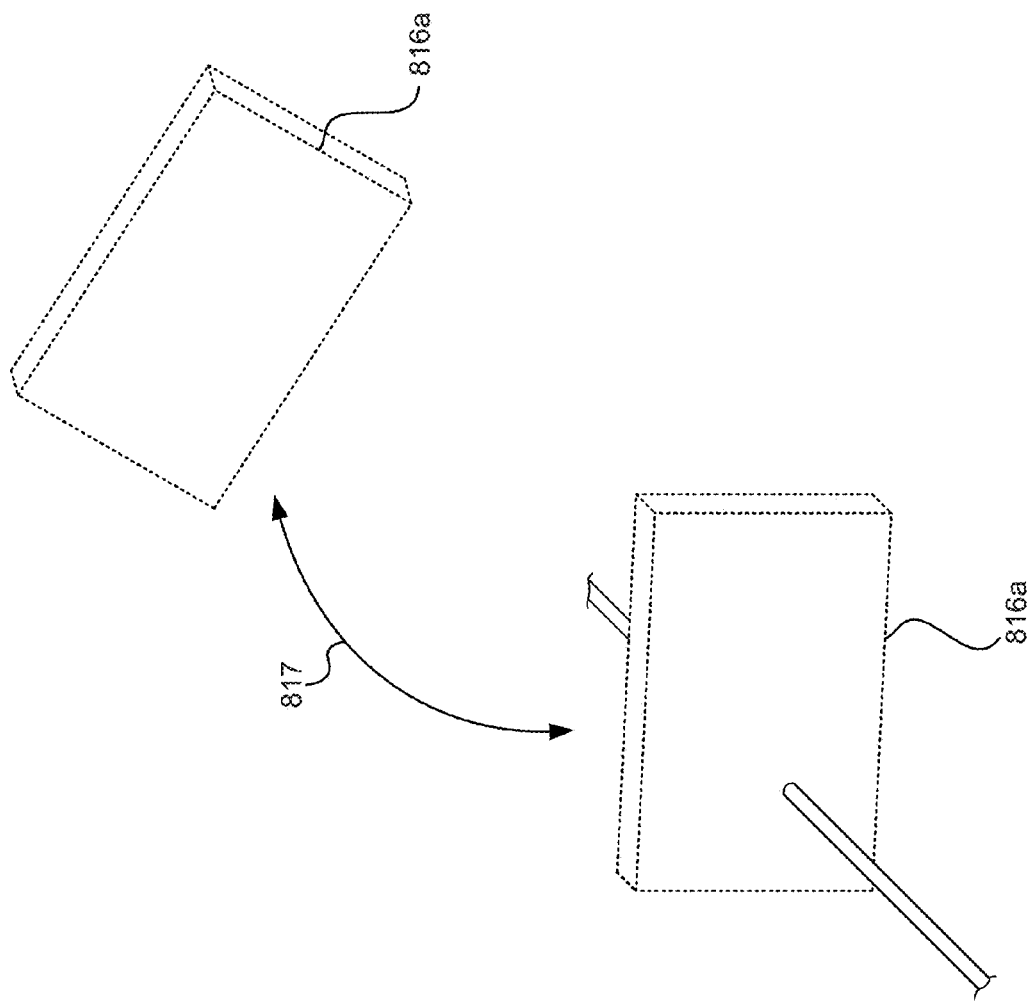

CONTROLLING INTENSITY OF A PARTICLE BEAM

CROSS-REFERENCE TO RELATED APPLICATION

Priority is hereby claimed to U.S. Provisional Application No. 61/707,466, which was filed on Sep. 28, 2012. The contents of U.S. Provisional Application No. 61/707,466 are hereby incorporated by reference into this disclosure.

TECHNICAL FIELD

This disclosure relates generally to controlling the intensity of a particle beam, such as a proton or ion beam used in a particle therapy system.

BACKGROUND

Particle therapy systems use an accelerator to generate a particle beam for treating afflictions, such as tumors. In operation, the particle beam is accelerated inside a cavity of the particle accelerator, and removed from the cavity through an extraction channel. Various elements are used to focus the particle beam and apply it to appropriate areas of a patent.

Different patients may require different doses and dose rates of particles. The dose and dose rate applied to a patient is a function of the intensity of the particle beam. Controlling the intensity of the particle beam therefore enables control over the dose and dose rate.

SUMMARY

In an example, a synchrocyclotron includes a particle source to provide pulses of ionized plasma to a cavity; a voltage source to provide a radio frequency (RF) voltage to the cavity to accelerate particles from the plasma column outwardly; and an extraction channel to receive a beam of particles from the cavity for output from the particle accelerator. The particle source is configured to control pulse widths of the ionized plasma in order to control an intensity of the beam of particles. This example synchrocyclotron may include one or more of the following features, either alone or in combination.

The particle source may be configured to activate for a period of time in response to control signal, where the particle source generates a pulse of ionized plasma when activated. The particle source may be configured to generate pulses of ionized plasma periodically. The particle beam may be output for a duration of about 0.1 µs to 100 µs (e.g., 1 µs to 10 µs). The particle beam may be output for a duration of about 0.1 µs to 100 µs (e.g., 1 µs to 10 µs) about every 2 ms. The particle source may include cathodes to provide voltage to ionize hydrogen to produce the ionized plasma. The cathodes may be unheated by an external source.

In an example, a proton therapy system includes the foregoing synchrocyclotron, and a gantry on which the synchrocyclotron is mounted, where the gantry is rotatable relative to a patient position. Protons are output essentially directly from the synchrocyclotron to the patient position.

In an example, a synchrocyclotron includes a particle source to provide pulses of ionized plasma to a cavity, where the particle source includes cathodes to provide voltage to ionize hydrogen to produce the ionized plasma; a voltage source to provide a radio frequency (RF) voltage to the cavity to accelerate particles from the plasma column outwardly; and an extraction channel to receive a beam of particles from the cavity for output from the particle accelerator. A voltage associated with the cathodes is controllable in order to control an intensity of the beam of particles. This example synchrocyclotron may include one or more of the following features, either alone or in combination.

The cathodes may be unheated by an external source. The voltage may be controllable such that increasing the voltage increases an intensity of the beam of particles and such that decreasing the voltage decreases the intensity of the beam of particles.

In an example, a proton therapy system includes the foregoing synchrocyclotron, and a gantry on which the synchrocyclotron is mounted. The gantry is rotatable relative to a patient position. Protons are output essentially directly from the synchrocyclotron to the patient position.

In an example, a synchrocyclotron includes a particle source to provide pulses of ionized plasma to a cavity, where the particle source includes cathodes to provide voltage to ionize hydrogen to produce the ionized plasma; a voltage source to provide a radio frequency (RF) voltage to the cavity to accelerate particles from the plasma column outwardly; and an extraction channel to receive a beam of particles from the cavity for output from the particle accelerator. The particle source is controllable to adjust an amount of the hydrogen between the cathodes in order to control an intensity of the beam of particles. This example synchrocyclotron may include one or more of the following features, either alone or in combination.

The cathodes may be unheated by an external source. The amount of hydrogen may be adjustable such that increasing the amount of hydrogen increases an intensity of the beam of particles and such that decreasing the amount of hydrogen decreases the intensity of the beam of particles.

In an example, a proton therapy system includes the foregoing synchrocyclotron, and a gantry on which the synchrocyclotron is mounted. The gantry is rotatable relative to a patient position. Protons are output essentially directly from the synchrocyclotron to the patient position.

In an example, a synchrocyclotron includes a particle source to provide pulses of ionized plasma to a cavity; a voltage source to provide a radio frequency (RF) voltage to the cavity to accelerate particles from the plasma column outwardly; and an extraction channel to receive a beam of particles from the cavity for output from the particle accelerator. The voltage source is controllable to control the RF voltage rate in order to control an intensity of the beam of particles. This example synchrocyclotron may include one or more of the following features, either alone or in combination.

The particle source may include cathodes to provide voltage to ionize hydrogen to produce the ionized plasma, where the cathodes are unheated by an external source. A magnitude of the RF voltage may be adjustable such that increasing the magnitude increases an intensity of the beam of particles and such that decreasing the magnitude decreases the intensity of the beam of particles.

In an example, a proton therapy system includes the foregoing synchrocyclotron, and a gantry on which the synchrocyclotron is mounted. The gantry is rotatable relative to a patient position. Protons are output essentially directly from the synchrocyclotron to the patient position.

In an example, a synchrocyclotron includes a particle source to provide pulses of ionized plasma to a cavity; a voltage source to provide a radio frequency (RF) voltage to the cavity to accelerate particles from the plasma column outwardly, where the RF voltage sweeps between a maximum frequency and a minimum frequency; and an extraction channel to receive a beam of particles from the cavity for output from the particle accelerator. The particle source is controllable to provide pulses of the ionized plasma at specific frequencies proximate to a decrease from the maximum frequency of the RF voltage to the minimum frequency of the RF voltage. This example synchrocyclotron may include one or more of the following features, either alone or in combination.

The particle accelerator may be controllable to provide pulses of the ionized plasma between 132 MHz of RF voltage and 131 MHz of RF voltage from a decrease from a maximum frequency of about 135 MHz of the RF voltage. The particle source may include cathodes to provide voltage to ionize hydrogen to produce the ionized plasma. The cathodes may be unheated by an external source.

In an example, a proton therapy system includes the foregoing synchrocyclotron, and a gantry on which the synchrocyclotron is mounted. The gantry is rotatable relative to a patient position. Protons are output essentially directly from the synchrocyclotron to the patient position.

In an example, a synchrocyclotron includes a particle source to provide pulses of ionized plasma to a cavity; a voltage source to provide a radio frequency (RF) voltage to the cavity to accelerate particles from the plasma column outwardly; and an extraction channel to receive a beam of particles from the cavity for output from the particle accelerator. The particle source is configured to selectively output pulses of the ionized plasma in order to control an intensity of the beam of particles. This example synchrocyclotron may include one or more of the following features, either alone or in combination.

The RF voltage may sweep periodically from a maximum frequency to a minimum frequency. Selectively outputting the pulses may include outputting pulses in certain ones of the RF voltage sweeps and not in others of the RF voltage sweeps. Selectively outputting the pulses may include skipping pulse output in every Nth (N>1) sweep.

The synchrocyclotron may include a controller for performing operations that include: determining the intensity of the beam of particles; and selectively outputting the pulses based on the determined intensity.

In an example, a proton therapy system includes the foregoing synchrocyclotron, and a gantry on which the synchrocyclotron is mounted. The gantry is rotatable relative to a patient position. Protons are output essentially directly from the synchrocyclotron to the patient position.

In an example, a synchrocyclotron includes a particle source to provide pulses of ionized plasma to a cavity; a voltage source to provide a radio frequency (RF) voltage to the cavity to accelerate particles from the plasma column outwardly; and an extraction channel to receive a beam of particles from the cavity for output from the particle accelerator. The voltage source is configurable to vary a slope of the RF voltage in order to control an intensity of the beam of particles.

In an example, a proton therapy system includes the foregoing synchrocyclotron, and a gantry on which the synchrocyclotron is mounted. The gantry is rotatable relative to a patient position. Protons are output essentially directly from the synchrocyclotron to the patient position.

In an example, a synchrocyclotron includes a particle source to provide pulses of ionized plasma to a cavity; a voltage source to provide a radio frequency (RF) voltage to the cavity to accelerate particles from the plasma column outwardly, where the voltage source includes a first dee and a second dee, and where at least one of the first dee and the second dee has a bias voltage applied thereto; and an extraction channel to receive a beam of particles from the cavity for output from the particle accelerator. This example synchrocyclotron may include one or more of the following features, either alone or in combination.

The first dee may have a first bias voltage applied thereto and the second dee may have a second bias voltage applied thereto, where the first bias voltage is different from the second bias voltage. The first dee may have the bias voltage applied thereto and the second dee may be electrically grounded.

In an example, a proton therapy system includes the foregoing synchrocyclotron, and a gantry on which the synchrocyclotron is mounted. The gantry is rotatable relative to a patient position. Protons are output essentially directly from the synchrocyclotron to the patient position.

In an example, a particle therapy system may include: a synchrocyclotron to output a particle beam comprised of pulses; and a scanning system for the synchrocyclotron to scan the particle beam across at least part of an irradiation target. The scanning system may be configured to scan the particle beam in two dimensions that are angled relative to (e.g., perpendicular to) a longitudinal direction of the particle beam. The particle beam makes a spot at the irradiation target. The synchrocyclotron is controllable to vary a width of the pulses so as to vary an intensity of the particle beam between different spots on the irradiation target during scanning. Implementations of the particle therapy system may include one or more of the following features, either alone or in combination.

The synchrocyclotron may include a particle source, and the particle source may be controllable to activate for periods of time to generate pulses of the particle beam that vary in width. The synchrocyclotron may be configured to sweep between low and high voltages, and a rate (or speed) of the voltage sweep may be controllable to vary a width of the pulses. The particle source may include first and second cathodes to generate a plasma stream from gas. The pulses of particle beam are extractable from the plasma stream. The gas may be a combination of hydrogen and less than 25% of a noble gas or a combination of hydrogen and less than 10% of a noble gas. The gas may be a combination of hydrogen and helium. The helium may be less than 25% of a composition of the gas. In another example, the helium may be than 10% of a composition of the gas.

The scanning system may include: a magnet to affect a direction of the particle beam to scan the particle beam in the two dimensions across at least part of the irradiation target; and a degrader to change an energy of the beam prior to output of the particle beam to the irradiation target. The degrader may be down-beam of the magnet relative to the synchrocyclotron.

The synchrocyclotron may include a voltage source to provide a radio frequency (RF) voltage to a cavity to accelerate particles from a plasma column, where the cavity has a magnetic field causing particles accelerated from the plasma column to move orbitally within the cavity; an extraction channel to receive the particles accelerated from the plasma column and to output the received particles from the cavity; and a regenerator to provide a magnetic field bump within the cavity to thereby change successive orbits of the particles accelerated from the plasma column so that, eventually, particles output to the extraction channel. The magnetic field may be between 4 Tesla (T) and 20 T (or between 6 T and 20 T) and the magnetic field bump may be at most 2 Tesla.

Two or more of the features described in this disclosure (e.g., two or more methods of controlling the intensity of a particle beam), including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices. The systems described herein, or portions thereof, may be implemented as an apparatus, method, or electronic system that may include one or more processing devices and memory to store executable instructions to implement control of the stated functions.

The details of one or more implementations are set forth in the accompanying drawings and the description below. Other features, objects, and advantages will be apparent from the description and drawings, and from the claims.

DESCRIPTION OF DRAWINGS

FIG. 24 is a perspective view of motion of a plate from the range modulator into/out of the beam path.

Like reference symbols in the various drawings indicate like elements.

DETAILED DESCRIPTION

Overview

Figure 1:
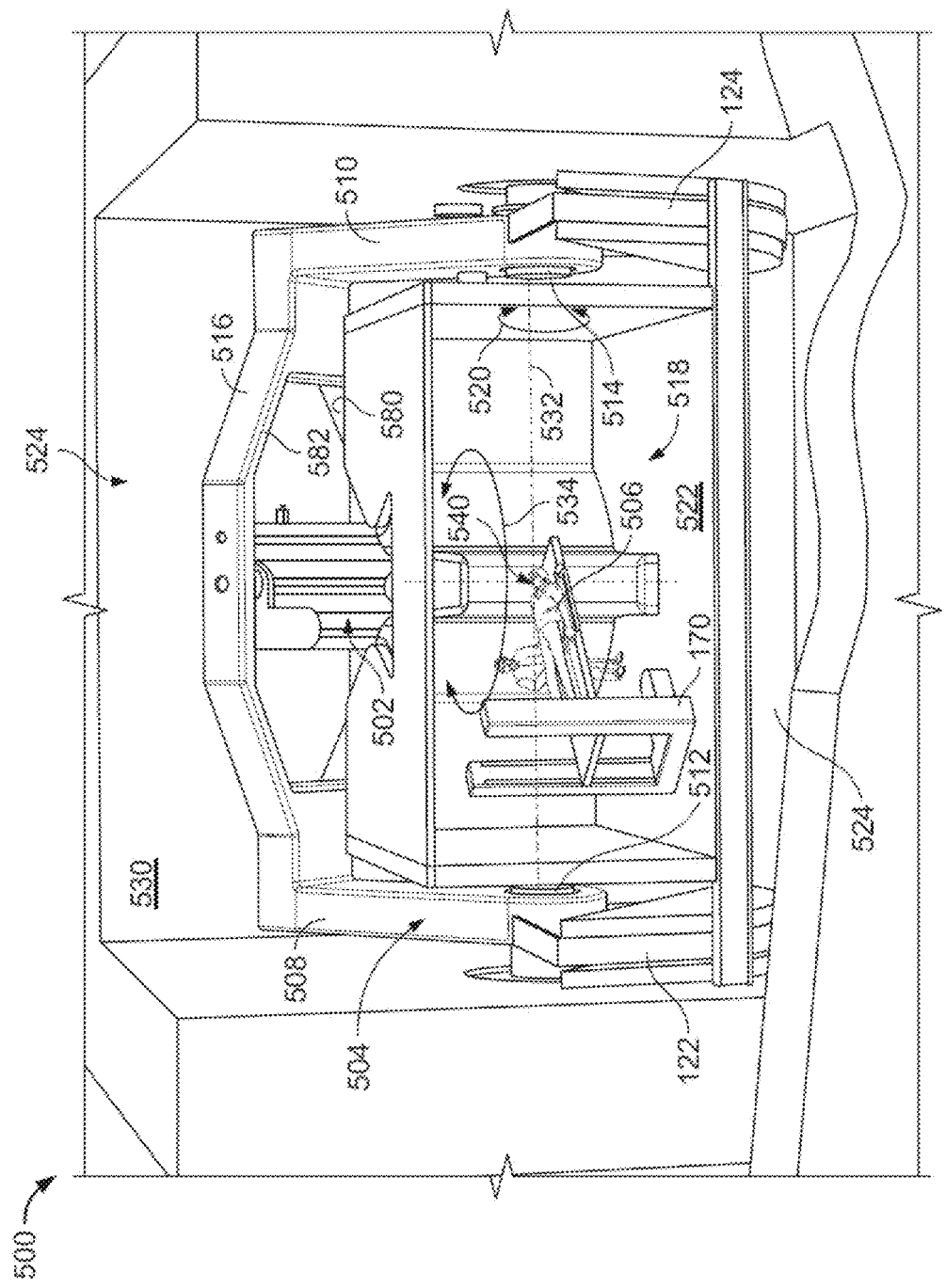
FIG. 1 is a perspective view of an example therapy system.
Figure 2:
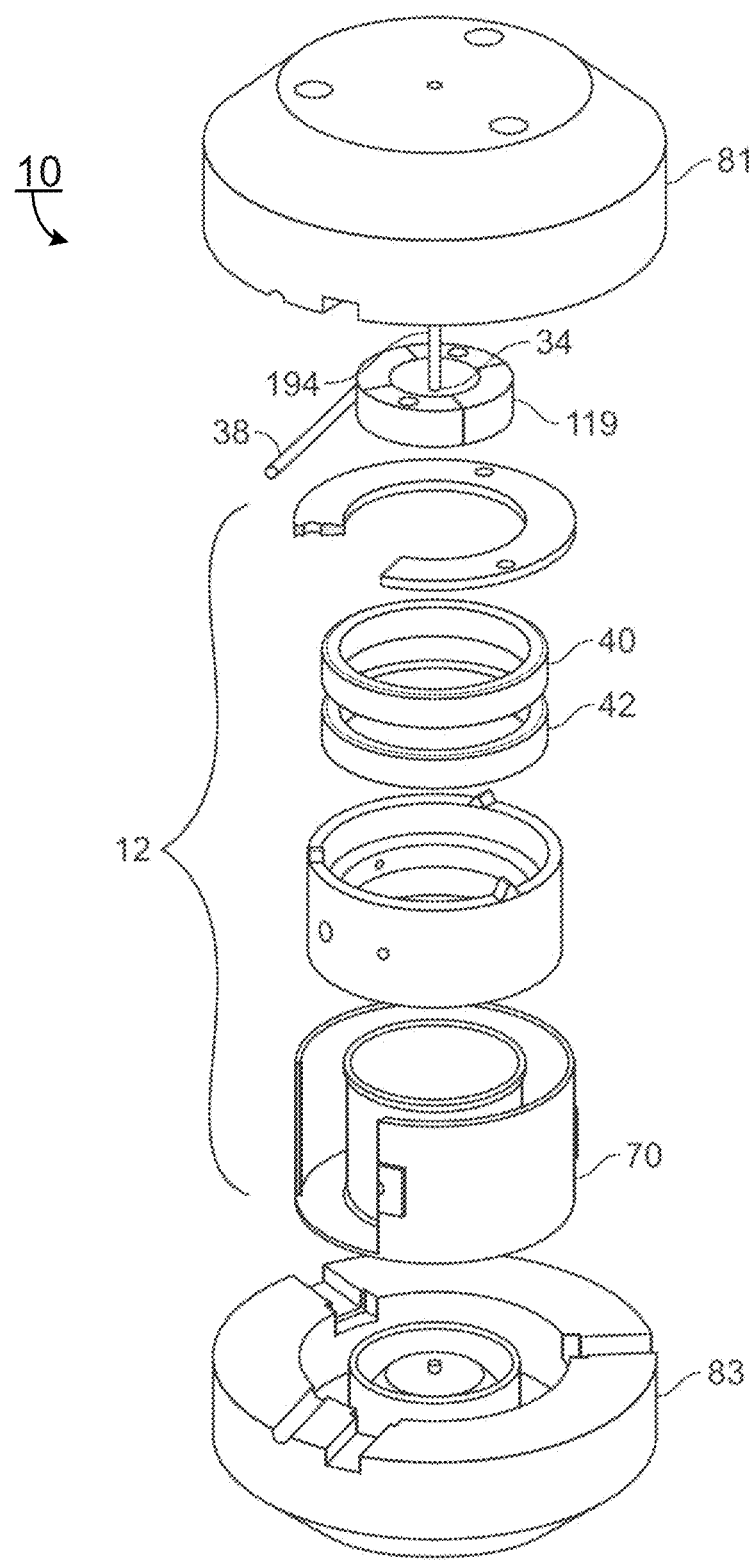
FIG. 2 is an exploded perspective view of components of an example synchrocyclotron.

Described herein is an example of a particle accelerator for use in an example system, such as a proton or ion therapy system. The system includes a particle accelerator—in this example, a synchrocyclotron—mounted on a gantry. The gantry enables the accelerator to be rotated around a patient position, as explained in more detail below. In some implementations, the gantry is steel and has two legs mounted for rotation on two respective bearings that lie on opposite sides of a patient. The particle accelerator is supported by a steel truss that is long enough to span a treatment area in which the patient lies and that is attached stably at both ends to the rotating legs of the gantry. As a result of rotation of the gantry around the patient, the particle accelerator also rotates.

In an example implementation, the particle accelerator (e.g., the synchrocyclotron) includes a cryostat that holds a superconducting coil for conducting a current that generates a magnetic field (B). In this example, the cryostat uses liquid helium (He) to maintain the coil at superconducting temperatures, e.g., 4° Kelvin (K). Magnetic yokes are adjacent (e.g., around) the cryostat, and define a cavity in which particles are accelerated. The cryostat is attached to the magnetic yokes through straps or the like.

In an example implementation, the particle accelerator includes a particle source (e.g., a Penning Ion Gauge—PIG source) to provide a plasma column to the cavity. Hydrogen gas is ionized to produce the plasma column. A voltage source provides a radio frequency (RF) voltage to the cavity to accelerate particles from the plasma column. As noted, in this example, the particle accelerator is a synchrocyclotron. Accordingly, the RF voltage is swept across a range of frequencies to account for relativistic effects on the particles (e.g., increasing particle mass) as their velocity increases during acceleration and the decreasing magnetic field produced to maintain axial focusing of the particles. The magnetic field produced by the coil causes particles accelerated from the plasma column to accelerate orbitally within the cavity. A magnetic field regenerator is positioned near the outer edge of the cavity and may be used to adjust the existing magnetic field at this location to thereby change locations of successive orbits of the particles accelerated from the plasma column so that, eventually, the particles output to an extraction channel that passes through the yokes. The extraction channel receives particles accelerated from the plasma column and outputs the received particles from the cavity. Elements both inside and outside the extraction channel shape and focus the particle beam.

A control system may be used to select the intensity of the particle beam. For example, one or more parameters or features of the particle accelerator may be controlled or otherwise adjusted to output the particle beam with the selected intensity. The selected intensity may be constant or variable. The example systems described herein use techniques to control the intensity of a particle beam, e.g., to vary the dose and dose rate of a particle beam delivered to a patient. A description of these techniques is provided below, followed by a description of an example particle therapy system in which those techniques may be implemented.

In an example technique, the intensity of the particle beam can be controlled by varying the time duration of the pulse of particle pulses extracted from the plasma column. In more detail, the RF voltage sweeps from a starting (e.g., maximum) frequency (e.g., 135 MHz) to an ending (e.g., minimum) frequency (e.g., 90 MHz). The particle source is activated for a period of time during the RF sweep to produce a plasma column. For example, in some implementations, the particle source is activated at 132 MHz for a period of time. During that time, particles are extracted from the plasma column by the electric field produced by the RF voltage. The extracted particles accelerate outwardly in orbits as the RF voltage frequency drops, keeping pace with the decreasing magnetic field and increasing relativistic mass until the particles are swept out a time (e.g., about 600 microseconds) later. Changing the duration for which the particle source is activated changes the width of the pulse of particles that is extracted from the plasma column during a frequency sweep. Increasing the pulse width causes an increase in the amount of particles extracted and thus an increase in the intensity of the particle beam. Decreasing the pulse width causes a decrease in the amount of particles extracted and thus a decrease in the intensity of the particle beam.

In another example technique, the intensity of the particle beam can be controlled by changing a voltage applied to cathodes in the particle source. In this regard, the plasma column is generated by applying a voltage to two cathodes of the particle source, and by outputting a gas, such as hydrogen ($H_2$), in the vicinity of the cathodes. The voltage applied to the cathodes ionizes the hydrogen and the background magnetic field collimates the ionized hydrogen to thereby produce the plasma column. Increasing the cathode voltage causes an increase in the amount of ions in the plasma column, and decreasing the cathode voltage causes a decrease in the amount of ions in the plasma column. When more ions are present in the plasma column, more ions can be extracted during the RF voltage sweep, thereby increasing the intensity of the particle beam. When fewer ions are present in the plasma column, fewer ions can be extracted during the RF voltage sweep, thereby decreasing the intensity of the particle beam.

In another example technique, the intensity of the particle beam can be controlled by varying the amount of hydrogen supplied to the particle source. For example, increasing the amount of hydrogen supplied to the particle source results in more opportunity for ionization in the plasma column in response to the cathode voltage. Conversely, decreasing the amount of hydrogen supplied to the particle source results in less opportunity for ionization in the plasma column in response to the cathode voltage. As noted above, when more particles are present in the plasma column, more particles are extracted during the RF voltage sweep, thereby increasing the intensity of the particle beam. When fewer particles are present in the plasma column, fewer particles are extracted during the RF voltage sweep, thereby decreasing the intensity of the particle beam.

In another example technique, the intensity of the particle beam can be controlled by varying the magnitude of the RF voltage used to extract particles from the plasma column. For example, increasing the magnitude of the RF voltage causes more particles to be extracted from the plasma column. Conversely, decreasing the magnitude of the RF voltage causes fewer particles to be extracted from the plasma column. When more particles are extracted, the particle beam increases in intensity. Conversely, when fewer particles are extracted, the particle beam decreases in intensity.

In another example technique, the intensity of the particle beam can be controlled by varying the starting time during the frequency sweep at which the particle source is activated and, thus, during which particles are extracted. More specifically, there is a finite window during the frequency sweep during which particles can be extracted from the plasma column. In an example implementation, the frequency sweeps from about 135 MHz to about 90 MHz at a substantially constant rate. In this example, particles can be extracted at about the beginning of the downward slope between starting and ending frequencies, e.g., between 132 MHz and 131 MHz respectively, and the particle source can be activated for a period of time, e.g., for about 0.1 µs to 100 µs (or e.g., 1 µs to 10 µs up to about 40 µs). Changing the frequency at which the particle source is activated affects the amount of particles that are extracted from the particle beam and therefore the intensity of the particle beam.

In another example technique, pulse blanking may be used to control the intensity of the particle beam. In this regard, the frequency sweep is repeated a number of times per second (e.g., 500 times/second). The particle source could be activated for each frequency sweep (e.g., every 2 ms). Pulse blanking reduces the number of particles extracted from the particle beam by not activating the particle source during every frequency sweep. To achieve maximum beam intensity, the particle source may be activated every frequency sweep. To reduce beam intensity, the particle source may be activated less frequently, e.g., every second, third, hundredth, etc. sweep.

In another example technique, the intensity of the particle beam can be controlled by applying a DC bias voltage to one or more dees used to apply the RF voltage to the particle accelerator cavity. In this regard, the particle accelerator includes an active dee plate (or simply "dee") that is a hollow metal structure having two semicircular surfaces that enclose a cavity in which the protons are accelerated during their rotation around the space enclosed by the magnet structure. The active dee is driven by a RF signal that is applied at the end of a radio-frequency transmission line to impart an electric field into the cavity. The RF field is made to vary in time as the accelerated particle beam increases in distance from the geometric center. A "dummy" dee comprises a rectangular metal wall with a slot for the beam that is spaced near to the exposed rim of the active dee. In some implementations, the dummy dee is grounded to the vacuum chamber and magnet yoke.

Applying RF voltage in the presence of a strong magnetic field can cause multi-pactoring, which can reduce the magnitude of the RF field and, in some cases, cause an electrical short. To reduce the amount of multi-pactoring, and thereby maintain the RF field, DC bias voltage may be applied to the active dee and, in some implementations, also to the dummy dee. In some implementations, the differential bias voltage between the active dee and dummy dee may be controlled to reduce multi-pactoring and thereby increase beam intensity. For example, in some implementations, there may be a 50% differential between the DC bias voltage on the active dee and dummy dee (e.g., a −1.9 KV DC bias voltage may be applied to the dummy dee and a −1.5 KV DC bias voltage may be applied to the active dee).

In another example technique, the intensity of the particle beam can be controlled by controlling the rate at which the RF voltage is swept (e.g., the slope of the decrease). By decreasing the slope, it is possible to increase the amount of time during which particles can be extracted from the plasma column. As a result, more particles can be extracted, thereby increasing the intensity of the particle beam. The converse is also true, e.g., by increasing the slope, the amount of time during which particles can be extracted from the plasma column can be decreased, which can result in a decrease in particle beam intensity.

The foregoing techniques for controlling the intensity of a particle beam in a particle accelerator may be used individually in a single particle accelerator, or any two or more of those techniques may be used in any appropriate combination in a single particle accelerator. The techniques are not limited to use with a particle therapy system, but rather may be used in any appropriate particle accelerator.

An example of a particle therapy system in which the foregoing techniques may be used is provided below.

Example Particle Therapy System

Referring to FIG. 1, a charged particle radiation therapy system 500 includes a beam-producing particle accelerator 502 having a weight and size small enough to permit it to be mounted on a rotating gantry 504 with its output directed straight (that is, essentially directly) from the accelerator housing toward a patient 506.

In some implementations, the steel gantry has two legs 508, 510 mounted for rotation on two respective bearings 512, 514 that lie on opposite sides of the patient. The accelerator is supported by a steel truss 516 that is long enough to span a treatment area 518 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 520 of less than 360 degrees, e.g., about 180 degrees, to permit a floor 522 to extend from a wall of the vault 524 that houses the therapy system into the patient treatment area. The limited rotation range of the gantry also reduces the required thickness of some of the walls, which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space.

The horizontal rotational axis 532 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 534 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a very high magnetic field superconducting electromagnetic structure. Because the bend radius of a charged particle of a given kinetic energy is reduced in direct proportion to an increase in the magnetic field applied to it, the very high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

Superconducting materials lose their superconducting properties in the presence of very high magnetic fields. High performance superconducting wire windings are used to allow very high magnetic fields to be achieved.

Superconducting materials typically need to be cooled to low temperatures for their superconducting properties to be realized. In some examples described here, cryo-coolers are used to bring the superconducting coil windings to temperatures near absolute zero. Using cryo-coolers can reduce complexity and cost.

The synchrocyclotron is supported on the gantry so that the beam is generated directly in line with the patient. The gantry permits rotation of the cyclotron about a horizontal rotational axis that contains a point (isocenter 540) within, or near, the patient. The split truss that is parallel to the rotational axis, supports the cyclotron on both sides.

Because the rotational range of the gantry is limited, a patient support area can be accommodated in a wide area around the isocenter. Because the floor can be extended broadly around the isocenter, a patient support table can be positioned to move relative to and to rotate about a vertical axis 542 through the isocenter so that, by a combination of gantry rotation and table motion and rotation, any angle of beam direction into any part of the patient can be achieved. The two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 1, the superconducting synchrocyclotron 502 operates with a peak magnetic field in a pole gap of the synchrocyclotron of 8.8 Tesla. The synchrocyclotron produces a beam of protons having an energy of 250 MeV. In other implementations the field strength could be in the range of 6 to 20 Tesla or 4 to 20 Tesla and the proton energy could be in the range of 150 to 300 MeV The radiation therapy system described in this example is used for proton radiation therapy, but the same principles and details can be applied in analogous systems for use in heavy ion (ion) treatment systems.

As shown in FIGS. 2, 3, 4, 5, and 6, an example synchrocyclotron 10 (e.g., 502 in FIG. 1) includes a magnet system 12 that contains an particle source 90, a radiofrequency drive system 91, and a beam extraction system 38. The magnetic field established by the magnet system has a shape appropriate to maintain focus of a contained proton beam using a combination of a split pair of annular superconducting coils 40, 42 and a pair of shaped ferromagnetic (e.g., low carbon steel) pole faces 44, 46.

Figure 7:
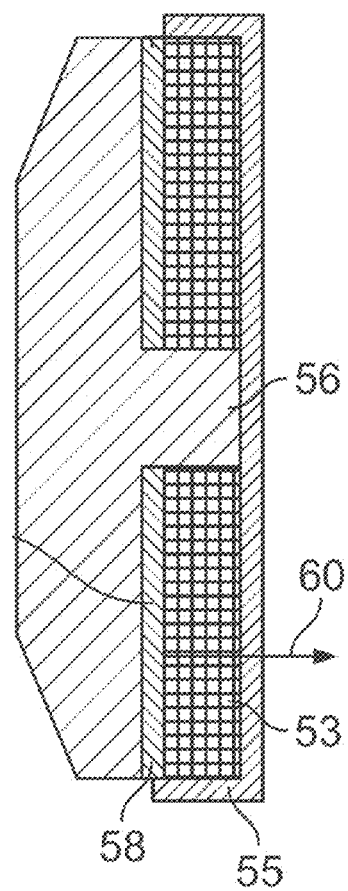
FIG. 7 is a cross-sectional view of a portion of an example reverse bobbin and windings.
Figure 8:
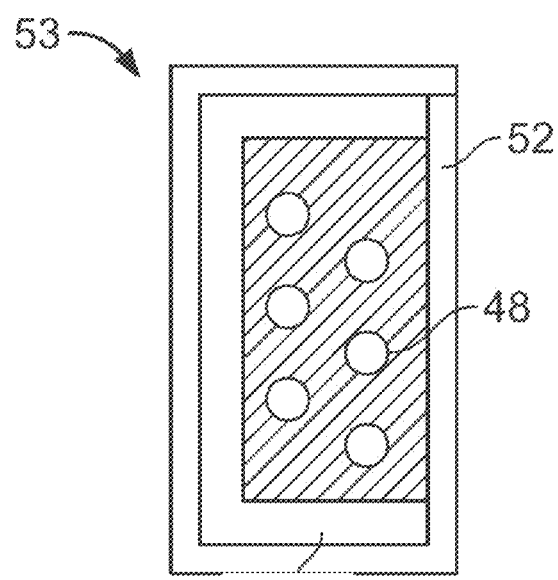
FIG. 8 is a cross sectional view of an example cable-in-channel composite conductor.

The two superconducting magnet coils are centered on a common axis 47 and are spaced apart along the axis. As shown in FIGS. 7 and 8, the coils are formed by of $Nb_3Sn$-based superconducting 0.8 mm diameter strands 48 (that initially comprise a niobium-tin core surrounded by a copper sheath) deployed in a twisted cable-in-channel conductor geometry. After seven individual strands are cabled together, they are heated to cause a reaction that forms the final (brittle) superconducting material of the wire. After the material has been reacted, the wires are soldered into the copper channel (outer dimensions 3.18×2.54 mm and inner dimensions 2.08×2.08 mm) and covered with insulation 52 (in this example, a woven fiberglass material). The copper channel containing the wires 53 is then wound in a coil having a rectangular cross-section of 8.55 cm×19.02 cm, having 26 layers and 49 turns per layer. The wound coil is then vacuum impregnated with an epoxy compound. The finished coils are mounted on an annular stainless steel reverse bobbin 56. Heater blankets 55 are placed at intervals in the layers of the windings to protect the assembly in the event of a magnet quench.

The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at a temperature of 100 degrees Kelvin can achieve this.

Figure 5:
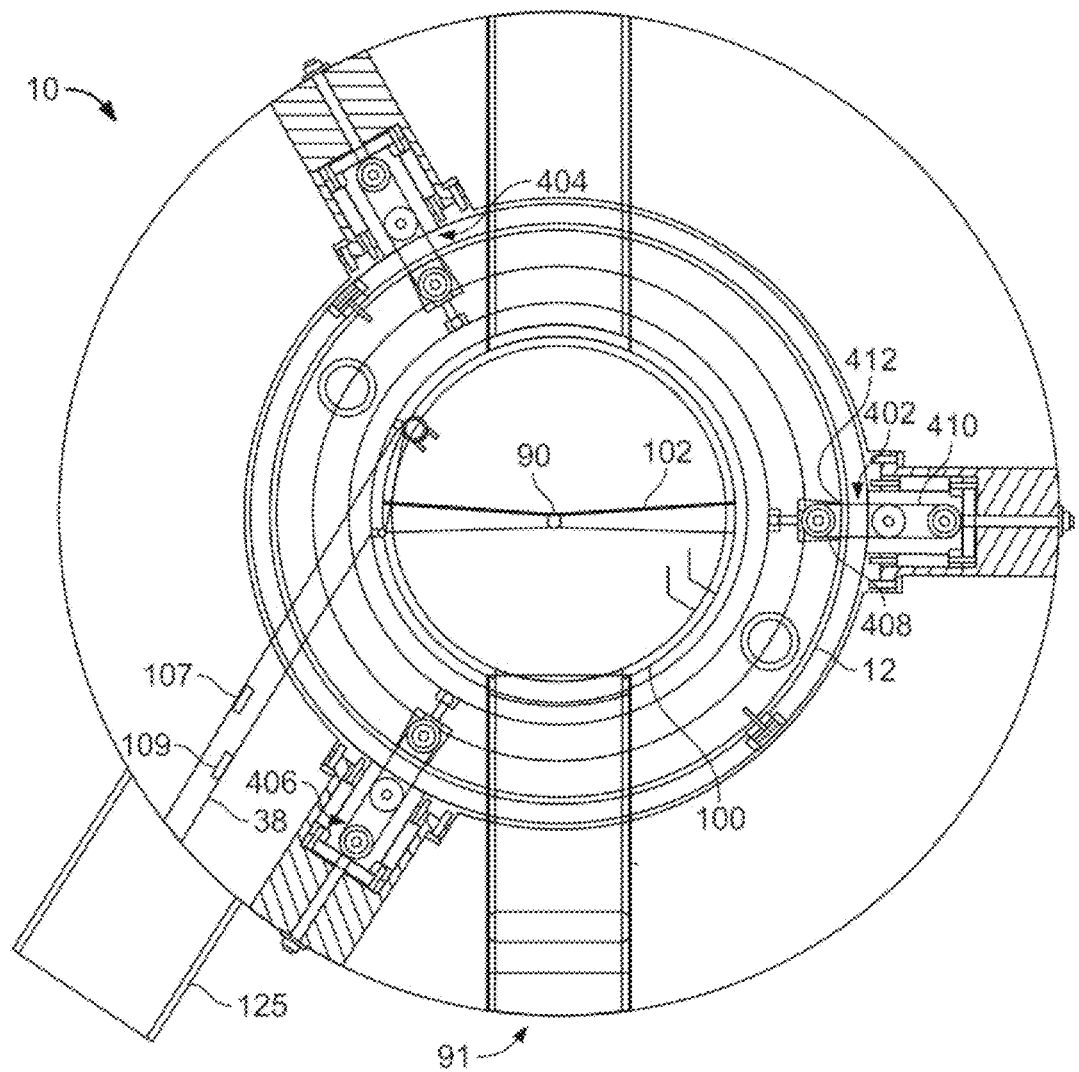
Figure 6:
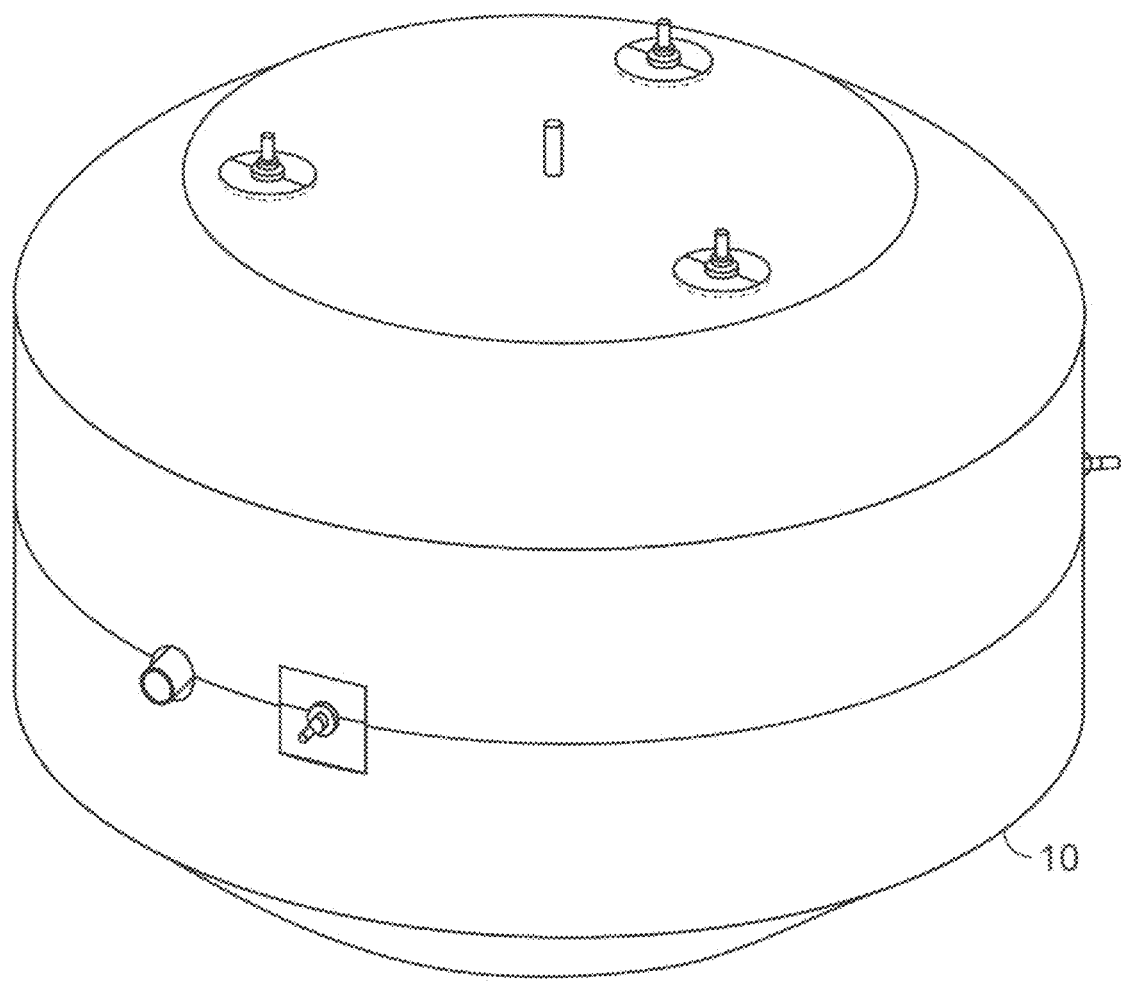
FIG. 6 is a perspective view of an example synchrocyclotron.

The geometry of the coil is maintained by mounting the coils in a reverse rectangular bobbin 56 to exert a restorative force 60 that works against the distorting force produced when the coils are energized. As shown in FIG. 5, the coil position is maintained relative to the magnet yoke and cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally the links act to reduce dynamic forces imparted on the coil as the gantry accelerates and decelerates when its position is changed. Each warm-to-cold support includes one S2 fiberglass link and one carbon fiber link. The carbon fiber link is supported across pins between the warm yoke and an intermediate temperature (50-70 K), and the S2 fiberglass link 408 is supported across the intermediate temperature pin and a pin attached to the cold mass. Each link is 5 cm long (pin center to pin center) and is 17 mm wide. The link thickness is 9 mm. Each pin is made of high strength stainless steel and is 40 mm in diameter.

Figure 3:
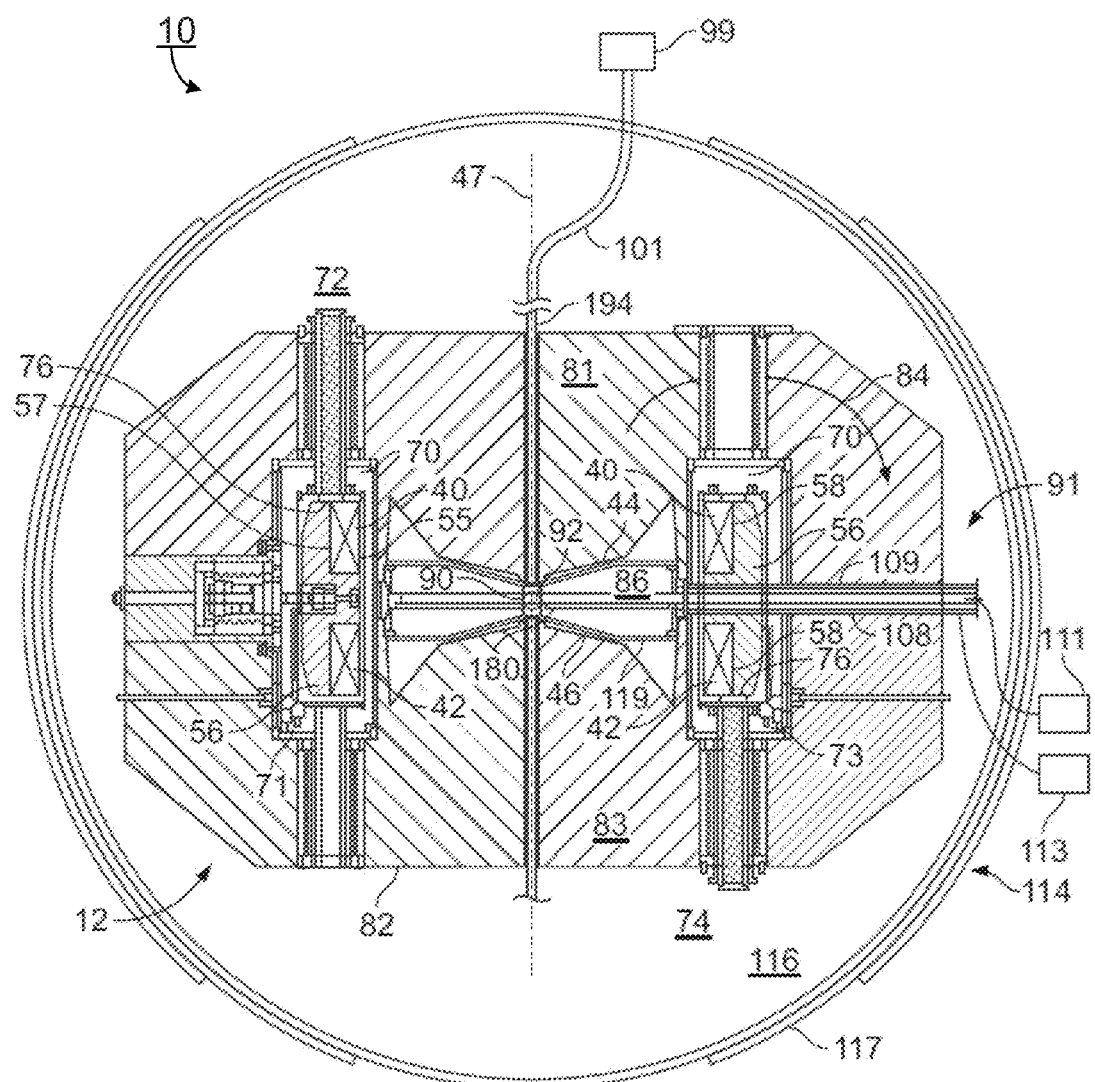
FIGS. 3, 4, and 5 are cross-sectional views of an example synchrocyclotron.
Figure 4:
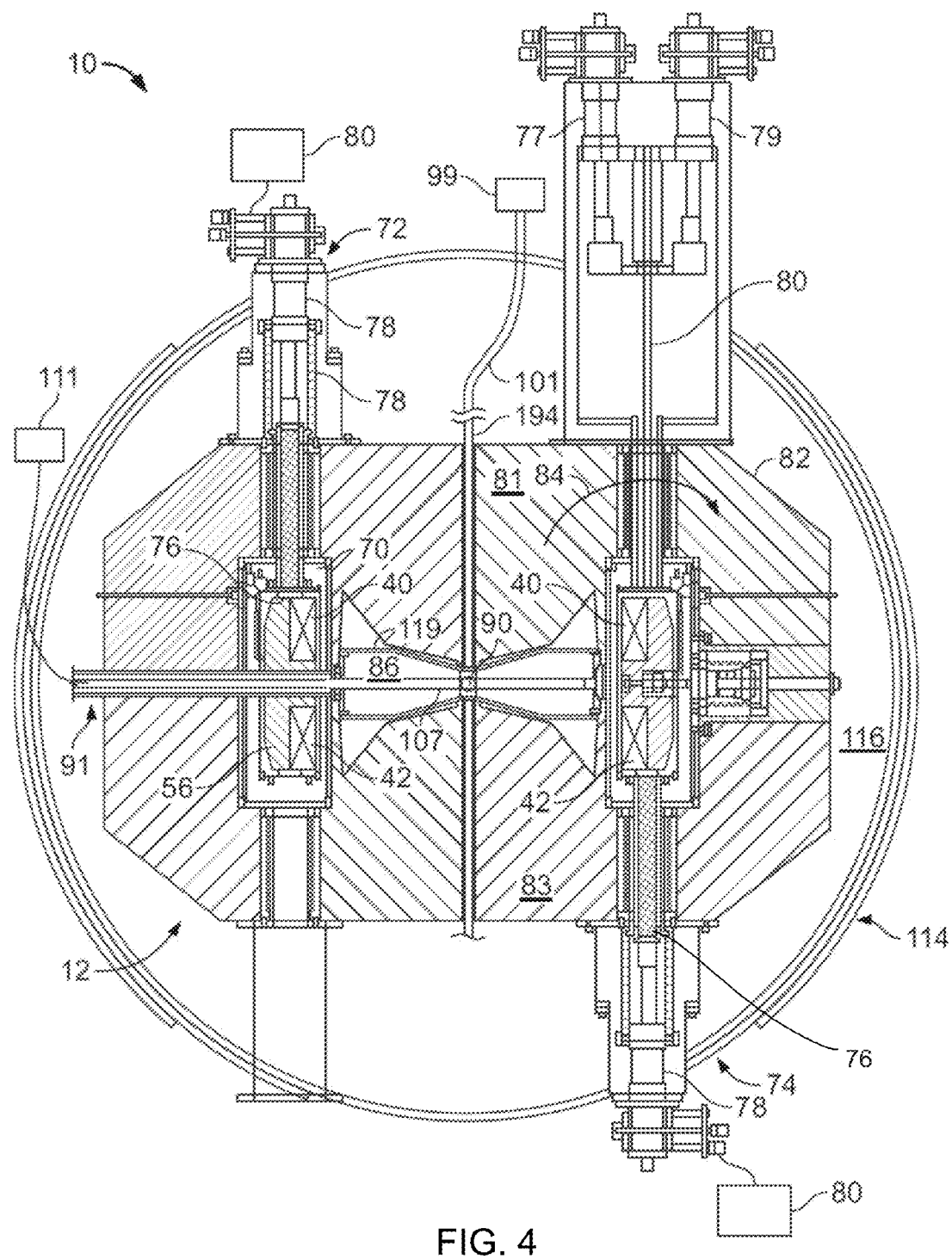

Referring to FIG. 3, the field strength profile as a function of radius is determined largely by choice of coil geometry and pole face shape; the pole faces 44, 46 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 70 that provides a free space around the coil structure, except at a limited set of support points 71, 73. In an alternate version (FIG. 4) the outer wall of the cryostat may be made of low carbon steel to provide an additional return flux path for the magnetic field.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. The cryo-cooler heads are supplied with compressed Helium from a compressor. The single-stage Gifford-McMahon cryo-cooler is arranged to cool high temperature (e.g., 50-70 degrees Kelvin) leads that supply current to the superconducting windings.

In some implementations, the temperature near absolute zero is achieved and maintained using two Gifford-McMahon cryo-coolers 72, 74 that are arranged at different positions on the coil assembly. Each cryo-cooler has a cold end 76 in contact with the coil assembly. The cryo-cooler heads 78 are supplied with compressed Helium from a compressor 80. Two other Gifford-McMahon cryo-coolers 77, 79 are arranged to cool high temperature (e.g., 60-80 degrees Kelvin) leads that supply current to the superconducting windings.

Figure 9:
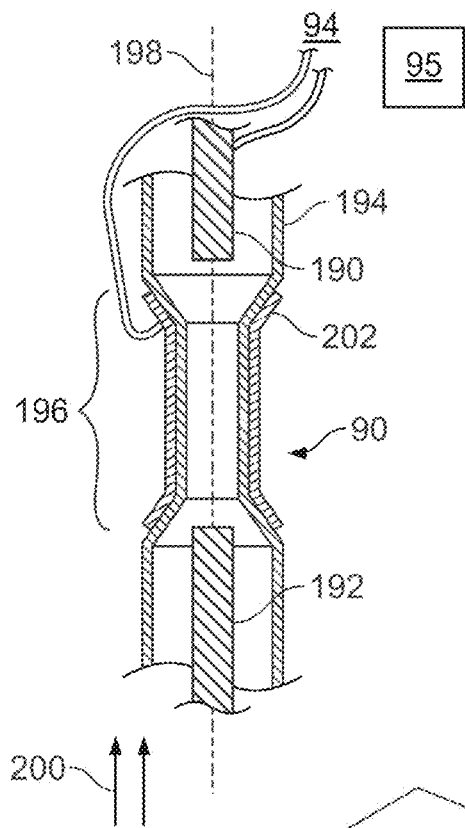
FIG. 9 is a cross-sectional view of an example particle source.

The coil assembly and cryostatic chambers are mounted within and fully enclosed by two halves 81, 83 of a pillbox-shaped magnet yoke 82. In this example, the inner diameter of the coil assembly is about 74.6 cm. The iron yoke 82 provides a path for the return magnetic field flux 84 and magnetically shields the volume 86 between the pole faces 44, 46 to prevent external magnetic influences from perturbing the shape of the magnetic field within that volume. The yoke also serves to decrease the stray magnetic field in the vicinity of the accelerator. In some implementations, the synchrocyclotron may have an active return system to reduce stray magnetic fields. An example of an active return system is described in U.S. patent application Ser. No. 13/907,601, which was filed on May 31, 2013, the contents of which are incorporated herein by reference. In the active return system, the relatively large magnetic yokes described herein are replaced by smaller magnetic structures, referred to as pole pieces. Superconducting coils run current opposite to the main coils described herein in order to provide magnetic return and thereby reduce stray magnetic fields As shown in FIGS. 3 and 9, the synchrocyclotron includes a particle source 90 of a Penning ion gauge geometry located near the geometric center 92 of the magnet structure 82. The particle source may be as described below, or the particle source may be of the type described in U.S. patent application Ser. No. 11/948,662 incorporated herein by reference.

Particle source 90 is fed from a supply 99 of hydrogen through a gas line 101 and tube 194 that delivers gaseous hydrogen. Electric cables 94 carry an electric current from a current source 95 to stimulate electron discharge from cathodes 192, 190 that are aligned with the magnetic field, 200.

In this example, the discharged electrons ionize the gas exiting through a small hole from tube 194 to create a supply of positive ions (protons) for acceleration by one semicircular (dee-shaped) radio-frequency plate 100 that spans half of the space enclosed by the magnet structure and one dummy dee plate 102. In the case of an interrupted particle source (an example of which is described in U.S. patent application Ser. No. 11/948,662), all (or a substantial part) of the tube containing plasma is removed at the acceleration region, thereby allowing ions to be more rapidly accelerated in a relatively high magnetic field.

Figure 10:
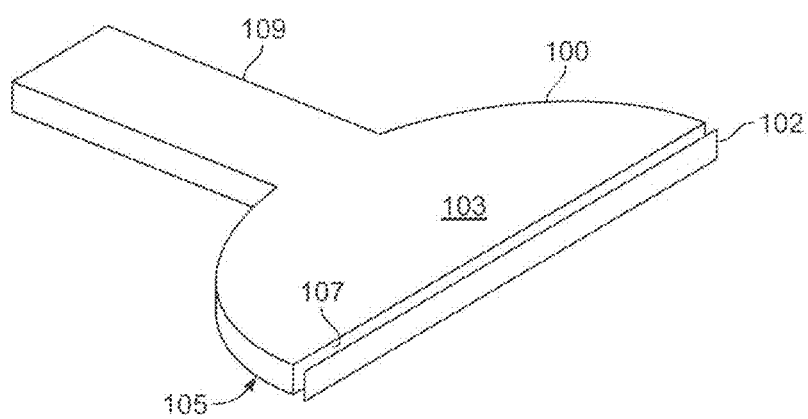
FIG. 10 is a perspective view of an example dee plate and an example dummy dee.

As shown in FIG. 10, the dee plate 100 is a hollow metal structure that has two semicircular surfaces 103, 105 that enclose a space 107 in which the protons are accelerated during half of their rotation around the space enclosed by the magnet structure. A duct 109 opening into the space 107 extends through the yoke to an external location from which a vacuum pump 111 can be attached to evacuate the space 107 and the rest of the space within a vacuum chamber 119 in which the acceleration takes place. The dummy dee 102 comprises a rectangular metal ring that is spaced near to the exposed rim of the dee plate. The dummy dee is grounded to the vacuum chamber and magnet yoke. The dee plate 100 is driven by a radio-frequency signal that is applied at the end of a radio-frequency transmission line to impart an electric field in the space 107. The radio frequency electric field is made to vary in time as the accelerated particle beam increases in distance from the geometric center. The radio frequency electric field may be controlled in the manner described in U.S. patent application Ser. No. 11/948,359, entitled "Matching A Resonant Frequency Of A Resonant Cavity To A Frequency Of An Input Voltage", the contents of which are incorporated herein by reference.

For the beam emerging from the centrally located particle source to clear the particle source structure as it begins to spiral outward, a large voltage difference is required across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This is done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles is accelerated during each meshing of the blades of the rotating condenser.

The vacuum chamber 119 in which the acceleration occurs is a generally cylindrical container that is thinner in the center and thicker at the rim. The vacuum chamber encloses the RF plates and the particle source and is evacuated by the vacuum pump 111. Maintaining a high vacuum insures that accelerating ions are not lost to collisions with gas molecules and enables the RF voltage to be kept at a higher level without arcing to ground.

Protons traverse a generally spiral orbital path beginning at the particle source. In half of each loop of the spiral path, the protons gain energy as they pass through the RF electric field in space 107. As the ions gain energy, the radius of the central orbit of each successive loop of their spiral path is larger than the prior loop until the loop radius reaches the maximum radius of the pole face. At that location a magnetic and electric field perturbation directs ions into an area where the magnetic field rapidly decreases, and the ions depart the area of the high magnetic field and are directed through an evacuated tube 38, referred to herein as the extraction channel, to exit the yoke of the cyclotron. A magnetic regenerator may be used to change the magnetic field perturbation to direct the ions. The ions exiting the cyclotron will tend to disperse as they enter the area of markedly decreased magnetic field that exists in the room around the cyclotron. Beam shaping elements 107, 109 in the extraction channel 38 redirect the ions so that they stay in a straight beam of limited spatial extent.

The magnetic field within the pole gap needs to have certain properties to maintain the beam within the evacuated chamber as it accelerates. The magnetic field index n, which is shown below, $$n=-(r/B)dB/dr,$$

should be kept positive to maintain this "weak" focusing. Here r is the radius of the beam and B is the magnetic field. Additionally, in some implementations, the field index needs to be maintained below 0.2, because at this value the periodicity of radial oscillations and vertical oscillations of the beam coincide in a $v_r=2 v_z$ resonance. The betatron frequencies are defined by $v_r=(1-n)^{1/2}$ and $v_z=n^{1/2}$. The ferromagnetic pole face is designed to shape the magnetic field generated by the coils so that the field index n is maintained positive and less than 0.2 in the smallest diameter consistent with a 250 MeV beam in the given magnetic field.

As the beam exits the extraction channel it is passed through a beam formation system 125 (FIG. 5) that can be programmably controlled to create a desired combination of scanning, scattering, and/or range modulation for the beam. Beam formation system 125 may be used in conjunction with an inner gantry 601 (FIG. 14) to direct a beam to the patient.

During operation, the plates absorb energy from the applied radio frequency field as a result of conductive resistance along the surfaces of the plates. This energy appears as heat and is removed from the plates using water cooling lines 108 that release the heat in a heat exchanger 113 (FIG. 3).

Stray magnetic fields exiting from the cyclotron are limited by both the pillbox magnet yoke (which also serves as a shield) and a separate magnetic shield 114. The separate magnetic shield includes of a layer 117 of ferromagnetic material (e.g., steel or iron) that encloses the pillbox yoke, separated by a space 116. This configuration that includes a sandwich of a yoke, a space, and a shield achieves adequate shielding for a given leakage magnetic field at lower weight.

As mentioned, the gantry allows the synchrocyclotron to be rotated about the horizontal rotational axis 532. The truss structure 516 has two generally parallel spans 580, 582. The synchrocyclotron is cradled between the spans about midway between the legs. The gantry is balanced for rotation about the bearings using counterweights 122, 124 mounted on ends of the legs opposite the truss.

The gantry is driven to rotate by an electric motor mounted to one or both of the gantry legs and connected to the bearing housings by drive gears. The rotational position of the gantry is derived from signals provided by shaft angle encoders incorporated into the gantry drive motors and the drive gears.

At the location at which the ion beam exits the cyclotron, the beam formation system 125 acts on the ion beam to give it properties suitable for patient treatment. For example, the beam may be spread and its depth of penetration varied to provide uniform radiation across a given target volume. The beam formation system can include passive scattering elements as well as active scanning elements.

All of the active systems of the synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), may be controlled by appropriate synchrocyclotron control electronics (not shown), which may include, e.g., one or more computers programmed with appropriate programs to effect control.

The control of the gantry, the patient support, the active beam shaping elements, and the synchrocyclotron to perform a therapy session is achieved by appropriate therapy control electronics (not shown).

Figure 11:
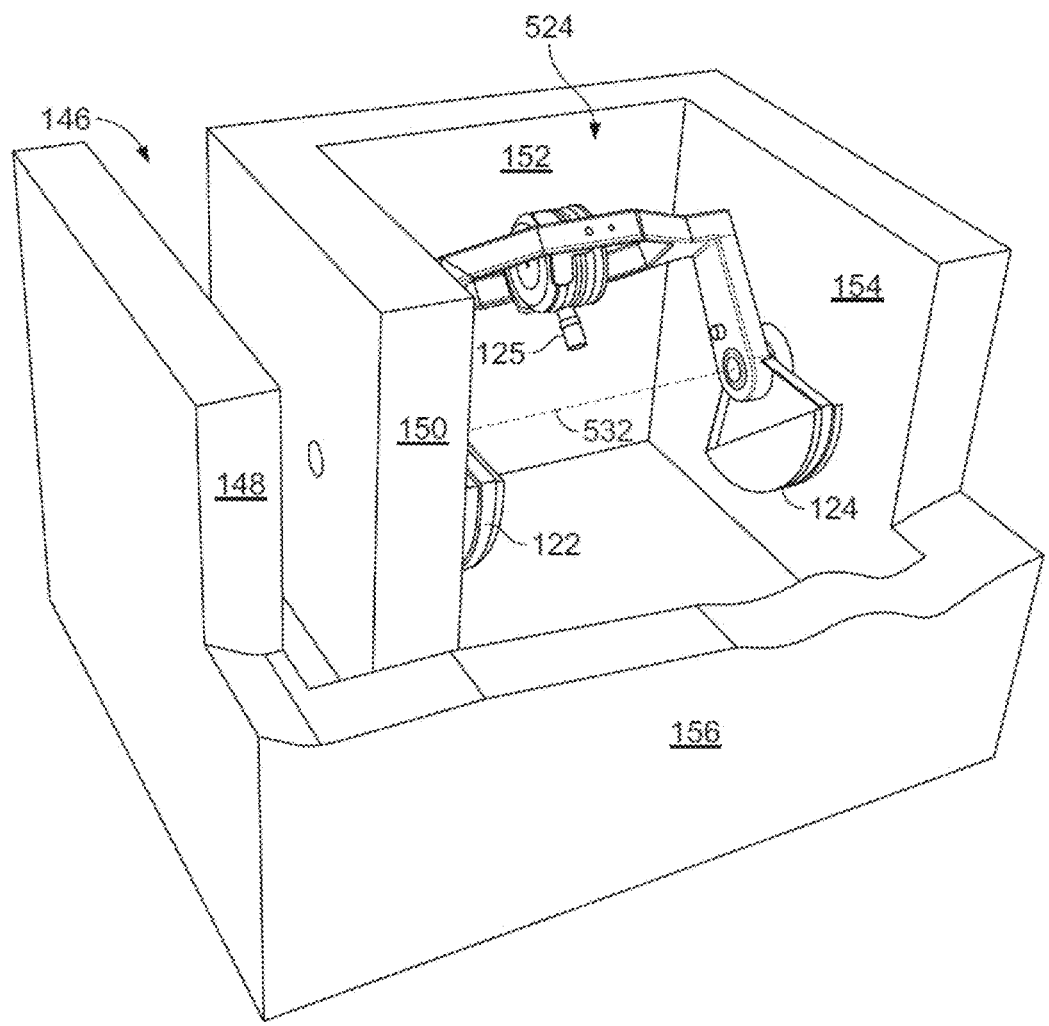
FIG. 11 is a perspective view of an example vault.
Figure 12:
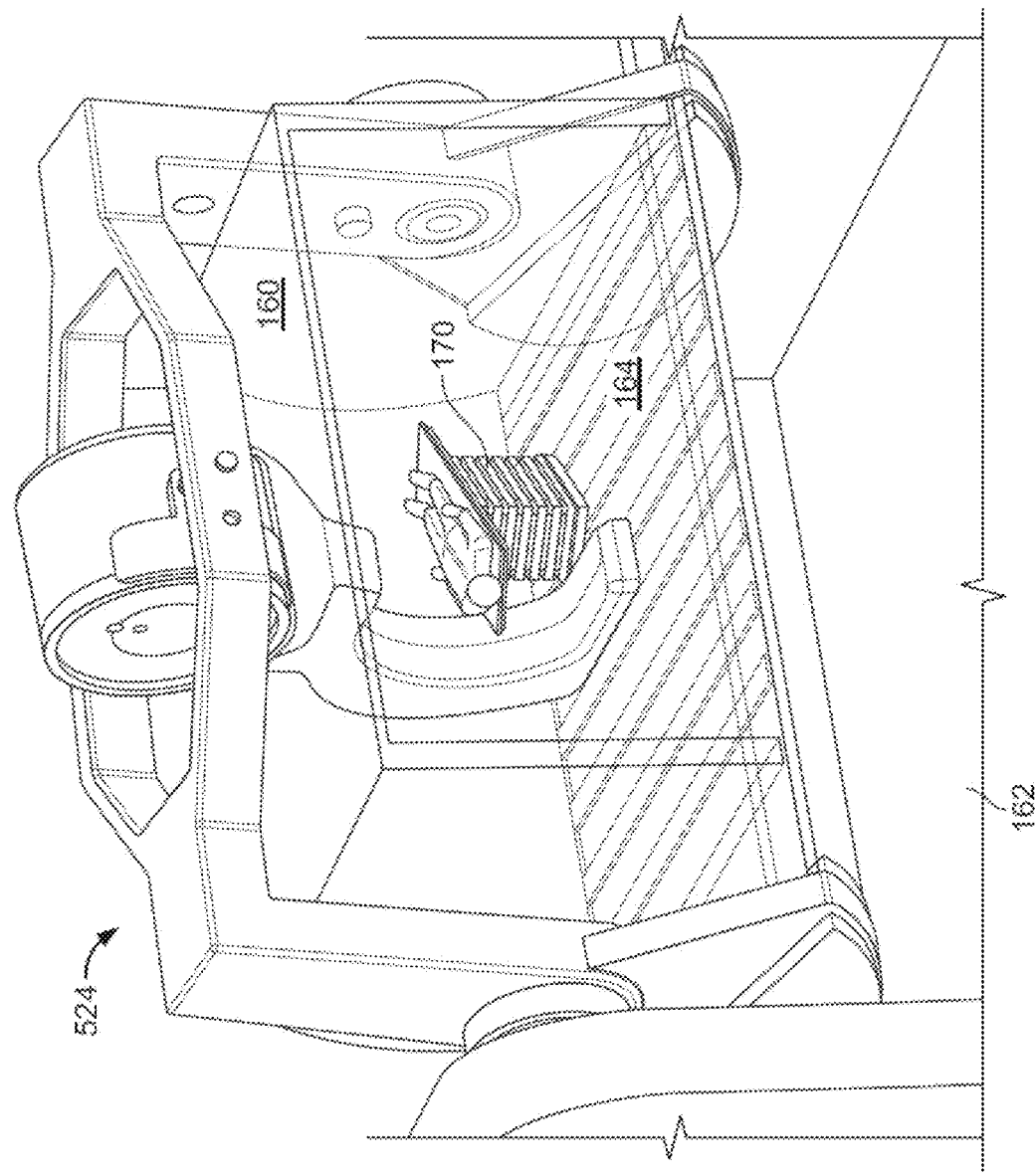
FIG. 12 is a perspective view of an example treatment room with a vault.

As shown in FIGS. 1, 11, and 12, the gantry bearings are supported by the walls of a cyclotron vault 524. The gantry enables the cyclotron to be swung through a range 520 of 180 degrees (or more) including positions above, to the side of, and below the patient. The vault is tall enough to clear the gantry at the top and bottom extremes of its motion. A maze 146 sided by walls 148, 150 provides an entry and exit route for therapists and patients. Because at least one wall 152 is not in line with the proton beam directly from the cyclotron, it can be made relatively thin and still perform its shielding function. The other three side walls 154, 156, 150/148 of the room, which may need to be more heavily shielded, can be buried within an earthen hill (not shown). The required thickness of walls 154, 156, and 158 can be reduced, because the earth can itself provide some of the needed shielding.

Figure 13:
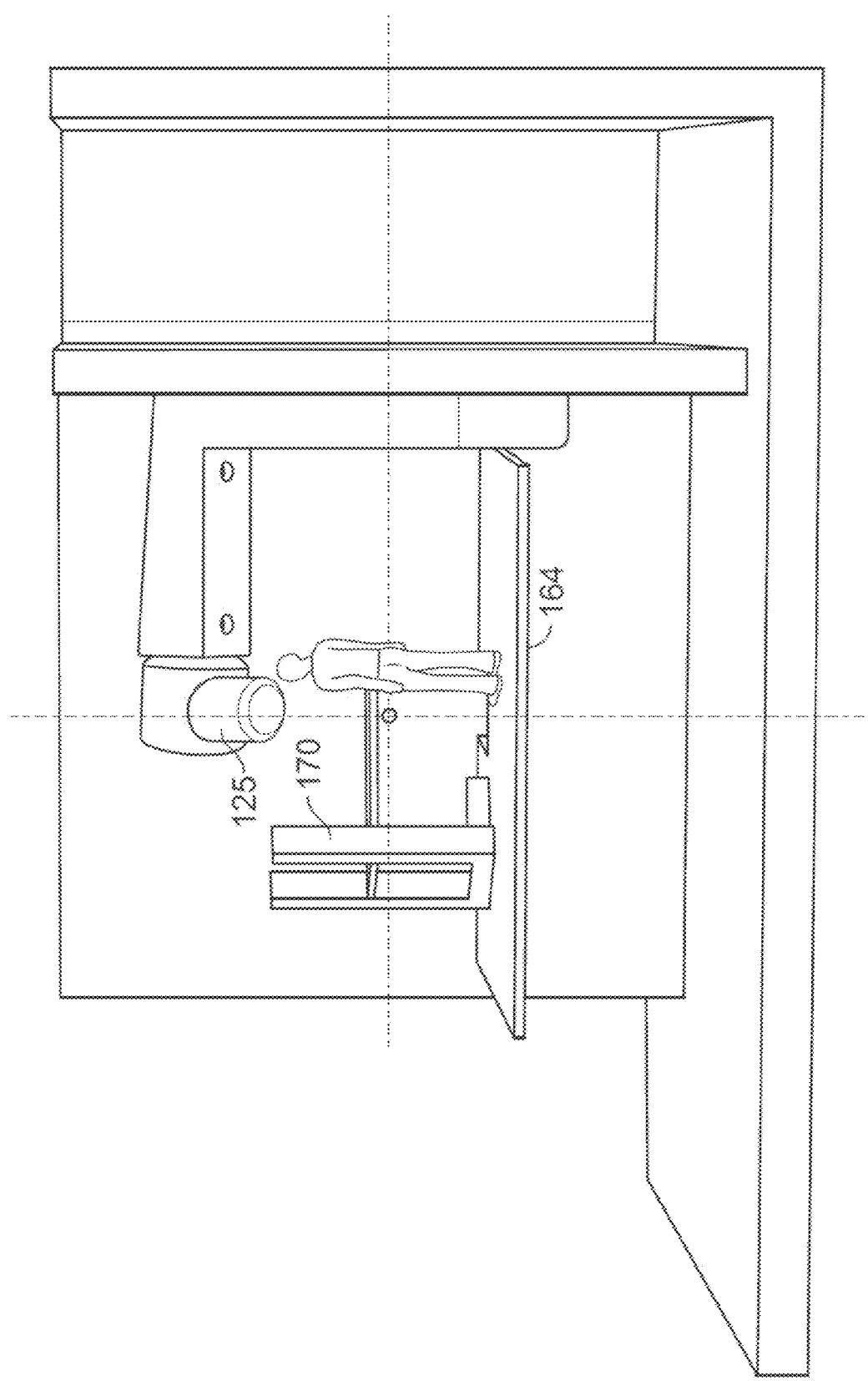
FIG. 13 shows a patient positioned relative to an example particle accelerator.

Referring to FIGS. 12 and 13, for safety and aesthetic reasons, a therapy room 160 may be constructed within the vault. The therapy room is cantilevered from walls 154, 156, 150 and the base 162 of the containing room into the space between the gantry legs in a manner that clears the swinging gantry and also maximizes the extent of the floor space 164 of the therapy room. Periodic servicing of the accelerator can be accomplished in the space below the raised floor. When the accelerator is rotated to the down position on the gantry, full access to the accelerator is possible in a space separate from the treatment area. Power supplies, cooling equipment, vacuum pumps and other support equipment can be located under the raised floor in this separate space. Within the treatment room, the patient support 170 can be mounted in a variety of ways that permit the support to be raised and lowered and the patient to be rotated and moved to a variety of positions and orientations.

Figure 14:
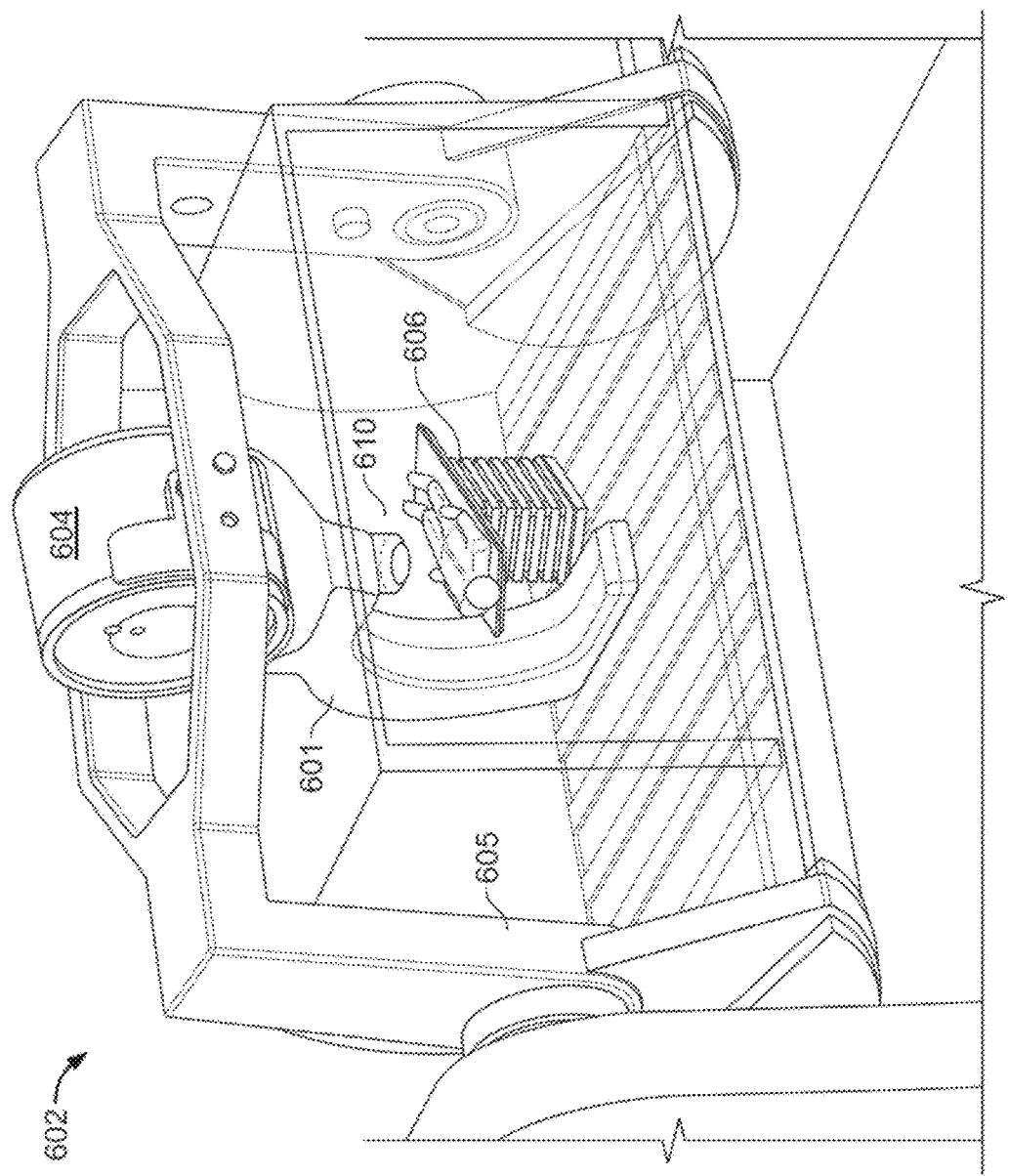
FIG. 14 shows a patient positioned within an example inner gantry in a treatment room.

In system 602 of FIG. 14, a beam-producing particle accelerator of the type described herein, in this case synchrocyclotron 604, is mounted on rotating gantry 605. Rotating gantry 605 is of the type described herein, and can angularly rotate around patient support 606. This feature enables synchrocyclotron 604 to provide a particle beam directly to the patient from various angles. For example, as in FIG. 14, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

Further details regarding an example implementation of the foregoing system may be found in U.S. Pat. No. 7,728,311, filed on Nov. 16, 2006 and entitled "Charged Particle Radiation Therapy", and in U.S. patent application Ser. No. 12/275,103, filed on Nov. 20, 2008 and entitled "Inner Gantry". The contents of U.S. Pat. No. 7,728,311 and in U.S. patent application Ser. No. 12/275,103 are hereby incorporated by reference into this disclosure.

In some implementations, the synchrocyclotron may be a variable-energy device, such as that described in U.S. patent application Ser. No. 13/916,401, filed on Jun. 12, 2013, the contents of which are incorporated by reference into this disclosure.

Example Implementations

Referring to FIG. 3, particle source 90 is deployed near to the magnetic center of synchrocyclotron 10 so that particles are present at the synchrocyclotron mid-plane, where they can be acted upon by the RF voltage field. As noted above, the particle source may have a Penning ion gauge (PIG) geometry. In the PIG geometry, two high voltage cathodes are placed about opposite each other so that they are aligned linearly. For example, one cathode may be on one side of the acceleration region and one cathode may be on the other side of the acceleration region and in line with the magnetic field lines. A gas tube 101 extends toward the acceleration region proximate to the particle source. When a relatively small amount of a gas (e.g., hydrogen/$H_2$) occupies a region in the tube between the cathodes, a plasma column may be formed from the gas by applying a voltage to the cathodes. The applied voltage causes electrons to stream along the magnetic field lines, essentially parallel to the tube walls, and to ionize gas molecules that are concentrated inside the tube. The background magnetic field prevents scattering of the ionized gas particles and creates a plasma column between the cathodes.

In some implementations, the gas in gas tube 101 may include a mixture of hydrogen and one or more other gases. For example, the mixture may contain hydrogen and one or more of the noble gases, e.g., helium, neon, argon, krypton, xenon and/or radon (although the mixture is not limited to use with the noble gases). In some implementations, the mixture may be a mixture of hydrogen and helium. For example, the mixture may contain about 75% or more of hydrogen and about 25% or less of helium (with possible trace gases included). In another example, the mixture may contain about 90% or more of hydrogen and about 10% or less of helium (with possible trace gases included). In examples, the hydrogen/helium mixture may be any of the following: >95%/<5%, >90%/<10%, >85%/<15%, >80%/<20%, >75%/<20%, and so forth.

Possible advantages of using a noble (or other) gas in combination with hydrogen in the particle source may include: increased beam intensity, increased cathode longevity, and increased consistency of beam output.

Figure 15:
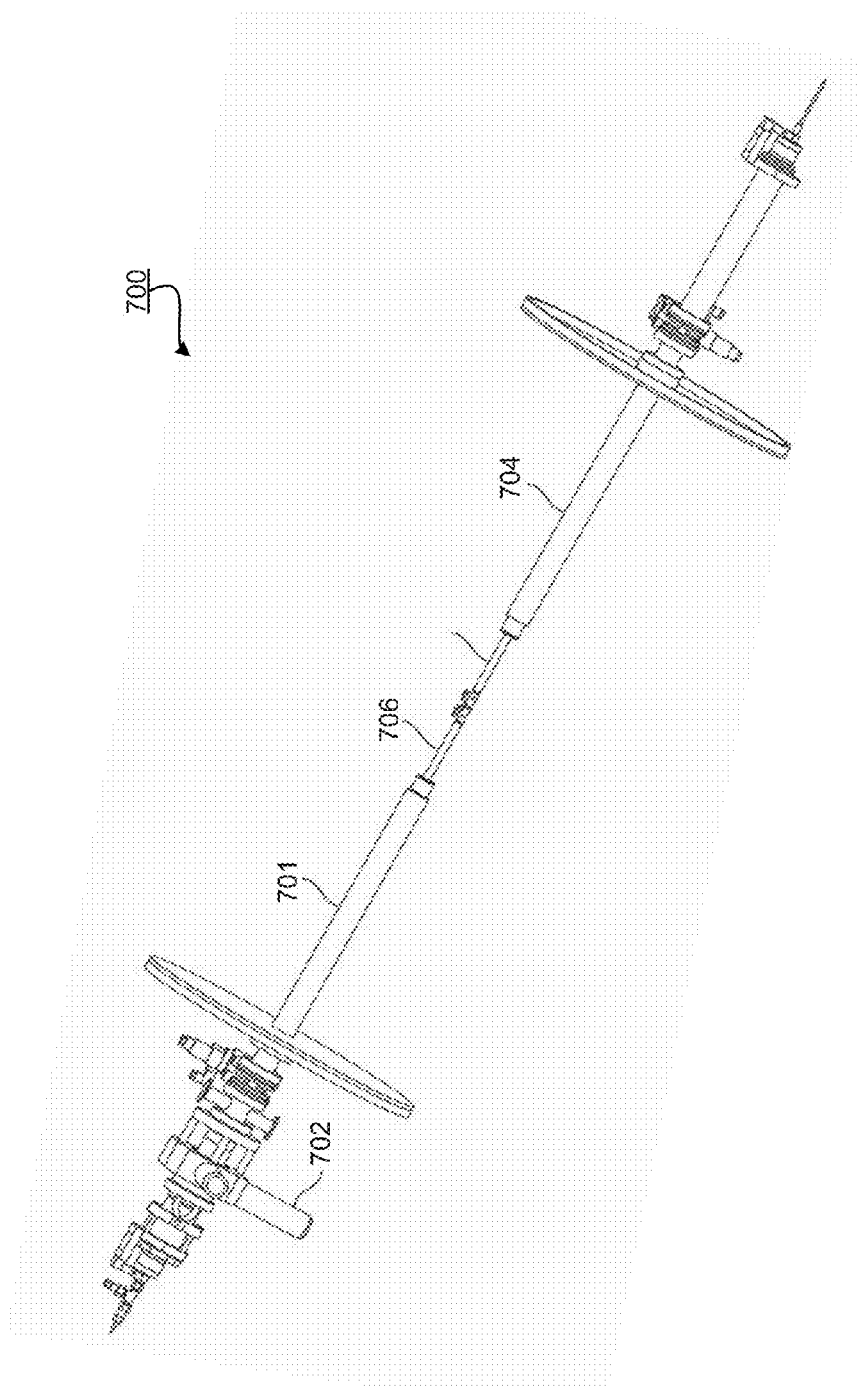
FIGS. 15 and 16 show an example particle source.
Figure 16:
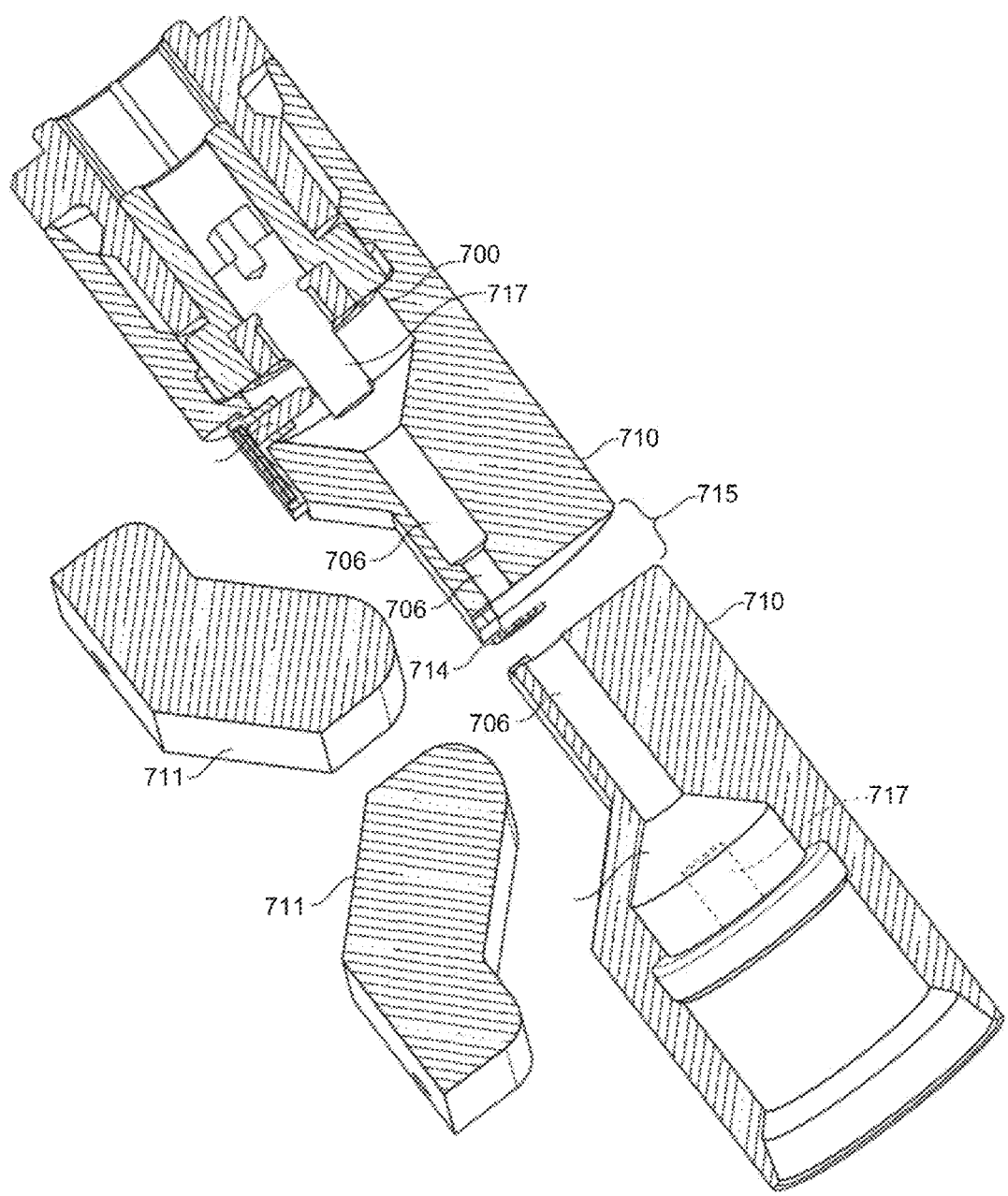

An example of a PIG geometry particle source 700 that may be used in synchrocyclotron 10 is shown in FIGS. 15 and 16. Referring to FIG. 15, particle source 700 includes an emitter side 701 containing a gas feed 702 for receiving gas (e.g., hydrogen ($H_2$), and a reflector side 704. A housing, or tube, 706 holds the gas. FIG. 16 shows particle source 700 passing through dummy dee 710 and adjacent to active (RF) dee 711. In operation, the magnetic field between active dee 711 and dummy dee 710 causes particles (e.g., protons) to accelerate outwardly. The acceleration is spiral to create orbits about the plasma column, with the particle-to-plasma-column radius progressively increasing. The radii of curvature of the spirals depend on a particle's mass, energy imparted to the particle by the RF field, and a strength of the magnetic field.

When the magnetic field is high, it can become difficult to impart enough energy to a particle so that it has a large enough radius of curvature to clear the physical housing of the particle source on its initial turn(s) during acceleration. The magnetic field is relatively high in the region of the particle source, e.g., on the order of 2 Tesla (T) or more (e.g., 4 T, 5 T, 6 T, 8 T, 8.8 T, 8.9 T, 9 T, 10.5 T, or more). As a result of this relatively high magnetic field, the initial particle-to-ion-source radius is relatively small for low energy particles, where low energy particles include particles that are first drawn from the plasma column. For example, such a radius may be on the order of 1 mm. Because the radii are so small, at least initially, some particles may come into contact with the particle source's housing area, thereby preventing further outward acceleration of such particles. Accordingly, the housing of particle source 700 is interrupted, or separated to form two parts, as shown in FIG. 16. That is, a portion of the particle source's housing may be entirely removed at the acceleration region 714, e.g., at about the point where the particles are to be drawn from the particle source. This interruption is labeled 715 in FIG. 16. The housing may also be removed for distances above, and below, the acceleration region. In an alternative implementation, a substantial portion (e.g., 30%, 40%, 50% or more), but not all, of the PIG source housing is removed, leaving the plasma beam partly exposed. Thus, portions of the PIG housing are separated from their counterpart portions, but there is not complete separation as was the case above.

In the synchrocyclotron described herein, a particle beam is extracted using a resonant extraction system. That is, radial oscillation of the beam is created by a magnetic perturbation inside the accelerator, which establishes a resonance of these oscillations. When a resonant extraction system is used, extraction efficiency is improved by limiting the phase space extent of the internal beam. With attention to the design of the magnetic and RF field generating structures, the phase space extent of the beam at extraction is determined by the phase space extent at the beginning of acceleration (e.g., at emergence from the particle source). As a result, relatively little beam may be lost at the entrance to the extraction channel and background radiation from the accelerator can be reduced.

Cathodes 717 may be "cold" cathodes. A cold cathode may be a cathode that is not heated by an external heat source. Also, the cathodes may be pulsed, meaning that they output plasma burst(s) periodically rather than continuously. When the cathodes are cold, and are pulsed, the cathodes are less subject to wear and can therefore last relatively long. Furthermore, pulsing the cathodes can eliminate the need to water-cool the cathodes. In one implementation, cathodes 717 pulse at a relatively high voltage, e.g., about 1 kV to about 4 kV, and moderate peak cathode discharge currents of about 50 mA to about 200 mA at a duty cycle between about 0.1% and about 1% or 2% at repetition rates between about 200 Hz to about 1 KHz. However, the particle source is not limited to these values.

Various aspects of example particle therapy system described herein may be computer-controlled. Computer controls may be effected through one or more signals output from the computer to various electronics on the particle therapy system. For example, the intensity of the particle beam generated by the particle therapy system may be measured, and the particle therapy system may be adjusted to control the intensity of the particle beam. The measurement and adjustment may occur once, at each use of the particle therapy system, in real-time (e.g., during treatment), or at other frequencies. In some implementations, the various parameters or other features of the particle accelerator described below may be varied, and the intensity of the resulting particle beam measured in order to determine if the appropriate result was achieved. If the appropriate result was not achieved, then the parameters or other features may be varied again and the results measured until the appropriate results are achieved.

In an example implementation, the time-width of pulses output by the particle source may be varied to control the intensity of the particle beam. In other words, the amount of time that the particle source is intermittently (e.g., periodically) activated is varied, thereby providing the plasma column for different periods of time and enabling extraction of different numbers of particles. For example, if the pulse width is increased, the number of particles extracted increases and, if the pulse width decreases, the number of particles extracted decreases. In some implementations, there is a linear relationship between the time that the particle source is on and the intensity of the particle beam. For example, the relationship may be one-to-one plus an offset. In an example implementation, the particle source may be pulsed within a frequency window that occurs during a frequency sweep between a maximum frequency of about 135 MHz and a minimum frequency of about 95 MHz or 90 MHz. For example, the particle source may be pulsed between 132 MHz and 131 MHz for a period of time. In an implementation, this period of time is about 40 µs; however, these values may vary or be different in other implementations. Failing to pulse the particle source outside of the frequency window can inhibit extraction of particles from the plasma column.

Figure 17:
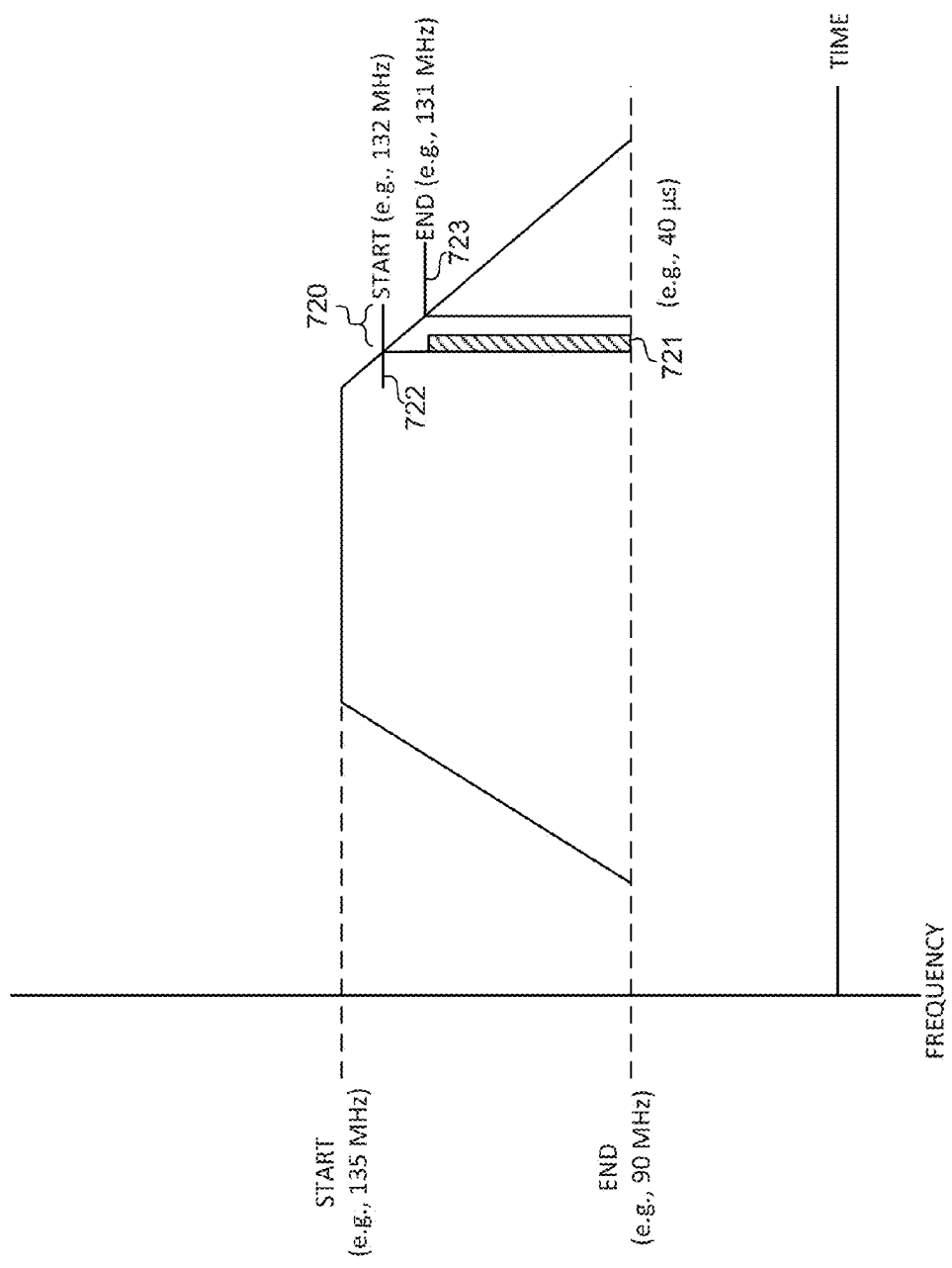
FIG. 17 is a graph showing an example voltage sweep, extraction window, and particle source pulse width.

FIG. 17 is a graph showing the voltage sweep in the resonant cavity over time from a maximum frequency (e.g., 135 MHz) to a minimum frequency (e.g., 90 MHz or 95 MHz). The extraction window 720 occurs, in this example, between 132 MHz and 131 MHz. The width of pulse 721 may be varied to control the intensity of the particle beam output by the particle accelerator.

In other implementations, the voltage of cathodes 717 may be adjusted in order to control the amount of ionization in the plasma column, and thereby control the intensity of the particle beam output from the accelerator. Varying the voltage of cold cathodes can produce particularly sharp pulse edges.

In other implementations, the gas flow in tube 101 may be adjusted to increase or decrease the amount of hydrogen in the plasma column. As explained above, this increase or decrease in hydrogen can cause an increase or decrease in the amount of particles in the plasma column that are available for extraction. Thus, by varying the amount/flow of hydrogen provided by the particle source, it is possible to control the amount of particles available for extraction and thus the intensity of the resulting particle beam. For example, as explained above, when more particles are present in the plasma column, more particles are extracted during the RF voltage sweep, thereby increasing the intensity of the particle beam. When fewer particles are present in the plasma column, fewer particles are extracted during the RF voltage sweep, thereby decreasing the intensity of the particle beam.

In other implementations, increasing the magnitude of the RF voltage during the extraction period can increase the amount of particles extracted and thereby increase the intensity of the particle beam. In this regard, the magnitude of the RF voltage may be varied during the entire period of the RF sweep or it may be varied only during times that particles are extractable from the plasma column. For example, in some implementations, particles are extracted from the plasma column during the sweep period from 132 MHz to 131 MHz. The magnitude of the RF voltage may be increased during that period only or, in some cases, during periods that precede and follow the extraction period. In some example implementations, the time period during which the magnitude may be increased is 20-40 µs. Notably, these values are specific to one example particle accelerator, and the values, including frequency window and time period, may be different for different systems.

In other implementations, particle source 700 is controllable to provide pulses of the ionized plasma at specific frequencies proximate to a decrease from the maximum RF frequency to the minimum RF frequency during the voltage sweep. For example, referring to FIG. 17, pulse width 721 may be controlled to occur at any point between a starting (e.g., maximum) frequency 722 and an ending (e.g., minimum) frequency 723. The amount of particles extracted at various frequencies may be measured in order to determine the best location.

In some implementations, pulse widths may be varied by controlling the rate of the RF sweep. For example, slower RF sweeps may result on longer pulses and, thus, more particles (intensity) per pulse.

In other implementations, the voltage source is configurable to vary the RF voltage in order to control an intensity of the beam of particles. For example, the RF voltage may be swept over a time-scale from a high value to a low value. Initially, the RF voltage may be at a high value (e.g., constant for a period of time). There, the voltage is applied for an initial period of time (e.g., 20-40 µs). Then, the voltage is reduced, e.g., every 20 µs during the sweep so that its amplitude is adjusted to control the intensity of the particle beam. The slope of the decreasing magnetic field (versus time) may be increased or decreased in order to change the amount of particle extracted. In some implementations, the voltage may be applied in steps to control the particle beam output.

In other implementations, pulse-blanking may be used to control the intensity of the particle beam. For example, particle source 700 may be controlled to selectively output pulses of the ionized plasma. For example, the pulses may be output for a period during every voltage sweep; however, pulse output may be skipped in every $N^{th}$ (N>1) sweep. So, for example, the control system may detect that there is 1% too much beam, in which case every $100^{th}$ pulse may be skipped. In other implementations, pulses may be skipped more frequently, e.g., every second, third, tenth or any other appropriate numbered pulse may be skipped.

In other implementations, a bias voltage may be applied to the active dee and/or to the dummy dee to reduce the effects of multi-pactoring and thereby increase the intensity of the particle beam. In this regard, multi-pactoring occurs when electrons bounce between dee plates, causing additional electrons to be cast-off of the dee plates upon impact. The result can adversely affect the operation of the dee plates to the point of electrically shorting the dee plates.

Figure 18:
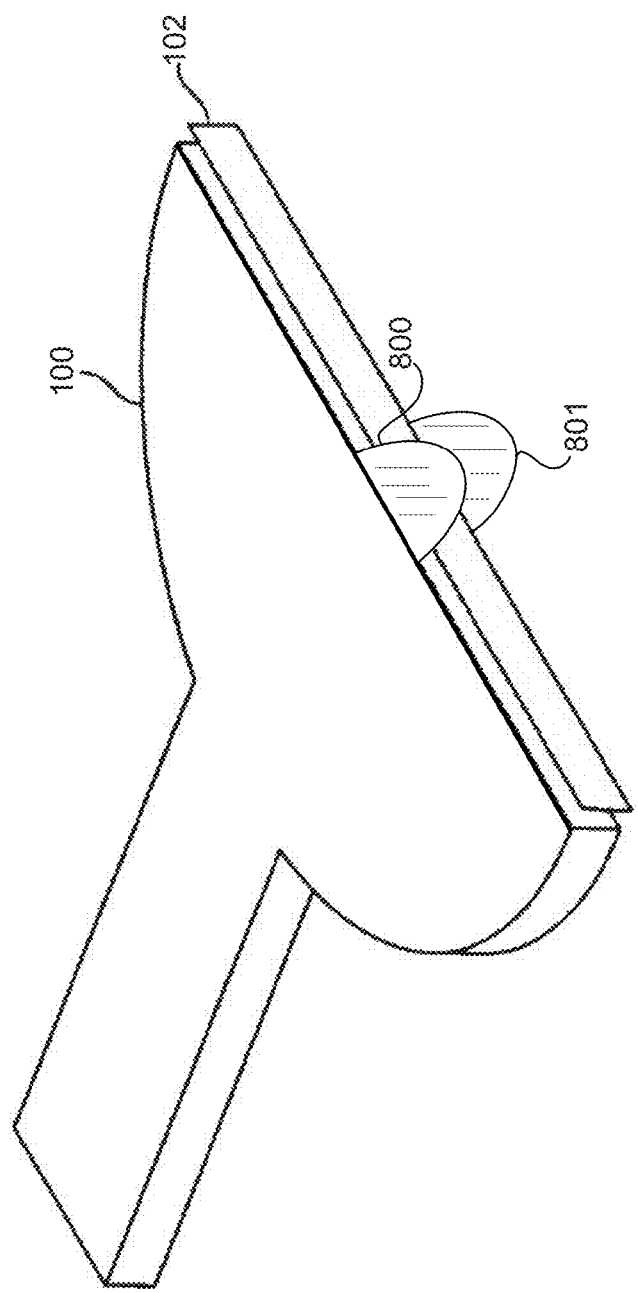
FIG. 18 is a perspective view of example active and dummy dees that may be used with the particle therapy system described herein.

To reduce the effects of multi-pactoring, a DC bias voltage may be applied to the active dee and/or to the dummy dee. This causes the background RF voltage to oscillate further away from ground than would otherwise be the case, thereby reducing electron transfer between dees. In an implementation, a DC bias voltage is applied to the dummy dee only, and the dummy dee is isolated from ground. In other implementations, differential DC bias voltages are applied to the dummy dee and the active dee. For example, a larger DC bias voltage may be applied to the dummy dee and a smaller DC bias voltage may be applied to the active dee. In some implementations, DC the bias plates 800, 801 of FIG. 18 may be added to the dummy dee 102. In this figure, the active dee is labeled 100.

In some implementations, the DC bias voltage differential (that is, the difference between the bias voltages applied to the active and dummy dees) may be within the +/−50% range. The specific amounts of the DC bias voltage may vary based on the level of the RF voltage. For example, 2.1 KV DC voltage may be applied to the dummy dee and 1.7 KV DC voltage may be applied to the active dee. In another example, 1.5 KV DC voltage may be applied to the dummy dee and 1.0 KV DC voltage may be applied to the active dee. In another example, 1.9 KV DC voltage may be applied to the dummy dee and 1.5 KV DC voltage may be applied to the active dee. In other implementations, different DC bias voltage may be used.

Figure 19:
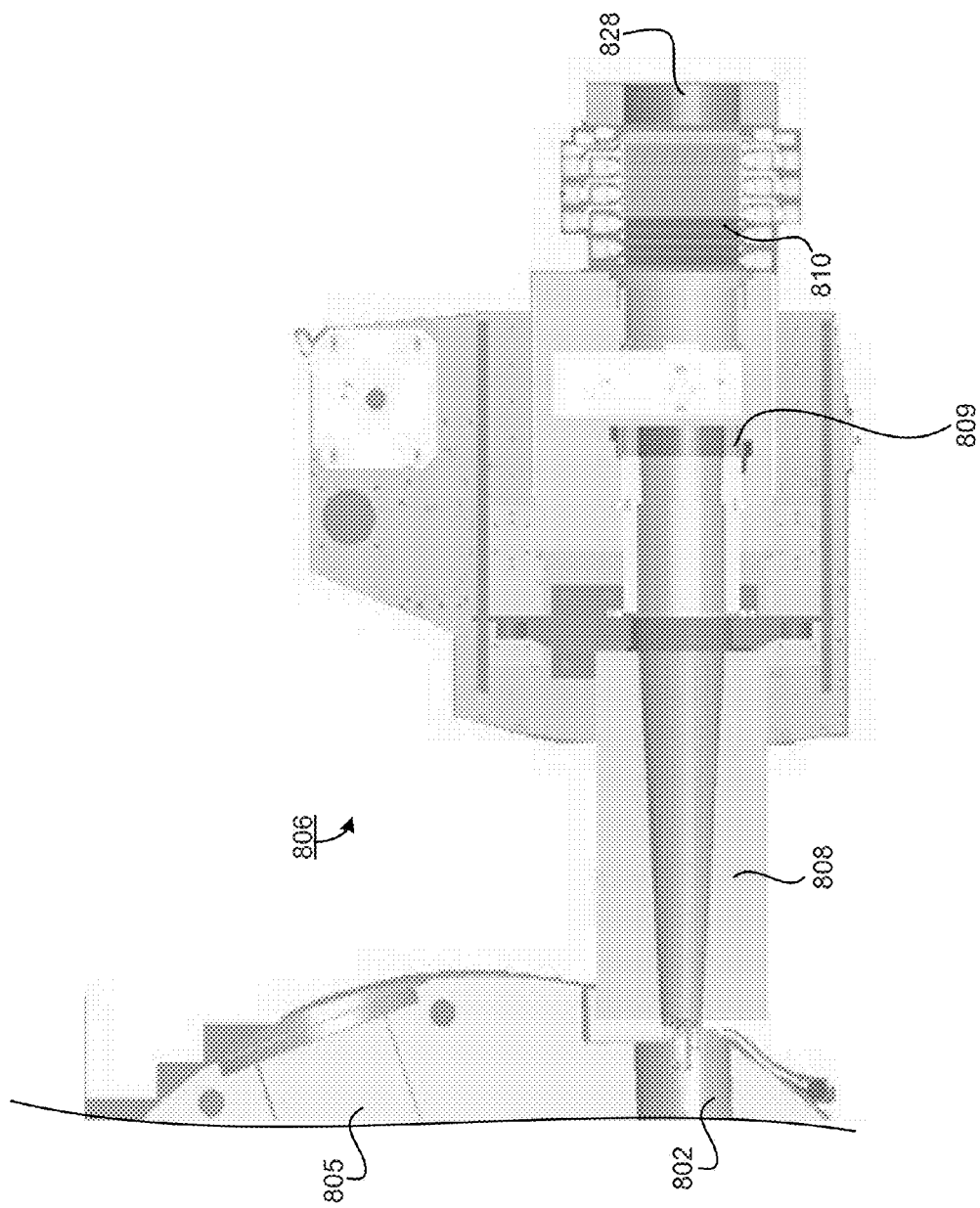
FIG. 19 is a side view of an example scanning system.
Figure 20:
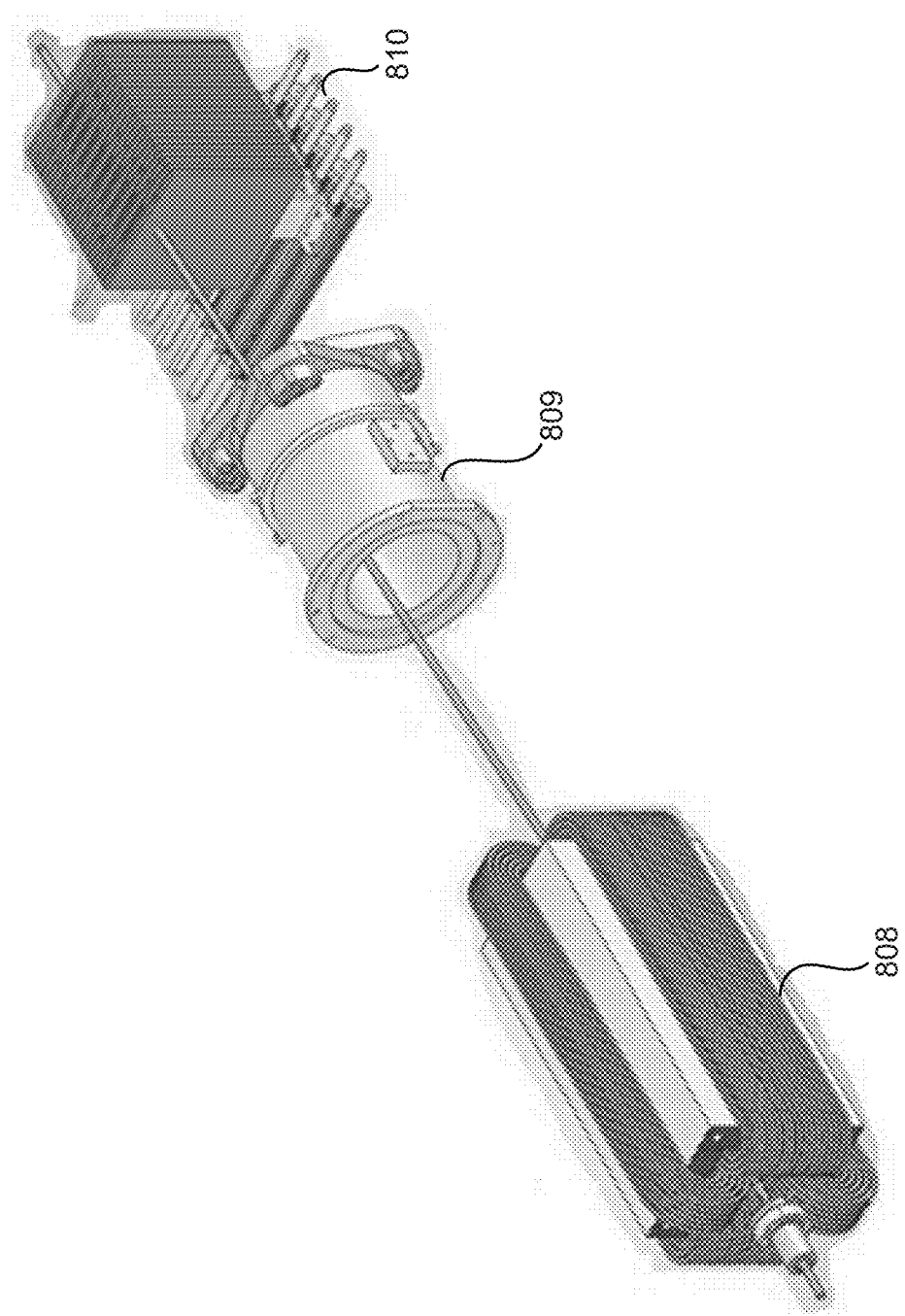
FIG. 20 is a perspective view of the example scanning system.

Referring to FIG. 19, at the output of extraction channel 802 of a particle accelerator (which may have the configuration shown in FIGS. 1 and 2) is a beam formation system, such as beam formation system 125. The beam formation system may be a scanning system. An example scanning system 806 is shown in FIG. 19, which may be used to scan the particle beam across at least part of an irradiation target. FIG. 20 also shows examples of the components of the scanning system include a scanning magnet 808, an ion chamber 809, and an energy degrader 810. Other components of the scanning system are not shown in FIG. 20.

In an example operation, scanning magnet 808 is controllable in two dimensions (e.g., Cartesian XY dimensions) to direct the particle beam across a part (e.g., a cross-section) of an irradiation target. Ion chamber 809 detects the dosage of the beam and feeds-back that information to a control system. Energy degrader 810 is controllable to move material into, and out of, the path of the particle beam to change the energy of the particle beam and therefore the depth to which the particle beam will penetrate the irradiation target.

Figure 22:
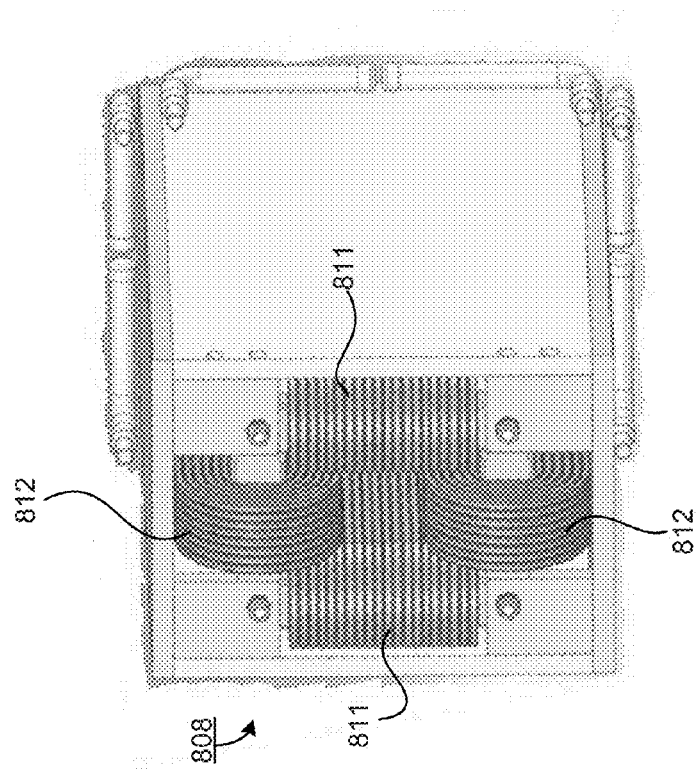
FIGS. 21 and 22 are front and perspective views, respectively, of an example scanning magnet that may be used in the example scanning system.
Figure 21:
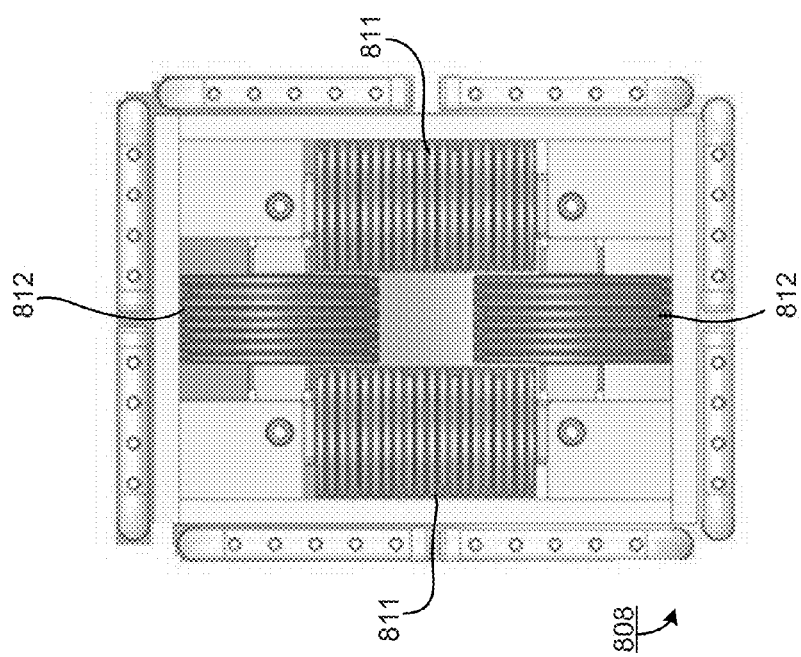

FIGS. 21 and 22 shows views of an example scanning magnet 808. Scanning magnet 808 includes two coils 811, which control particle beam movement in the X direction, and two coils 812, which control particle beam movement in the Y direction. Control is achieved, in some implementations, by varying current through one or both sets of coils to thereby vary the magnetic field(s) produced thereby. By varying the magnetic field(s) appropriately, the particle beam can be moved in the X and/or Y direction across the irradiation target. In some implementations, the scanning magnet is not movable physically relative to the particle accelerator. In other implementations, the scanning magnet may be movable relative to the accelerator (e.g., in addition to the movement provided by the gantry).

In this example, ion chamber 809 detects dosage applied by the particle beam by detecting the numbers of ion pairs created within a gas caused by incident radiation. The numbers of ion pairs correspond to the dosage provided by the particle beam. That information is fed-back to a computer system that controls operation of the particle therapy system. The computer system (not shown), which may include memory and one or more processing devices, determines if the dosage detected by ion chamber is the intended dose. If the dosage is not as intended, the computer system may control the accelerator to interrupt production and/or output of the particle beam, and/or control the scanning magnet to prevent output of the particle beam to the irradiation target.

Figure 23:
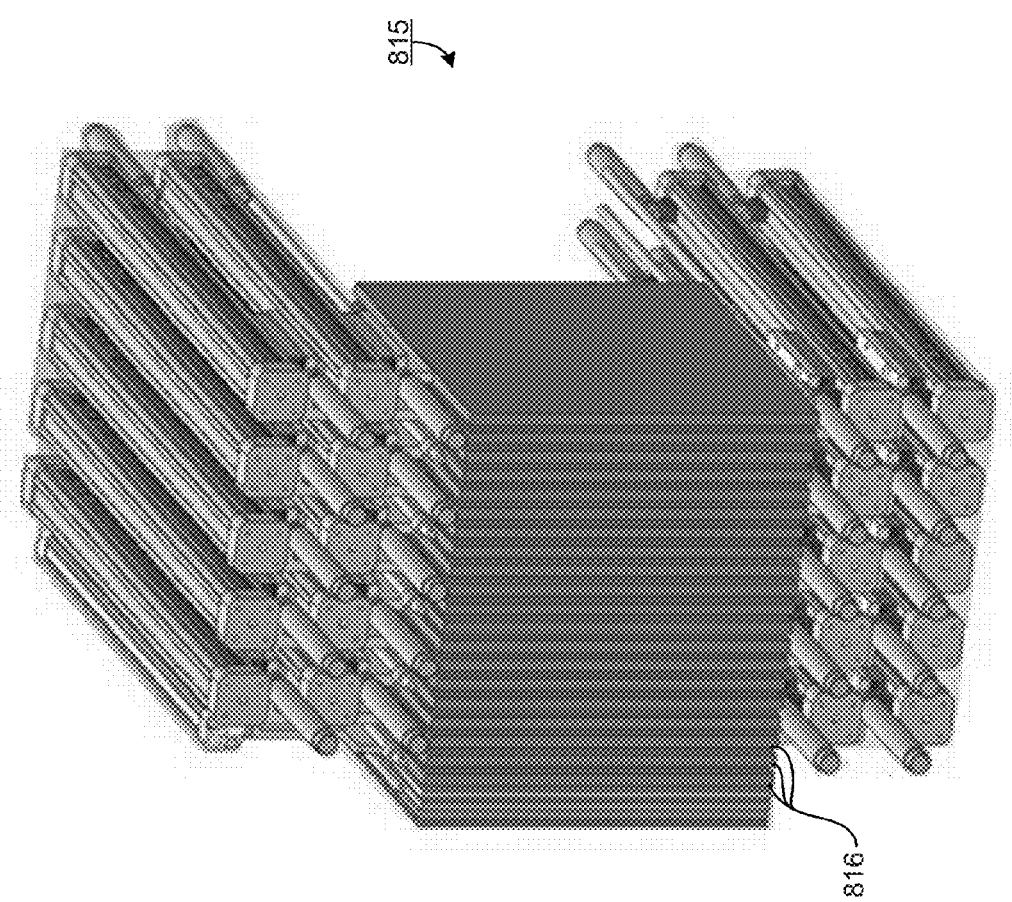
FIG. 23 is a perspective view of an example range modulator that may be used in the example scanning system.

FIG. 23 shows a range modulator 815, which is an example implementation of energy degrader 810. In some implementations, such as that shown in FIG. 23, range modulator includes a series of plates 816. The plates may be made of one or more energy absorbing materials.

One or more of the plates is movable into, or out of, the beam path to thereby affect the energy of the particle beam and, thus, the depth of penetration of the particle beam within the irradiation target. For example, the more plates that are moved into the path of the particle beam, the more energy that will be absorbed by the plates, and the less energy the particle beam will have. Conversely, the fewer plates that are moved into the path of the particle beam, the less energy that will be absorbed by the plates, and the more energy the particle beam will have. Higher energy particle beams penetrate deeper into the irradiation target than do lower energy particle beams. In this context, "higher" and "lower" are meant as relative terms, and do not have any specific numeric connotations.

Plates are moved physically into, and out of, the path of the particle beam. For example, as shown in FIG. 24, a plate 816*a* moves along the direction of arrow 817 between positions in the path of the particle beam and outside the path of the particle beam. The plates are computer-controlled. Generally, the number of plates that are moved into the path of the particle beam corresponds to the depth at which scanning of an irradiation target is to take place. For example, the irradiation target can be divided into cross-sections, each of which corresponds to an irradiation depth. One or more plates of the range modulator can be moved into, or out of, the beam path to the irradiation target in order to achieve the appropriate energy to irradiate each of these cross-sections of the irradiation target.

In some implementations, a treatment plan is established prior to treating the irradiation target using scanning. The treatment plan may specify how scanning is to be performed for a particular irradiation target. In some implementations, the treatment plan specifies the following information: a type of scanning (e.g., spot scanning or raster scanning); scan locations (e.g., locations of spots to be scanned); magnet current per scan location; dosage-per-spot; locations (e.g., depths) of irradiation target cross-sections; particle beam energy per cross-section; plates or other types of pieces to move into the beam path for each particle beam energy; and so forth. Generally, spot scanning involves applying irradiation at discrete spots on an irradiation target and raster scanning involves moving a radiation spot across the radiation target. The concept of spot size therefore applies for both raster and spot scanning.

In some implementations, the intensity of spots in the scanning system may vary from spot-to-spot. Any of the techniques described herein may be used to vary the intensity of the particle beam from spot-to-spot. For example, the intensity of the particle beam may be varied from individual spot to individual spot, or from one group of spots to another group of spots, and so forth.

The pulse-width modulation techniques (PWM) described herein to vary the pulse width of pulses of the particle beam (and thereby vary the number of particles per pulse, i.e., pulse intensity) may be particularly useful for varying the intensity from spot-to-spot in the scanning system. PWM techniques may be particularly useful in a scanning context because they enable variation in spot intensity rather quickly, e.g., in a sub-second time-frame, and have a relatively wide dynamic range (although non-PWM techniques are still usable).

Any two more of the foregoing implementations may be used in an appropriate combination to affect the energy of a particle beam in the extraction channel. Likewise, individual features of any two more of the foregoing implementations may be used in an appropriate combination for the same purpose.

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

The example implementations described herein are not limited to use with a particle therapy system or to use with the example particle therapy systems described herein. Rather, the example implementations can be used in any appropriate system that directs accelerated particles to an output.

Additional information concerning the design of an example implementation of a particle accelerator that may be used in a system as described herein can be found in U.S. Provisional Application No. 60/760,788, entitled "High-Field Superconducting Synchrocyclotron" and filed Jan. 20, 2006; U.S. patent application Ser. No. 11/463,402, entitled "Magnet Structure For Particle Acceleration" and filed Aug. 9, 2006; and U.S. Provisional Application No. 60/850,565, entitled "Cryogenic Vacuum Break Pneumatic Thermal Coupler" and filed Oct. 10, 2006, all of which are incorporated herein by reference.

The following applications, all of which are filed on the same date as the subject application (entitled "CONTROLLING INTENSITY OF A PARTICLE BEAM" (Application No. 61/707,466)), are incorporated by reference into the subject application: the U.S. Provisional Application entitled "ADJUSTING ENERGY OF A PARTICLE BEAM" (Application No. 61/707,515), the U.S. Provisional Application entitled "ADJUSTING COIL POSITION" (Application No. 61/707,548), the U.S. Provisional Application entitled "FOCUSING A PARTICLE BEAM USING MAGNETIC FIELD FLUTTER" (Application No. 61/707,572), the U.S. Provisional Application entitled "MAGNETIC FIELD REGENERATOR" (Application No. 61/707,590), the U.S. Provisional Application entitled "FOCUSING A PARTICLE BEAM" (Application No. 61/707,704), the U.S. Provisional Application entitled "CONTROLLING PARTICLE THERAPY (Application No. 61/707,624), and the U.S. Provisional Application entitled "CONTROL SYSTEM FOR A PARTICLE ACCELERATOR" (Application No. 61/707,645).

The following are also incorporated by reference into the subject application: U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, U.S. patent application Ser. No. 11/937,573 filed on Nov. 9, 2007, U.S. patent application Ser. No. 11/187,633, titled "A Programmable Radio Frequency Waveform Generator for a Synchrocyclotron," filed Jul. 21, 2005, U.S. Provisional Application No. 60/590,089, filed on Jul. 21, 2004, U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005.

Any features of the subject application may be combined with one or more appropriate features of the following: the U.S. Provisional Application entitled "ADJUSTING ENERGY OF A PARTICLE BEAM" (Application No. 61/707,515), the U.S. Provisional Application entitled "ADJUSTING COIL POSITION" (Application No. 61/707,548), the U.S. Provisional Application entitled "FOCUSING A PARTICLE BEAM USING MAGNETIC FIELD FLUTTER" (Application No. 61/707,572), the U.S. Provisional Application entitled "MAGNETIC FIELD REGENERATOR" (Application No. 61/707,590), the U.S. Provisional Application entitled "FOCUSING A PARTICLE BEAM" (Application No. 61/707,704), the U.S. Provisional Application entitled "CONTROLLING PARTICLE THERAPY (Application No. 61/707,624), and the U.S. Provisional Application entitled "CONTROL SYSTEM FOR A PARTICLE ACCELERATOR" (Application No. 61/707,645), U.S. Pat. No. 7,728,311 which issued on Jun. 1, 2010, U.S. patent application Ser. No. 11/948,359 which was filed on Nov. 30, 2007, U.S. patent application Ser. No. 12/275,103 which was filed on Nov. 20, 2008, U.S. patent application Ser. No. 11/948,662 which was filed on Nov. 30, 2007, U.S. Provisional Application No. 60/991,454 which was filed on Nov. 30, 2007, U.S. Pat. No. 8,003,964 which issued on Aug. 23, 2011, U.S. Pat. No. 7,208,748 which issued on Apr. 24, 2007, U.S. Pat. No. 7,402,963 which issued on Jul. 22, 2008, U.S. patent application Ser. No. 13/148,000 filed Feb. 9, 2010, U.S. patent application Ser. No. 11/937,573 filed on Nov. 9, 2007, U.S. patent application Ser. No. 11/187,633, titled "A Programmable Radio Frequency Waveform Generator for a Synchrocyclotron," filed Jul. 21, 2005, U.S. Provisional Application No. 60/590,089, filed on Jul. 21, 2004, U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005.

Except for the provisional application from which this patent application claims priority and the documents incorporated by reference above, no other documents are incorporated by reference into this patent application.

Other implementations not specifically described herein are also within the scope of the following claims.

What is claimed is:

1. A synchrocyclotron comprising:
a particle source to provide pulses of ionized plasma to a cavity;
a voltage source to provide a radio frequency (RF) voltage to the cavity to accelerate particles from the ionized plasma outwardly;
an extraction channel to receive a beam of particles from the cavity for output from the synchrocyclotron; and
a control system comprising one or more processing devices to control the particle source to provide pulse widths of the ionized plasma in order to output the beam of particles at an intensity selected from different intensities;
wherein the particle source comprises cathodes to provide voltage to ionize hydrogen to produce the ionized plasma, the cathodes being unheated by an external source.

2. The synchrocyclotron of claim 1, wherein the particle source is configured to activate for a period of time in response to a control signal from the control system, where the particle source generates a pulse of ionized plasma when activated.

3. The synchrocyclotron of claim 1, wherein the particle source is configured to generate pulses of ionized plasma periodically.

4. The synchrocyclotron of claim 3, wherein the particle beam is output for a duration of about 0.1 µs to 100 µs.

5. The synchrocyclotron of claim 3, wherein the particle beam is output for a duration of about 0.1 µs to 100 µs about every 2 ms.

6. A proton therapy system comprising:
the synchrocyclotron of claim 1; and
a gantry on which the synchrocyclotron is mounted, the gantry for rotating the synchrocyclotron around a patient position.

7. The synchrocyclotron of claim 1, wherein the voltage source comprises a first dee and a second dee, and wherein at least one of the first dee or the second dee has a bias voltage applied thereto.

8. The synchrocyclotron of claim 1, wherein the voltage source is configured to sweep the RF voltage between a maximum frequency and a minimum frequency, and the particle source is controllable to affect the intensity by providing pulses of the ionized plasma at specific frequencies during a decrease from the maximum frequency of the RF voltage to the minimum frequency of the RF voltage.

9. A synchrocyclotron comprising:
a particle source to provide pulses of ionized plasma to a cavity, the particle source comprising cathodes to provide voltage to ionize hydrogen to produce the ionized plasma;
a voltage source to provide a radio frequency (RF) voltage to the cavity to accelerate particles from the ionized plasma outwardly;
an extraction channel to receive a beam of particles from the cavity for output from the synchrocyclotron; and
a control system comprising one or more processing devices to control a voltage provided by the cathodes in order to output the beam of particles at an intensity selected from among different intensities;
wherein the cathodes are unheated by an external source.

10. The synchrocyclotron of claim 9, wherein the voltage is controllable such that increasing the voltage increases an intensity of the beam of particles and such that decreasing the voltage decreases the intensity of the beam of particles.

11. A proton therapy system comprising:
the synchrocyclotron of claim 9; and
a gantry on which the synchrocyclotron is mounted, the gantry for rotating the synchrocyclotron around a patient position.

12. The synchrocyclotron of claim 9, wherein the voltage source comprises a first dee and a second dee, and wherein at least one of the first dee or the second dee has a bias voltage applied thereto.

13. The synchrocyclotron of claim 9, wherein the voltage source is configured to sweep the RF voltage between a maximum frequency and a minimum frequency, and the particle source is controllable to affect the intensity by providing pulses of the ionized plasma at specific frequencies during a decrease from the maximum frequency of the RF voltage to the minimum frequency of the RF voltage.

14. A synchrocyclotron comprising:
a particle source to provide pulses of ionized plasma to a cavity, the particle source comprising cathodes to provide voltage to ionize hydrogen to produce the ionized plasma;

a voltage source to provide a radio frequency (RF) voltage to the cavity to accelerate particles from the ionized plasma outwardly;

an extraction channel to receive a beam of particles from the cavity for output from the synchrocyclotron; and a control system comprising one or more processing devices to control the particle source to adjust an amount of the hydrogen between the cathodes in order to output the beam of particles at an intensity selected from among different intensities;

wherein the cathodes are unheated by an external source.

15. The synchrocyclotron of claim 14, wherein the amount of hydrogen is adjustable such that increasing the amount of hydrogen increases an intensity of the beam of particles and such that decreasing the amount of hydrogen decreases the intensity of the beam of particles.

16. A proton therapy system comprising:
the synchrocyclotron of claim 14; and
a gantry on which the synchrocyclotron is mounted, the gantry for rotating the synchrocyclotron around a patient position.

17. The synchrocyclotron of claim 14, wherein the voltage source comprises a first dee and a second dee, and wherein at least one of the first dee or the second dee has a bias voltage applied thereto.

18. The synchrocyclotron of claim 14, wherein the voltage source is configured to sweep the RF voltage between a maximum frequency and a minimum frequency, and the particle source is controllable to affect the intensity by providing pulses of the ionized plasma at specific frequencies during a decrease from the maximum frequency of the RF voltage to the minimum frequency of the RF voltage.

19. A synchrocyclotron comprising:
a particle source to provide pulses of ionized plasma to a cavity;
a voltage source to provide a radio frequency (RF) voltage to the cavity to accelerate particles from the ionized plasma outwardly;
an extraction channel to receive a beam of particles from the cavity for output from the synchrocyclotron; and
a control system comprising one or more processing devices to control the voltage source to provide a magnitude of the RF voltage in order to output the beam of particles at an intensity selected from among different intensities;
wherein the particle source comprises cathodes to provide voltage to ionize hydrogen to produce the ionized plasma, the cathodes being unheated by an external source.

20. The synchrocyclotron of claim 19, wherein the magnitude of the RF voltage is adjustable such that increasing the magnitude increases an intensity of the beam of particles and such that decreasing the magnitude decreases the intensity of the beam of particles.

21. A proton therapy system comprising:
the synchrocyclotron of claim 19; and
a gantry on which the synchrocyclotron is mounted, the gantry for rotating the synchrocyclotron around a patient position.

22. The synchrocyclotron of claim 19, wherein the voltage source comprises a first dee and a second dee, and wherein at least one of the first dee or the second dee has a bias voltage applied thereto.

23. The synchrocyclotron of claim 19, wherein the voltage source is configured to sweep the RF voltage between a maximum frequency and a minimum frequency, and the particle source is controllable to affect the intensity by providing pulses of the ionized plasma at specific frequencies during a decrease from the maximum frequency of the RF voltage to the minimum frequency of the RF voltage.

24. A synchrocyclotron comprising:
a particle source to provide pulses of ionized plasma to a cavity;
a voltage source to provide a radio frequency (RF) voltage to the cavity to accelerate particles from the ionized plasma outwardly, the RF voltage sweeping between a maximum frequency and a minimum frequency;
an extraction channel to receive a beam of particles from the cavity for output from the synchrocyclotron; and
a control system comprising one or more processing devices to control the particle source to output the beam of particles at an intensity selected from among different intensities, the particle source being controllable by the control system to provide pulses of the ionized plasma at specific frequencies during a decrease from the maximum frequency of the RF voltage to the minimum frequency of the RF voltage;
wherein the particle source comprises cathodes to provide voltage to ionize hydrogen to produce the ionized plasma, the cathodes being unheated by an external source.

25. The synchrocyclotron of claim 24, wherein the particle source is controllable to provide pulses of the ionized plasma between 132 MHz of RF voltage and 131 MHz of RF voltage from a decrease from a maximum frequency of about 135 MHz of the RF voltage.

26. A proton therapy system comprising:
the synchrocyclotron of claim 24; and
a gantry on which the synchrocyclotron is mounted, the gantry for rotating the synchrocyclotron around a patient position.

27. The synchrocyclotron of claim 24, wherein the voltage source comprises a first dee and a second dee, and wherein at least one of the first dee or the second dee has a bias voltage applied thereto.

28. A synchrocyclotron comprising:
a particle source to provide pulses of ionized plasma to a cavity;
a voltage source to provide a radio frequency (RF) voltage to the cavity to accelerate particles from the ionized plasma outwardly;
an extraction channel to receive a beam of particles from the cavity for output from the synchrocyclotron; and
a control system comprising one or more processing devices to control the particle source to selectively output pulses of the ionized plasma in order to output the beam of particles at an intensity selected from among different intensities;
wherein the particle source comprises cathodes to provide voltage to ionize hydrogen to produce the ionized plasma, the cathodes being unheated by an external source.

29. The synchrocyclotron of claim 28, wherein the voltage source is configured to sweep the RF voltage periodically from a maximum frequency to a minimum frequency; and
wherein selectively outputting the pulses comprises outputting pulses in certain ones of the RF voltage sweeps and not in others of the RF voltage sweeps.

30. The synchrocyclotron of claim 28, wherein the voltage source is configured to sweep the RF voltage periodically from a maximum frequency to a minimum frequency; and wherein selectively outputting the pulses comprises skipping pulse output in every $N^{th}$ (N>1) sweep.

31. The synchrocyclotron of claim 28, wherein the control system is configured to perform operations comprising: selecting the intensity of the beam of particles.

32. A proton therapy system comprising:
the synchrocyclotron of claim 28; and
a gantry on which the synchrocyclotron is mounted, the gantry for rotating the synchrocyclotron around a patient position.

33. The synchrocyclotron of claim 28, wherein the voltage source comprises a first dee and a second dee, and wherein at least one of the first dee or the second dee has a bias voltage applied thereto.

34. The synchrocyclotron of claim 28, wherein the voltage source is configured to sweep the RF voltage between a maximum frequency and a minimum frequency, and the particle source is controllable to affect the intensity by providing pulses of the ionized plasma at specific frequencies during a decrease from the maximum frequency of the RF voltage to the minimum frequency of the RF voltage.

35. A synchrocyclotron comprising:
a particle source to provide pulses of ionized plasma to a cavity;
a voltage source to provide a radio frequency (RF) voltage to the cavity to accelerate particles from the ionized plasma outwardly;
an extraction channel to receive a beam of particles from the cavity for output from the synchrocyclotron; and
a control system comprising one or more processing devices to control the voltage source to vary a rate of change of the RF voltage in order to output the beam of particles at an intensity selected from among different intensities;
wherein the particle source comprises cathodes to provide voltage to ionize hydrogen to produce the ionized plasma, the cathodes being unheated by an external source.

36. A proton therapy system comprising:
the synchrocyclotron of claim 35; and
a gantry on which the synchrocyclotron is mounted, the gantry for rotating the synchrocyclotron around a patient position.

37. The synchrocyclotron of claim 35, wherein the voltage source comprises a first dee and a second dee, and wherein at least one of the first dee or the second dee has a bias voltage applied thereto.

38. The synchrocyclotron of claim 35, wherein the voltage source is configured to sweep the RF voltage between a maximum frequency and a minimum frequency, and the particle source is controllable to affect the intensity by providing pulses of the ionized plasma at specific frequencies during a decrease from the maximum frequency of the RF voltage to the minimum frequency of the RF voltage.

39. A synchrocyclotron comprising:
a particle source to provide pulses of ionized plasma to a cavity;
a voltage source to provide a radio frequency (RF) voltage to the cavity to accelerate particles from the ionized plasma outwardly, the voltage source comprising a first dee and a second dee, wherein at least one of the first dee or the second dee has a bias voltage applied thereto; and
an extraction channel to receive a beam of particles from the cavity for output from the synchrocyclotron;
wherein the particle source comprises cathodes to provide voltage to ionize hydrogen to produce the ionized plasma, the cathodes being unheated by an external source.

40. The synchrocyclotron of claim 39, wherein the first dee has a first bias voltage applied thereto and the second dee has a second bias voltage applied thereto, the first bias voltage being different from the second bias voltage.

41. The synchrocyclotron of claim 39, wherein the first dee has the bias voltage applied thereto and the second dee is electrically grounded.

42. A proton therapy system comprising:
the synchrocyclotron of claim 39; and
a gantry on which the synchrocyclotron is mounted, the gantry for rotating the synchrocyclotron around a patient position.

43. The synchrocyclotron of claim 39, wherein the voltage source is configured to sweep the RF voltage between a maximum frequency and a minimum frequency, and the particle source is controllable to affect the intensity by providing pulses of the ionized plasma at specific frequencies during a decrease from the maximum frequency of the RF voltage to the minimum frequency of the RF voltage.

44. The synchrocyclotron of claim 39, wherein the first dee comprises a DC bias plate, and the bias voltage is a DC bias voltage.

* * * * *

UNITED STATES PATENT AND TRADEMARK OFFICE
CERTIFICATE OF CORRECTION

PATENT NO.        : 9,723,705 B2
APPLICATION NO.   : 14/039307
DATED             : August 1, 2017
INVENTOR(S)       : Kenneth Gall et al.

Page 1 of 1

It is certified that error appears in the above-identified patent and that said Letters Patent is hereby corrected as shown below:

In the "FOREIGN PATENT DOCUMENTS" section of the "References Cited" list, in the righthand column of Page 7, after --WO WO-2014/052722 A2 4/2014-- please insert the following references:

--CN  1816243 A       8/2006
JP    S48-108098 U    12/1973
JP    S58-141000 A    8/1983
JP    S61-80800 A     4/1986
JP    S62-150804 A    7/1987
JP    S62-186500 A    8/1987
JP    S63-149344 A    6/1988
JP    S63-218200 A    9/1988
JP    S63-226899 A    9/1988
JP    S64-89621 A     4/1989
JP    H01-276797 A    11/1989
JP    H01-302700 A    12/1989
JP    H06-036893 A    2/1994
JP    H06-233831 A    8/1994
JP    H07-260939 A    10/1995
JP    H07-263196 A    10/1995
JP    H08-173890 A    7/1996
JP    H08-264298 A    10/1996
JP    H09-162585 A    6/1997
JP    H10-071213 A    3/1998
JP    H11-102800 A    4/1999--

Signed and Sealed this
Twelfth Day of September, 2017

Joseph Matal
*Performing the Functions and Duties of the
Under Secretary of Commerce for Intellectual Property and
Director of the United States Patent and Trademark Office*